United States Patent
Cecere et al.

(10) Patent No.: US 10,023,559 B2
(45) Date of Patent: Jul. 17, 2018

(54) SUBSTITUTED AZETIDINE DERIVATIVES

(71) Applicant: Hoffmann-La Roche Inc., Little Falls, NJ (US)

(72) Inventors: Giuseppe Cecere, Basel (CH); Guido Galley, Rheinfelden (DE); Roger Norcross, Olsberg (CH); Philippe Pflieger, Schwoben (FR); Etienne Rauber, Rantzwiller (FR)

(73) Assignee: Hoffman-La Roche Inc., Little Falls, NJ (US)

( * ) Notice: Subject to any disclaimer, the term of this patent is extended or adjusted under 35 U.S.C. 154(b) by 5 days.

(21) Appl. No.: 15/427,261

(22) Filed: Feb. 8, 2017

(65) Prior Publication Data
US 2017/0144994 A1    May 25, 2017

Related U.S. Application Data

(63) Continuation of application No. PCT/EP2015/069315, filed on Aug. 24, 2015.

(30) Foreign Application Priority Data

Aug. 27, 2014  (EP) .................................... 14182445

(51) Int. Cl.
C07D 403/12    (2006.01)
C07D 401/12    (2006.01)
C07D 205/04    (2006.01)

(52) U.S. Cl.
CPC ......... C07D 403/12 (2013.01); C07D 205/04 (2013.01); C07D 401/12 (2013.01)

(58) Field of Classification Search
CPC ... C07D 403/12; C07D 401/12; C07D 205/04
See application file for complete search history.

(56) References Cited

U.S. PATENT DOCUMENTS

| | | | | |
|---|---|---|---|---|
| 5,130,309 A | * | 7/1992 | Shanklin, Jr. | A61K 31/395 514/210.01 |
| 8,575,364 B2 | * | 11/2013 | Carruthers | C07D 205/04 548/952 |
| 2010/0190771 A1 | | 7/2010 | Claffey et al. | |

FOREIGN PATENT DOCUMENTS

| | | |
|---|---|---|
| DE | 10 2004 061 748 A1 | 7/2006 |
| GB | 2085427  * | 4/1982 |
| WO | 2008/142454 A1 | 11/2008 |
| WO | 2009/016048 A1 | 2/2009 |
| WO | 2010/060952 A1 | 6/2010 |
| WO | 2010/084438 A1 | 7/2010 |
| WO | 2013/170072 A2 | 11/2013 |

OTHER PUBLICATIONS

Hodgson David M. et al., "Lithiation-Electrophilic Substitution of N-Thiopivaloylazetidine" Angewandte Chemie International Edition 49(16):2900-2903 (Jan. 1, 2010).
ISR for PCT/EP2015/069315.
Testa Emilio et al., "Substances acting on the central nervous system. XXI.Chemistry of azetidines. V. 3-Monosubstituted azetidines" Justus Liebigs Annalen der Chemie 647:92-100 (Apr. 20, 1961) (in German).
Written Opinion for PCT/EP2015/069315.
CAS Registry Database No. 1203683-27-5, 1 page (2018).

* cited by examiner

*Primary Examiner* — Alexander R Pagano
*Assistant Examiner* — Ebenezer O Sackey
(74) *Attorney, Agent, or Firm* — Brian L. Buckwalter

(57) ABSTRACT

The present invention relates to compounds of formula of formula I wherein R, $R^1$, $R^2$, $R^{2'}$, $R^3$, $R^4$, $R^5$, $L^1$, $L^2$ and N are as described herein, compositions containing compounds of formula I, methods of manufacture of compounds of formula I and methods of treating psychiatric, metabolic, cardiovascular or sleep disorders with compounds of formula I.

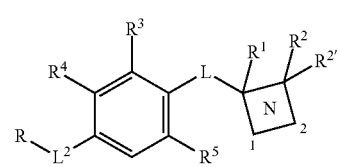

4 Claims, No Drawings

SUBSTITUTED AZETIDINE DERIVATIVES

CROSS REFERENCE TO RELATED APPLICATIONS

This application is a continuation of International Application No. PCT/EP2015/069315 having an international filing date of Aug. 24, 2015 and which claims benefit under 35 U.S.C. § 119 to European Patent Application No. 14182445.8 filed Aug. 27, 2014. The entire contents of both are incorporated herein by reference.

FIELD OF THE INVENTION

The present invention relates to novel compounds of formula I, as described herein, having pharmaceutical activity, their manufacture, pharmaceutical compositions containing them and their potential use as medicaments.

BACKGROUND OF THE INVENTION

Aberrant activity of Trace Amine Associated Receptors (TAARs), especially for TAAR1 is associated with psychiatric conditions such as depression, anxiety disorders, bipolar disorder, attention deficit hyperactivity disorder (ADHD), stress-related disorders, psychotic disorders such as schizophrenia, neurological diseases such as Parkinson's disease, neurodegenerative disorders such as Alzheimer's disease, epilepsy, migraine, hypertension, substance abuse and metabolic disorders such as eating disorders, diabetes, diabetic complications, obesity, dyslipidemia, disorders of energy consumption and assimilation, disorders and malfunction of body temperature homeostasis, disorders of sleep and circadian rhythm, and cardiovascular disorders.

Some of the physiological effects (i.e. cardiovascular effects, hypotension, induction of sedation) which have been reported for compounds which may bind to adrenergic receptors (WO02/076950, WO97/12874 or EP 0717 037) may be considered to be undesirable side effects in the case of medicaments aimed at treating diseases of the central nervous system as described above. Therefore it is desirable to obtain medicaments having selectivity for the TAAR1 receptor vs adrenergic receptors. Objects of the present invention show selectivity for TAAR1 receptor over adrenergic receptors, in particular good selectivity vs the human and rat alpha1 and alpha2 adrenergic receptors.

The classical biogenic amines (serotonin, norepinephrine, epinephrine, dopamine, histamine) play important roles as neurotransmitters in the central and peripheral nervous system [1]. Their synthesis and storage, as well as their degradation and reuptake after release are tightly regulated. An imbalance in the levels of biogenic amines is known to be responsible for the altered brain function under many pathological conditions [2-5]. A second class of endogenous amine compounds, the so-called trace amines (TAs) significantly overlaps with the classical biogenic amines regarding structure, metabolism and subcellular localization. The TAs include p-tyramine, β-phenylethylamine, tryptamine and octopamine, and they are present in the mammalian nervous system at generally lower levels than classical biogenic amines [6].

Their dysregulation has been linked to various psychiatric diseases like schizophrenia and depression [7] and for other conditions like attention deficit hyperactivity disorder, migraine headache, Parkinson's disease, substance abuse and eating disorders [8,9].

For a long time, TA-specific receptors had only been hypothesized based on anatomically discrete high-affinity TA binding sites in the CNS of humans and other mammals [10,11]. Accordingly, the pharmacological effects of TAs were believed to be mediated through the well-known machinery of classical biogenic amines, by either triggering their release, inhibiting their reuptake or by "crossreacting" with their receptor systems [9,12,13]. This view changed significantly with the recent identification of several members of a novel family of GPCRs, the trace amine associated receptors (TAARs) [7,14]. There are 9 TAAR genes in human (including 3 pseudogenes) and 16 genes in mouse (including 1 pseudogene). The TAAR genes do not contain introns (with one exception, TAAR2 contains 1 intron) and are located next to each other on the same chromosomal segment. The phylogenetic relationship of the receptor genes, in agreement with an in-depth GPCR pharmacophore similarity comparison, and pharmacological data suggest that these receptors form three distinct subfamilies [7,14]. TAAR1 is in the first subclass of four genes (TAAR1-4) highly conserved between human and rodents. TAs activate TAAR1 via Gαs. Dysregulation of TAs was shown to contribute to the etiology of various diseases like depression, psychosis, attention deficit hyperactivity disorder, substance abuse, Parkinson's disease, migraine headache, eating disorders, metabolic disorders and therefore TAAR1 ligands have a high potential for the treatment of these diseases.

REFERENCES USED

1 Deutch, A. Y. and Roth, R. H. (1999) Neurotransmitters. In *Fundamental Neuroscience* ($2^{nd}$ edn) (Zigmond, M. J., Bloom, F. E., Landis, S. C., Roberts, J. L, and Squire, L. R., eds.), pp. 193-234, Academic Press;

2 Wong, M. L. and Licinio, J. (2001) Research and treatment approaches to depression. *Nat. Rev. Neurosci.* 2, 343-351;

3 Carlsson, A. et al. (2001) Interactions between monoamines, glutamate, and GABA in schizophrenia: new evidence. *Annu. Rev. Pharmacol. Toxicol.* 41, 237-260;

4 Tuite, P. and Riss, J. (2003) Recent developments in the pharmacological treatment of Parkinson's disease. *Expert Opin. Investig. Drugs* 12, 1335-1352, 5 Castellanos, F. X. and Tannock, R. (2002) Neuroscience of attention-deficit/hyperactivity disorder: the search for endophenotypes. *Nat. Rev. Neurosci.* 3, 617-628;

6 Usdin, Earl; Sandler, Merton; Editors. *Psychopharmacology Series, Vol. 1: Trace Amines and the Brain. [Proceedings of a Study Group at the 14th Annual Meeting of the American College of Neuropsychoparmacology*, San Juan, Puerto Rico] (1976);

7 Lindemann, L. and Hoener, M. (2005) A renaissance in trace amines inspired by a novel GPCR family. *Trends in Pharmacol. Sci.* 26, 274-281;

8 Branchek, T. A. and Blackburn, T. P. (2003) Trace amine receptors as targets for novel therapeutics: legend, myth and fact. *Curr. Opin. Pharmacol.* 3, 90-97;

9 Premont, R. T. et al. (2001) Following the trace of elusive amines. *Proc. Natl. Acad. Sci. U.S.A.* 98, 9474-9475;

10 Mousseau, D. D. and Butterworth, R. F. (1995) A high-affinity [3H] tryptamine binding site in human brain. *Prog. Brain Res.* 106, 285-291;

11 McCormack, J. K. et al. (1986) Autoradiographic localization of tryptamine binding sites in the rat and dog central nervous system. *J. Neurosci.* 6, 94-101;

12 Dyck, L. E. (1989) Release of some endogenous trace amines from rat striatal slices in the presence and absence of a monoamine oxidase inhibitor. *Life Sci.* 44, 1149-1156;

13 Parker, E. M. and Cubeddu, L. X. (1988) Comparative effects of amphetamine, phenylethylamine and related drugs on dopamine efflux, dopamine uptake and mazindol binding. *J. Pharmacol. Exp. Ther.* 245, 199-210;

14 Lindemann, L. et al. (2005) Trace amine associated receptors form structurally and functionally distinct subfamilies of novel G protein-coupled receptors. *Genomics* 85, 372-385.

BRIEF SUMMARY OF THE INVENTION

The invention relates to compounds of formula I

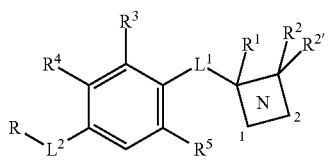

wherein
R$^1$ is hydrogen, methoxy or fluoro, or is absent for L$^1$ being —HC=;
R$^2$/R$^{2'}$ are independently from each other hydrogen, methoxy or fluoro;
R$^3$/R$^4$ are independently from each other hydrogen or halogen;
R$^5$ is hydrogen or fluoro;
L$^1$ is CH$_2$—, —NR'—, —O—, —S— or CF$_2$—, or is —HC= if R$^1$ is absent;
R' is hydrogen or lower alkyl;
L$^2$ is a bond, —C(O)NH—, —NH—, —CH$_2$NHC(O)—, —NHC(O)— or —NHC(O)NH—;
R is hydrogen or is phenyl optionally substituted by one or more substituents, selected from halogen, lower alkyl substituted by halogen or lower alkoxy, or is a five or six membered heteroaryl, selected from pyridinyl, pyrimidinyl, pyrazinyl, pyridazinyl or pyrazolyl, which heteroaryls are optionally substituted by one or more substituents, selected from halogen, lower alkyl, lower alkoxy, cyano, cycloalkyl, lower alkyl substituted by halogen, lower alkoxy substituted by halogen or by phenyl substituted by halogen, or is halogen, lower alkoxy or cyano, if L$^2$ is a bond;
N is a ring nitrogen atom in position 1 or 2;
or to a pharmaceutically suitable acid addition salt thereof, to all racemic mixtures, all their corresponding enantiomers and/or optical isomers.

In another embodiment, the present inventions provide for pharmaceutical compositions comprising compounds of Formula I.

In another embodiment, the present invention provides for methods of treating disease associated with trace amine associated receptors.

DETAILED DESCRIPTION OF THE INVENTION

There is a broad interest to increase the knowledge about trace amine associated receptors. Objects of the present invention are new compounds of formula I and their pharmaceutically acceptable salts, their use for the manufacture of medicaments for the treatment of diseases related to the biological function of the trace amine associated receptors, their manufacture and medicaments based on a compound in accordance with the invention in the control or prevention of illnesses such as depression, anxiety disorders, bipolar disorder, attention deficit hyperactivity disorder, stress-related disorders, psychotic disorders such as schizophrenia, neurological diseases such as Parkinson's disease, neurodegenerative disorders such as Alzheimer's disease, epilepsy, migraine, substance abuse and metabolic disorders such as eating disorders, diabetes, diabetic complications, obesity, dyslipidemia, disorders of energy consumption and assimilation, disorders and malfunction of body temperature homeostasis, disorders of sleep and circadian rhythm, and cardiovascular disorders.

The preferred indications using the compounds of the present invention are depression, psychosis, Parkinson's disease, anxiety, attention deficit hyperactivity disorder (ADHD) and diabetes.

As used herein, the term "lower alkyl" denotes a saturated straight- or branched-chain group containing from 1 to 7 carbon atoms, for example, methyl, ethyl, propyl, isopropyl, n-butyl, i-butyl, 2-butyl, t-butyl and the like. Preferred alkyl groups are groups with 1-4 carbon atoms.

As used herein, the term "lower alkoxy" denotes a group wherein the alkyl residue is as defined above and which is attached via an oxygen atom.

The term "halogen" denotes chlorine, iodine, fluorine and bromine. The preferred halogen group is fluorine.

As used herein, the term "lower alkyl substituted by halogen" denotes a saturated straight- or branched-chain group containing from 1 to 7 carbon atoms as defined for the term "lower alkyl", wherein at least one hydrogen atom is replaced by a halogen atom. A preferred halogen atom is fluoro. Examples of such groups are CF$_3$, CHF$_2$, CH$_2$F, CH$_2$CF$_3$ or CH$_2$CHF$_2$.

As used herein, the term "lower alkoxy substituted by halogen" denotes a lower alkoxy group as defined above, wherein at least one hydrogen atom is replaced by a halogen atom. Examples of such groups are OCF$_3$, OCHF$_2$, OCH$_2$F, OCH$_2$CF$_3$ or OCH$_2$CHF$_2$.

The term "cycloalkyl" denotes a saturated carbon ring, containing from 3 to 6 carbon atoms, for example cyclopropyl, cyclobutyl, cyclopentyl or cyclohexyl.

N is a ring heteroatom in position 1 or 2 of a four-membered ring and represents a azetidin-3-yl and azetidin-2-yl moiety

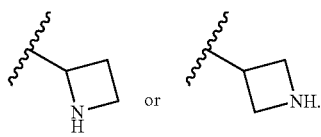 [SMILES: *C1CCN1 ; "or" ; *C1CNC1]

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methanesulfonic acid, p-toluenesulfonic acid and the like.

One embodiment of the invention are compounds of formula IA

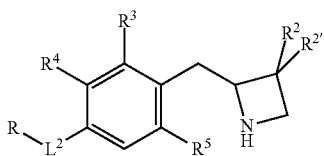

wherein
$R^2/R^{2'}$ are independently from each other hydrogen, methoxy or fluoro;
$R^3/R^4$ are independently from each other hydrogen or halogen;
$R^5$ is hydrogen or fluoro;
$L^2$ is a bond, —C(O)NH—, —NH—, —CH$_2$NHC(O)—, —NHC(O)— or —NHC(O)NH—;
R is hydrogen or is phenyl optionally substituted by one or more substituents, selected from halogen, lower alkyl substituted by halogen or lower alkoxy, or is a five or six membered heteroaryl, selected from pyridinyl, pyrimidinyl, pyrazinyl, pyridazinyl or pyrazolyl, which heteroaryls are optionally substituted by one or more substituents, selected from halogen, lower alkyl, lower alkoxy, cyano, cycloalkyl, lower alkyl substituted by halogen, lower alkoxy substituted by halogen or by phenyl substituted by halogen, or is halogen, lower alkoxy or cyano, if $L^2$ is a bond;

or a pharmaceutically suitable acid addition salt thereof, all racemic mixtures, all their corresponding enantiomers and/or optical isomers.

Another embodiment of the invention is a compound of formula IA selected the group consisting of:

N-[4-[[(2S)-azetidin-2-yl]methyl]phenyl]-4-chloro-benzamide;
N-[4-[[(2R)-azetidin-2-yl]methyl]phenyl]-4-chloro-benzamide;
N-[4-[[(2R)-azetidin-2-yl]methyl]phenyl]-2-(trifluoromethyl)pyrimidine-5-carboxamide;
N-[4-[[(2R)-azetidin-2-yl]methyl]phenyl]-6-chloro-pyridine-3-carboxamide;
N-[4-[[(2S)-azetidin-2-yl]methyl]phenyl]-2-(trifluoromethyl)pyrimidine-5-carboxamide;
N-[4-[[(2S)-azetidin-2-yl]methyl]phenyl]-6-chloro-pyridine-3-carboxamide;
(S)-2-benzylazetidine;
(2S,3S)-2-benzyl-3-fluoroazetidine;
(2S,3R)-2-benzyl-3-fluoroazetidine;
(2R,3R)-2-benzyl-3-fluoroazetidine;
(2R,3 S)-2-benzyl-3-fluoroazetidine;
(2S,3S)-2-benzyl-3-methoxyazetidine;
(2S,3R)-2-benzyl-3-methoxyazetidine;
(2S,3S)-3-fluoro-2-(4-methoxybenzyl)azetidine;
(2S,3R)-3-fluoro-2-(4-methoxybenzyl)azetidine;
(2R,3R)-3-fluoro-2-(4-methoxybenzyl)azetidine;
(2R,3 S)-3-fluoro-2-(4-methoxybenzyl)azetidine;
(2R,3R)-2-benzyl-3-methoxyazetidine;
(2R,3 S)-2-benzyl-3-methoxyazetidine;
3-ethyl-N-(4-(((2S,3S)-3-fluoroazetidin-2-yl)methyl)phenyl)-4-methyl-1H-pyrazole-5-carboxamide;
3-ethyl-N-(4-(((2R,3R)-3-fluoroazetidin-2-yl)methyl)phenyl)-4-methyl-1H-pyrazole-5-carboxamide;
N-(4-(((2S,3S)-3-fluoroazetidin-2-yl)methyl)phenyl)-2-(trifluoromethyl)isonicotinamide;
N-(4-(((2R,3R)-3-fluoroazetidin-2-yl)methyl)phenyl)-6-methyl-2-(trifluoromethyl)pyrimidine-4-carboxamide;
N-(4-(((2R,3R)-3-fluoroazetidin-2-yl)methyl)phenyl)-2-methoxyisonicotinamide;
N-(4-(((2R,3R)-3-fluoroazetidin-2-yl)methyl)phenyl)-2-(trifluoromethyl)isonicotinamide;
6-ethoxy-N-(4-(((2R,3R)-3-fluoroazetidin-2-yl)methyl)phenyl)nicotinamide;
N-(4-(((2R,3R)-3-fluoroazetidin-2-yl)methyl)phenyl)-2-(trifluoromethyl)pyrimidine-5-carboxamide;
2-cyclopropyl-N-(4-(((2R,3R)-3-fluoroazetidin-2-yl)methyl)phenyl)pyrimidine-5-carboxamide;
N-(4-(((2R,3R)-3-fluoroazetidin-2-yl)methyl)phenyl)-3-isopropyl-1H-pyrazole-5-carboxamide;
N-(4-(((2S,3S)-3-fluoroazetidin-2-yl)methyl)phenyl)-6-methyl-2-(trifluoromethyl)pyrimidine-4-carboxamide;
N-(4-(((2S,3S)-3-fluoroazetidin-2-yl)methyl)phenyl)-2-methoxyisonicotinamide;
6-ethoxy-N-(4-(((2S,3S)-3-fluoroazetidin-2-yl)methyl)phenyl)nicotinamide;
2-cyclopropyl-N-(4-(((2S,3S)-3-fluoroazetidin-2-yl)methyl)phenyl)pyrimidine-5-carboxamide;
N-(4-(((2S,3S)-3-fluoroazetidin-2-yl)methyl)phenyl)-2-(trifluoromethyl)pyrimidine-5-carboxamide;
N-(4-(((2S,3S)-3-fluoroazetidin-2-yl)methyl)phenyl)-3-isopropyl-1-methyl-1H-pyrazole-5-carboxamide;
1-[4-[[(2S,3S)-3-fluoroazetidin-2-yl]methyl]phenyl]-3-[6-(trifluoromethyl)-3-pyridyl]urea;
N-[4-[[(2S,3S)-3-fluoroazetidin-2-yl]methyl]phenyl]-3-isopropyl-1H-pyrazole-5-carboxamide;
1-[4-[[(2R,3R)-3-fluoroazetidin-2-yl]methyl]phenyl]-3-[6-(trifluoromethyl)-3-pyridyl]urea;
1-(5-cyano-2-methoxy-phenyl)-3-[4[[(2R,3R)-3-fluoroazetidin-2-yl]methyl]phenyl]urea;
1-(5-cyano-2-methoxy-phenyl)-3-[4-[[(2S,3S)-3-fluoroazetidin-2-yl]methyl]phenyl]urea; and
4-{[(2S,3S)-3-fluoroazetidin-2-yl]methyl]}-N-(3-pyridyl)benzamide.

Another embodiment of the invention are compounds of formula IB

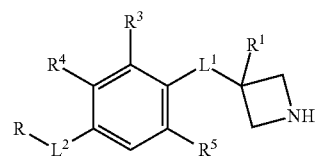

wherein
$R^1$ is hydrogen, methoxy or fluoro, or is absent for $L^1$ being —HC═;
$R^2/R^{2'}$ are independently from each other hydrogen, methoxy or fluoro;
$R^3/R^4$ are independently from each other hydrogen or halogen;
$R^5$ is hydrogen or fluoro;
$L^1$ is —CH$_2$—, —NR'—, —O—, —S— or CF$_2$—, or is —HC═ if $R^1$ is absent;
R' is hydrogen or lower alkyl;
$L^2$ is a bond, —C(O)NH—, —NH—, —CH$_2$NHC(O)—, —NHC(O)— or —NHC(O)NH—;
R is hydrogen or is phenyl optionally substituted by one or more substituents, selected from halogen, lower alkyl substituted by halogen or lower alkoxy, or is a five or six membered heteroaryl, selected from pyridinyl, pyrimidinyl, pyrazinyl, pyridazinyl or pyrazolyl, which heteroaryls are optionally substituted by one or more substituents, selected from halogen, lower alkyl, lower alkoxy, cyano, cycloalkyl, lower alkyl substituted by halogen, lower alkoxy substituted by halogen or by phenyl substituted by halogen, or is halogen, lower alkoxy or cyano, if $L^2$ is a bond; or a pharmaceutically suitable acid addition salt thereof, all racemic mixtures, all their corresponding enantiomers and/or optical isomers.

Another embodiment of the invention is a compound of formula IB selected the group consisting of:

3-benzylazetidine;
N-[4-[azetidin-3-yl(methyl)amino]phenyl]-2-(trifluoromethyl)pyridine-4-carboxamide;
N-[4-(azetidin-3-ylamino)phenyl]-2-(trifluoromethyl)pyridine-4-carboxamide;
N-(4-(azetidin-3-yloxy)phenyl)-4-chlorobenzamide;
N-(4-(azetidin-3-yloxy)phenyl)-2-(trifluoromethyl)isonicotinamide;
N-(4-(azetidin-3-yloxy)phenyl)-2-(trifluoromethyl)pyrimidine-5-carboxamide;
N-(4-(azetidin-3-yloxy)phenyl)-2-cyano-6-methoxyisonicotinamide;
N-[4-(azetidin-3-yloxy)phenyl]-2-(trifluoromethyl)pyrimidin-4-amine;
N-(4-(azetidin-3-yloxy)phenyl)-5-(trifluoromethyl)pyrimidin-2-amine;
N-(4-(azetidin-3-yloxy)phenyl)-3-cyclopropyl-1H-pyrazole-5-carboxamide;
N-(4-(azetidin-3-yloxy)phenyl)-3-ethyl-4-methyl-1H-pyrazole-5-carboxamide;
N-(4-(azetidin-3-yloxy)phenyl)-3-isopropyl-1H-pyrazole-5-carboxamide;
N-(4-(azetidin-3-yloxy)phenyl)-4-chloro-3-cyclopropyl-1H-pyrazole-5-carboxamide;
N-(4-(azetidin-3-yloxy)phenyl)-2-cyclopropylpyrimidine-5-carboxamide;
N-[4-(azetidin-3-yloxy)phenyl]-2-ethyl-pyrimidine-5-carboxamide;
N-[4-(azetidin-3-yloxy)phenyl]-2-methyl-pyrimidine-5-carboxamide;
N-[4-(azetidin-3-yloxy)phenyl]-2-methyl-5-(trifluoromethyl)pyrazole-3-carboxamide;
4-(azetidin-3-yloxy)-N-[(4-fluorophenyl)methyl]benzamide;
N-(4-(azetidin-3-yloxy)phenyl)-2-(2,2,2-trifluoroethoxy)pyrimidine-5-carboxamide;
4-(azetidin-3-yloxy)-N-phenyl-benzamide;
N-[4-(azetidin-3-yloxy)phenyl]-4-chloro-1-(2,2,2-trifluoroethyl)pyrazole-3-carboxamide;
N-[4-(azetidin-3-yloxy)phenyl]-4-chloro-1-ethyl-pyrazole-3-carboxamide;
4-(azetidin-3-yloxy)-N-(4-chlorophenyl)benzamide;
N-(4-(azetidin-3-yloxy)phenyl)-3-(trifluoromethyl)-1H-pyrazole-5-carboxamide;
N-[4-(azetidin-3-yloxy)-3-fluoro-phenyl]-4-chloro-3-cyclopropyl-1H-pyrazole-5-carboxamide;
N-[4-(azetidin-3-yloxy)-3-fluoro-phenyl]-2-(trifluoromethyl)pyrimidine-5-carboxamide;
N-[4-(azetidin-3-yloxy)-3-fluoro-phenyl]-2-cyclopropyl-pyrimidine-5-carboxamide;
N-[4-(azetidin-3-yloxy)-3-fluoro-phenyl]-6-ethoxy-pyridine-3-carboxamide;
N-[4-(azetidin-3-yloxy)phenyl]-4-chloro-2-methyl-5-(trifluoromethyl)pyrazole-3-carboxamide;
4-(azetidin-3-yloxy)-N-(6-chloropyridin-3-yl)benzamide;
N-[4-(azetidin-3-yloxy)phenyl]-4-bromo-3-cyclopropyl-1H-pyrazole-5-carboxamide;
N-[4-(azetidin-3-yloxy)phenyl]-3-tert-butyl-4-chloro-1H-pyrazole-5-carboxamide;
N-[4-(azetidin-3-yloxy)phenyl]-4-chloro-3-isopropyl-1H-pyrazole-5-carboxamide;
N-[4-(azetidin-3-yloxy)phenyl]-4-chloro-3-(4-chlorophenyl)-1H-pyrazole-5-carboxamide;
N-[4-(azetidin-3-ylsulfanyl)phenyl]-4-chloro-3-cyclopropyl-1H-pyrazole-5-carboxamide;
N-[4-(azetidin-3-yloxy)-2-fluoro-phenyl]-4-chloro-3-cyclopropyl-1H-pyrazole-5-carboxamide;
4-(azetidin-3-yloxy)-N-(4-chloro-3-(trifluoromethyl)phenyl)benzamide;
N-[4-(azetidin-3-yloxy)-2-fluoro-phenyl]-2-cyclopropyl-pyrimidine-5-carboxamide;
N-[4-(azetidin-3-yloxy)-2-fluoro-phenyl]-2-(trifluoromethyl)pyrimidine-5-carboxamide;
N-[4-(azetidin-3-yloxy)phenyl]-4-chloro-3-(trifluoromethyl)-1H-pyrazole-5-carboxamide;
N-[4-(azetidin-3-yloxy)phenyl]-4-chloro-3-ethyl-1H-pyrazole-5-carboxamide;
N-[4-(azetidin-3-yloxy)phenyl]-3-cyclopropyl-4-fluoro-1H-pyrazole-5-carboxamide;
N-[4-(azetidin-3-yloxy)phenyl]-4-chloro-1-methyl-5-(trifluoromethyl)pyrazole-3-carboxamide;
N-[4-(azetidin-3-ylsulfanyl)phenyl]-2-cyclopropyl-pyrimidine-5-carboxamide;
N-[4-(azetidin-3-ylsulfanyl)phenyl]-2-(trifluoromethyl)pyrimidine-5-carboxamide;
3-benzyl-3-fluoro-azetidine;
N-[4-(azetidin-3-yloxy)phenyl]-4-bromo-3-methyl-1H-pyrazole-5-carboxamide;
3-[(4-bromophenyl)-difluoro-methyl]azetidine;
N-[4-[azetidin-3-yl(difluoro)methyl]phenyl]-4-chloro-benzamide;
4-chloro-N-[4-[(3-fluoroazetidin-3-yl)methyl]phenyl]benzamide;
4-(azetidin-3-yloxy)-2-chloro-N-(6-chloro-3-pyridyl)benzamide;
6-chloro-N-[4-[(3-fluoroazetidin-3-yl)methyl]phenyl]pyridine-3-carboxamide;
N-[4-[(3-fluoroazetidin-3-yl)methyl]phenyl]-2-(trifluoromethyl)pyrimidine-5-carboxamide;
4-chloro-3-cyclopropyl-N-[4-[(3-fluoroazetidin-3-yl)methyl]phenyl]-1H-pyrazole-5-carboxamide;
N-[4-[(3-fluoroazetidin-3-yl)methyl]phenyl]-5-(2,2,2-trifluoroethoxy)pyrazine-2-carboxamide;
N-[4-(azetidin-3-ylmethyl)phenyl]-6-chloro-pyridine-3-carboxamide;
4-chloro-3-ethyl-N-[4-[(3-fluoroazetidin-3-yl)methyl]phenyl]-1H-pyrazole-5-carboxamide;
6-ethoxy-N-[4-[(3-fluoroazetidin-3-yl)methyl]phenyl]pyridazine-3-carboxamide;
6 N-[4-[(3-fluoroazetidin-3-yl)methyl]phenyl]-6-m ethoxy-2-(trifluoromethyl)pyrimidine-4-carboxamide;
N-[4-[(3-fluoroazetidin-3-yl)methyl]phenyl]-2-(2,2,2-trifluoroethoxy)pyrimidine-5-carboxamide
N-[4-[(3-fluoroazetidin-3-yl)methyl]phenyl]-5-(trifluoromethyl)pyrazine-2-carboxamide;
6-chloro-N-[4-[(3-methoxyazetidin-3-yl)methyl]phenyl]pyridine-3-carboxamide;
N-[4-[(3-methoxyazetidin-3-yl)methyl]phenyl]-2-(trifluoromethyl)pyrimidine-5-carboxamide;
N-[4-(azetidin-3-yloxy)phenyl]-5-(trifluoromethyl)pyrazine-2-carboxamide;
N-[4-(azetidin-3-yloxy)phenyl]-6-ethoxy-pyridazine-3-carboxamide;

N-[4-(azetidin-3-yloxy)phenyl]-5-(2,2,2-trifluoroethoxy)pyrazine-2-carboxamide;
1-[4-[(3-fluoroazetidin-3-yl)methyl]phenyl]-3-[4-(trifluoromethyl)phenyl]urea;
1-[4-[(3-fluoroazetidin-3-yl)methyl]phenyl]-3-(4-methoxyphenyl)urea;
1-(3-chlorophenyl)-3-[4-[(3-fluoroazetidin-3-yl)methyl]phenyl]urea;
1-[4-(azetidin-3-yloxy)phenyl]-3-(4-methoxyphenyl)urea;
1-[4-(azetidin-3-yloxy)phenyl]-3-(3-chlorophenyl)urea;
1-[4-(azetidin-3-ylsulfanyl)phenyl]-3-[4-(trifluoromethyl)phenyl]urea;
1-[4-(azetidin-3-ylsulfanyl)phenyl]-3-(4-methoxyphenyl)urea;
1-[4-(azetidin-3-ylsulfanyl)phenyl]-3-(3-chlorophenyl)urea;
1-[4-(azetidin-3-ylmethyl)phenyl]-3-[4-(trifluoromethyl)phenyl]urea;
1-[4-(azetidin-3-ylmethyl)phenyl]-3-(4-methoxyphenyl)urea; and,
1-[4-(azetidin-3-ylmethyl)phenyl]-3-(4-methoxyphenyl)urea.

Another embodiment of the invention are compounds of formula IC

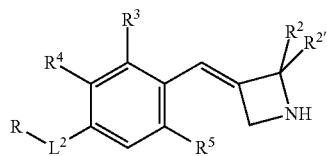

IC wherein
$R^2/R^{2'}$ are independently from each other hydrogen, methoxy or fluoro;
$R^3/R^4$ are independently from each other hydrogen or halogen;
$R^5$ is hydrogen or fluoro;
$L^2$ is a bond, —C(O)NH—, —NH—, —CH$_2$NHC(O)—, —NHC(O)— or —NHC(O)NH—;
R is hydrogen or is phenyl optionally substituted by one or more substituents, selected from halogen, lower alkyl substituted by halogen or lower alkoxy, or is a five or six membered heteroaryl, selected from pyridinyl, pyrimidinyl, pyrazinyl, pyridazinyl or pyrazolyl, which heteroaryls are optionally substituted by one or more substituents, selected from halogen, lower alkyl, lower alkoxy, cyano, cycloalkyl, lower alkyl substituted by halogen, lower alkoxy substituted by halogen or by phenyl substituted by halogen,
or is halogen, lower alkoxy or cyano, if $L^2$ is a bond;
or a pharmaceutically suitable acid addition salt thereof, all racemic mixtures, all their corresponding enantiomers and/or optical isomers.

Another embodiment of the invention is a compound of formula IC selected the group consisting of:
3-[(4-bromophenyl)methylene]azetidine;
N-[4-(azetidin-3-ylidenemethyl)phenyl]-4-chloro-3-cyclopropyl-1H-pyrazole-5-carboxamide;
N-[4-(azetidin-3-ylidenemethyl)phenyl]-2-(trifluoromethyl)pyrimidine-5-carboxamide;
N-[4-(azetidin-3-ylidenemethyl)phenyl]-2-(trifluoromethyl)pyridine-4-carboxamide;
N-[4-(azetidin-3-ylidenemethyl)phenyl]-4-chloro-benzamide;
N-[4-(azetidin-3-ylidenemethyl)phenyl]-2-(trifluoromethyl)pyrimidin-4-amine;
N-[4-(azetidin-3-ylidenemethyl)phenyl]-5-(trifluoromethyl)pyrimidin-2-amine;
N-[4-(azetidin-3-ylidenemethyl)phenyl]-6-chloro-pyridine-3-carboxamide;
N-(4-(azetidin-3-ylidenemethyl)-3,5-difluorophenyl)-6-methyl-2-(trifluoromethyl)pyrimidine-4-carboxamide;
N-(4-(azetidin-3-ylidenemethyl)-3,5-difluorophenyl)-3-ethyl-4-methyl-1H-pyrazole-5-carboxamide;
N-(4-(azetidin-3-ylidenemethyl)-3,5-difluorophenyl)-6-chloronicotinamide;
N-(4-(azetidin-3-ylidenemethyl)-3-fluorophenyl)-6-methyl-2-(trifluoromethyl)pyrimidine-4-carboxamide;
N-(4-(azetidin-3-ylidenemethyl)-3-fluorophenyl)-6-chloronicotinamide;
N-(4-(azetidin-3-ylidenemethyl)-3,5-difluorophenyl)-6-ethyl-2-(trifluoromethyl)pyrimidine-4-carboxamide;
N-(4-(azetidin-3-ylidenemethyl)-3-fluorophenyl)-3-ethyl-4-methyl-1H-pyrazole-5-carboxamide;
1-[4-(azetidin-3-ylidenemethyl)phenyl]-3-[4-(trifluoromethyl)phenyl]urea;
1-[4-(azetidin-3-ylidenemethyl)phenyl]-3-(4-methoxyphenyl)urea; and,
1-[4-(azetidin-3-ylidenemethyl)phenyl]-3-(3-chlorophenyl)urea.

One further embodiment of the invention are compounds of formula IB-1:

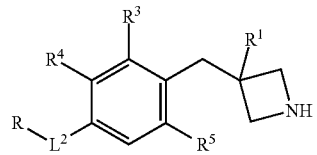

IB-1 in which the substituents are described above,
Another embodiment of the invention is a compound of formula IB-1 selected the group consisting of:
3-benzylazetidine;
3-benzyl-3-fluoro-azetidine;
4-chloro-N-[4-[(3-fluoroazetidin-3-yl)methyl]phenyl]benzamide;
6-chloro-N-[4-[(3-fluoroazetidin-3-yl)methyl]phenyl]pyridine-3-carboxamide;
N-[4-[(3-fluoroazetidin-3-yl)methyl]phenyl]-2-(trifluoromethyl)pyrimidine-5-carboxamide;
4-chloro-3-cyclopropyl-N-[4-[(3-fluoroazetidin-3-yl)methyl]phenyl]-1H-pyrazole-5-carboxamide;
N-[4-[(3-fluoroazetidin-3-yl)methyl]phenyl]-5-(2,2,2-trifluoroethoxy)pyrazine-2-carboxamide;
N-[4-(azetidin-3-ylmethyl)phenyl]-6-chloro-pyridine-3-carboxamide;
4-chloro-3-ethyl-N-[4-[(3-fluoroazetidin-3-yl)methyl]phenyl]-1H-pyrazole-5-carboxamide;
6-ethoxy-N-[4-[(3-fluoroazetidin-3-yl)methyl]phenyl]pyridazine-3-carboxamide;
N-[4-[(3-fluoroazetidin-3-yl)methyl]phenyl]-6-methoxy-2-(trifluoromethyl)pyrimidine-4-carboxamide;
N-[4-[(3-fluoroazetidin-3-yl)methyl]phenyl]-2-(2,2,2-trifluoroethoxy)pyrimidine-5-carboxamide;
N-[4-[(3-fluoroazetidin-3-yl)methyl]phenyl]-5-(trifluoromethyl)pyrazine-2-carboxamide;
6-chloro-N-[4-[(3-methoxyazetidin-3-yl)methyl]phenyl]pyridine-3-carboxamide;

N-[4-[(3-methoxyazetidin-3-yl)methyl]phenyl]-2-(trifluoromethyl)pyrimidine-5-carboxamide;
1-[4-[(3-fluoroazetidin-3-yl)methyl]phenyl]-3-[4-(trifluoromethyl)phenyl]urea;
1-[4-[(3-fluoroazetidin-3-yl)methyl]phenyl]-3-(4-methoxyphenyl)urea;
1-(3-chlorophenyl)-3-[4-[(3-fluoroazetidin-3-yl)methyl]phenyl]urea;
1-[4-(azetidin-3-ylmethyl)phenyl]-3-[4-(trifluoromethyl)phenyl]urea;
1-[4-(azetidin-3-ylmethyl)phenyl]-3-(4-methoxyphenyl)urea;
1-[4-(azetidin-3-ylmethyl)phenyl]-3-(3-chlorophenyl)urea;

Yet another embodiment of the invention are compounds of formula IB-2:

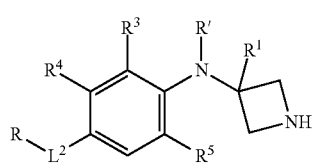

IB-2 in which the substituents are as described above, for example the following compounds:
N-[4-[azetidin-3-yl(methyl)amino]phenyl]-2-(trifluoromethyl)pyridine-4-carboxamide;
N-[4-(azetidin-3-ylamino)phenyl]-2-(trifluoromethyl)pyridine-4-carboxamide.

Yet another embodiment of the invention are compounds of formula IB-3:

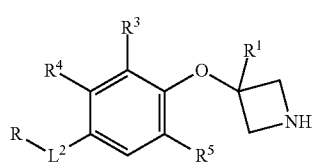

IB-3 in which the substituents are as described above.
Another embodiment of the invention is a compound of formula IB-3 selected the group consisting of:
N-(4-(azetidin-3-yloxy)phenyl)-4-chlorobenzamide;
N-(4-(azetidin-3-yloxy)phenyl)-2-(trifluoromethyl)isonicotinamide;
N-(4-(azetidin-3-yloxy)phenyl)-2-(trifluoromethyl)pyrimidine-5-carboxamide;
N-(4-(azetidin-3-yloxy)phenyl)-2-cyano-6-methoxyisonicotinamide;
N-[4-(azetidin-3-yloxy)phenyl]-2-(trifluoromethyl)pyrimidin-4-amine;
N-(4-(azetidin-3-yloxy)phenyl)-5-(trifluoromethyl)pyrimidin-2-amine;
N-(4-(azetidin-3-yloxy)phenyl)-3-cyclopropyl-1H-pyrazole-5-carboxamide;
N-(4-(azetidin-3-yloxy)phenyl)-3-ethyl-4-methyl-1H-pyrazole-5-carboxamide;
N-(4-(azetidin-3-yloxy)phenyl)-3-isopropyl-1H-pyrazole-5-carboxamide;
N-(4-(azetidin-3-yloxy)phenyl)-4-chloro-3-cyclopropyl-1H-pyrazole-5-carboxamide;
N-(4-(azetidin-3-yloxy)phenyl)-2-cyclopropylpyrimidine-5-carboxamide;
N-[4-(azetidin-3-yloxy)phenyl]-2-ethyl-pyrimidine-5-carboxamide;
N-[4-(azetidin-3-yloxy)phenyl]-2-methyl-pyrimidine-5-carboxamide;
N-[4-(azetidin-3-yloxy)phenyl]-2-methyl-5-(trifluoromethyl)pyrazole-3-carboxamide;
4-(azetidin-3-yloxy)-N-[(4-fluorophenyl)methyl]benzamide;
N-(4-(azetidin-3-yloxy)phenyl)-2-(2,2,2-trifluoroethoxy)pyrimidine-5-carboxamide;
4-(azetidin-3-yloxy)-N-phenyl-benzamide;
N-[4-(azetidin-3-yloxy)phenyl]-4-chloro-1-(2,2,2-trifluoroethyl)pyrazole-3-carboxamide;
N-[4-(azetidin-3-yloxy)phenyl]-4-chloro-1-ethyl-pyrazole-3-carboxamide;
4-(azetidin-3-yloxy)-N-(4-chlorophenyl)benzamide;
N-(4-(azetidin-3-yloxy)phenyl)-3-(trifluoromethyl)-1H-pyrazole-5-carboxamide;
N-[4-(azetidin-3-yloxy)-3-fluoro-phenyl]-4-chloro-3-cyclopropyl-1H-pyrazole-5-carboxamide;
N-[4-(azetidin-3-yloxy)-3-fluoro-phenyl]-2-(trifluoromethyl)pyrimidine-5-carboxamide;
N-[4-(azetidin-3-yloxy)-3-fluoro-phenyl]-2-cyclopropyl-pyrimidine-5-carboxamide;
N-[4-(azetidin-3-yloxy)-3-fluoro-phenyl]-6-ethoxy-pyridine-3-carboxamide;
N-[4-(azetidin-3-yloxy)phenyl]-4-chloro-2-methyl-5-(trifluoromethyl)pyrazole-3-carboxamide;
4-(azetidin-3-yloxy)-N-(6-chloropyridin-3-yl)benzamide;
N-[4-(azetidin-3-yloxy)phenyl]-4-bromo-3-cyclopropyl-1H-pyrazole-5-carboxamide;
N-[4-(azetidin-3-yloxy)phenyl]-3-tert-butyl-4-chloro-1H-pyrazole-5-carboxamide;
N-[4-(azetidin-3-yloxy)phenyl]-4-chloro-3-isopropyl-1H-pyrazole-5-carboxamide;
N-[4-(azetidin-3-yloxy)phenyl]-4-chloro-3-(4-chlorophenyl)-1H-pyrazole-5-carboxamide;
N-[4-(azetidin-3-yloxy)-2-fluoro-phenyl]-4-chloro-3-cyclopropyl-1H-pyrazole-5-carboxamide;
4-(azetidin-3-yloxy)-N-(4-chloro-3-(trifluoromethyl)phenyl)benzamide;
N-[4-(azetidin-3-yloxy)-2-fluoro-phenyl]-2-cyclopropyl-pyrimidine-5-carboxamide;
N-[4-(azetidin-3-yloxy)-2-fluoro-phenyl]-2-(trifluoromethyl)pyrimidine-5-carboxamide;
N-[4-(azetidin-3-yloxy)phenyl]-4-chloro-3-(trifluoromethyl)-1H-pyrazole-5-carboxamide;
N-[4-(azetidin-3-yloxy)phenyl]-4-chloro-3-ethyl-1H-pyrazole-5-carboxamide;
N-[4-(azetidin-3-yloxy)phenyl]-3-cyclopropyl-4-fluoro-1H-pyrazole-5-carboxamide;
N-[4-(azetidin-3-yloxy)phenyl]-4-chloro-1-methyl-5-(trifluoromethyl)pyrazole-3-carboxamide;
N-[4-(azetidin-3-yloxy)phenyl]-4-bromo-3-ethyl-1H-pyrazole-5-carboxamide;
N-[4-(azetidin-3-yloxy)phenyl]-4-bromo-3-methyl-1H-pyrazole-5-carboxamide;
4-(azetidin-3-yloxy)-2-chloro-N-(6-chloro-3-pyridyl)benzamide;
N-[4-(azetidin-3-yloxy)phenyl]-5-(trifluoromethyl)pyrazine-2-carboxamide;
N-[4-(azetidin-3-yloxy)phenyl]-6-ethoxy-pyridazine-3-carboxamide;
N-[4-(azetidin-3-yloxy)phenyl]-5-(2,2,2-trifluoroethoxy)pyrazine-2-carboxamide;
1-[4-(azetidin-3-yloxy)phenyl]-3-(4-methoxyphenyl)urea; and,
1-[4-(azetidin-3-yloxy)phenyl]-3-(3-chlorophenyl)urea One embodiment of the invention are compounds of formula IB-4:

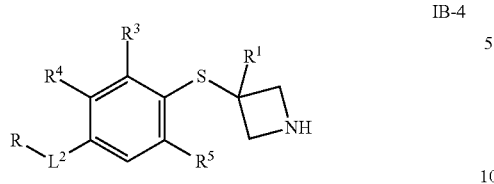

IB-4 in which the substituents are as described above, for example the following compounds:
N-[4-(azetidin-3-ylsulfanyl)phenyl]-4-chloro-3-cyclopropyl-1H-pyrazole-5-carboxamide
N-[4-(azetidin-3-yl sulfanyl)phenyl]-2-cyclopropyl-pyrimidine-5-carboxamide
N-[4-(azetidin-3-ylsulfanyl)phenyl]-2-(trifluoromethyl)pyrimidine-5-carboxamide
1-[4-(azetidin-3-ylsulfanyl)phenyl]-3-[4-(trifluoromethyl)phenyl]urea
1-[4-(azetidin-3-ylsulfanyl)phenyl]-3-(4-methoxyphenyl)urea
1-[4-(azetidin-3-ylsulfanyl)phenyl]-3-(3-chlorophenyl)urea One embodiment of the invention are compounds of formula IB-5:

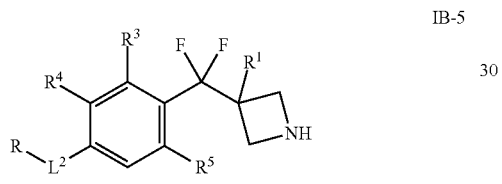

IB-5 in which the substituents are as described above, for example the following compounds:
3-[(4-bromophenyl)-difluoro-methyl]azetidine
N-[4-[azetidin-3-yl(difluoro)methyl]phenyl]-4-chloro-benzamide The preparation of compounds of formula I of the present invention may be carried out in sequential or convergent synthetic routes. Syntheses of the compounds of the invention are shown in the following schemes 1-15 and in the description of 137 specific examples. The skills required for carrying out the reaction and purification of the resulting products are known to those skilled in the art. The substituents and indices used in the following description of the processes have the significance given herein before unless indicated to the contrary.

In more detail, the compounds of formula I, can be manufactured by the methods given below, by the methods given in the examples or by analogous methods. Appropriate reaction conditions for the individual reaction steps are known to a person skilled in the art. The reaction sequence is not limited to the one displayed in schemes 1-15, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

The present compounds of formula IA, IB and IC and their pharmaceutically acceptable salts can be prepared by methods known in the art, for example, by processes described below, which process comprises a) cleaving off the N-protecting group (PG) from compounds of formula

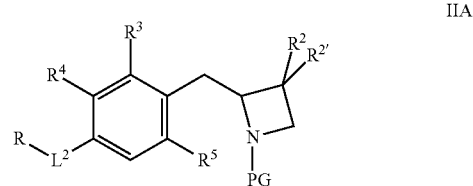

IIA

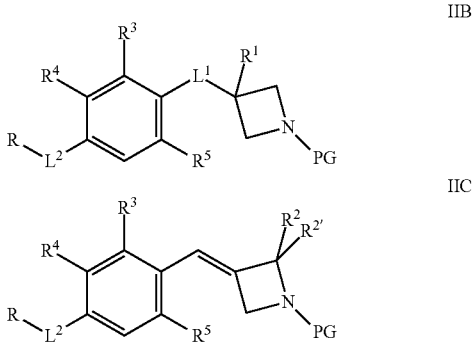

IIB

IIC to a compound of formula

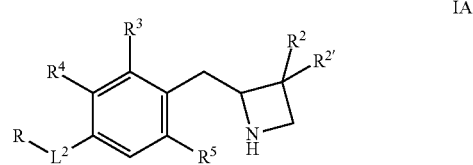

IA

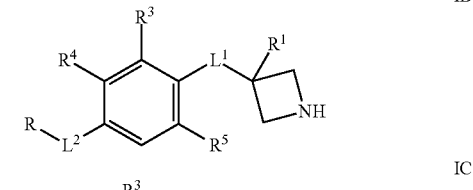

IB

IC wherein PG is a N-protecting group selected from —C(O)O-tert-butyl or —C(O)O-benzyl and the other definitions are as described above, and, if desired, converting the compounds obtained into pharmaceutically acceptable acid addition salts.

General Procedure

Scheme 1

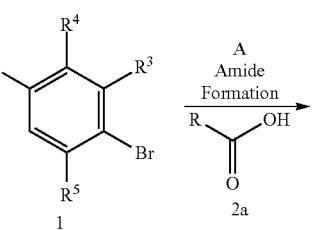

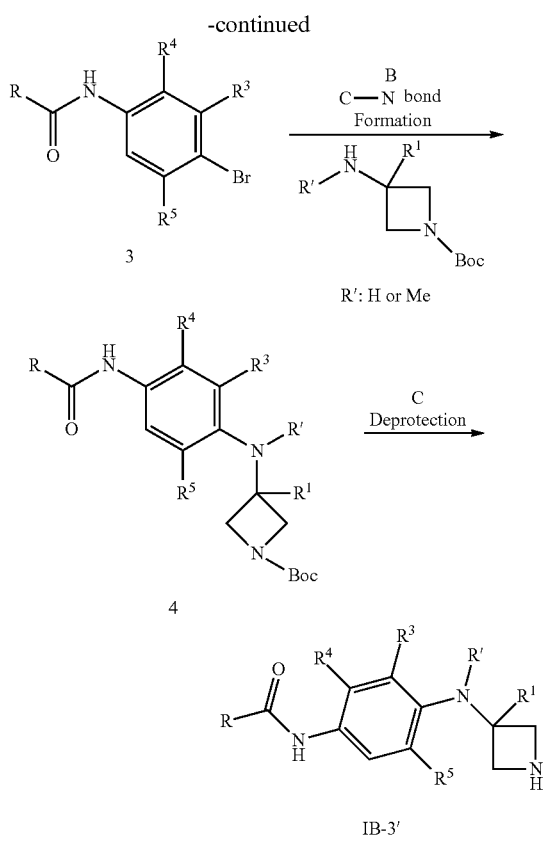

R': H or Me wherein R is phenyl optionally substituted by one or more substituents, selected from halogen, lower alkyl substituted by halogen or lower alkoxy, or is a five or six membered heteroaryl, selected from pyridinyl, pyrimidinyl, pyrazinyl, pyridazinyl or pyrazolyl, which heteroaryls are optionally substituted by one or more substituents, selected from halogen, lower alkyl, lower alkoxy, cyano, cycloalkyl, lower alkyl substituted by halogen, lower alkoxy substituted by halogen or by phenyl substituted by halogen, and wherein the substituents $R^3$, $R^4$ and are as described above;

Step A:

Amide formation can be accomplished by a coupling reaction between aniline 1 and a carboxylic acid 2a with a coupling reagent such as DCC, EDC, TBTU, HBTU or HATU in the presence of an organic base such as triethylamine, N,N-diisopropylethylamine or N-methylmorpholine in solvents such as dichloromethane, 1,2-dichloroethane, DMF, DMSO, or ethereal solvents including diethyl ether, 1,4-dioxane, THF, DME, or TBME.

Preferred conditions are HBTU with N-methylmorpholine in DMF at room temperature for 16 hours.

Step B:

Coupling reaction between aryl bromide 3 and tert-butyl 3-(methylamino)azetidine-1-carboxylate [CAS 454703-20-9] or tert-butyl 3-aminoazetidine-1-carboxylate [CAS 193269-78-2] can be accomplished by using a palladium or copper catalyst, a ligand, and a base in solvents such as 1,4-dioxane, DMF, THF, toluene, DMF and DMSO at elevated temperatures, for instance using a palladium-catalysed Buchwald-Hartwig reaction.

Preferred conditions with tert-butyl 3-(methylamino)azetidine-1-carboxylate are catalytic tris(dibenzylidineacetone)dipalladium(0), catalytic 2-dicyclohexylphosphino-2'-(N,N-dimethylamino)biphenyl (DavePhos), LiHMDS in THF at 65° C. for 16 hours.

Preferred conditions with tert-butyl 3-aminoazetidine-1-carboxylate are catalytic copper iodide(0), catalytic L-proline, $K_2CO_3$ in DMSO at 60° C. for 16 hours.

Step C:

Removal of N-Boc protecting group can be effected with mineral acids such as HCl, $H_2SO_4$, or $H_3PO_4$ or organic acids such as $CF_3COOH$, $CHCl_2COOH$, HOAc or p-toluenesulfonic acid in solvents such as $CH_2Cl_2$, $CHCl_3$, THF, MeOH, EtOH, or $H_2O$ at 0-80° C.

Preferred conditions are using $CF_3COOH$ in $CH_2Cl_2$ at room temperature for 2 hour.

Scheme 2

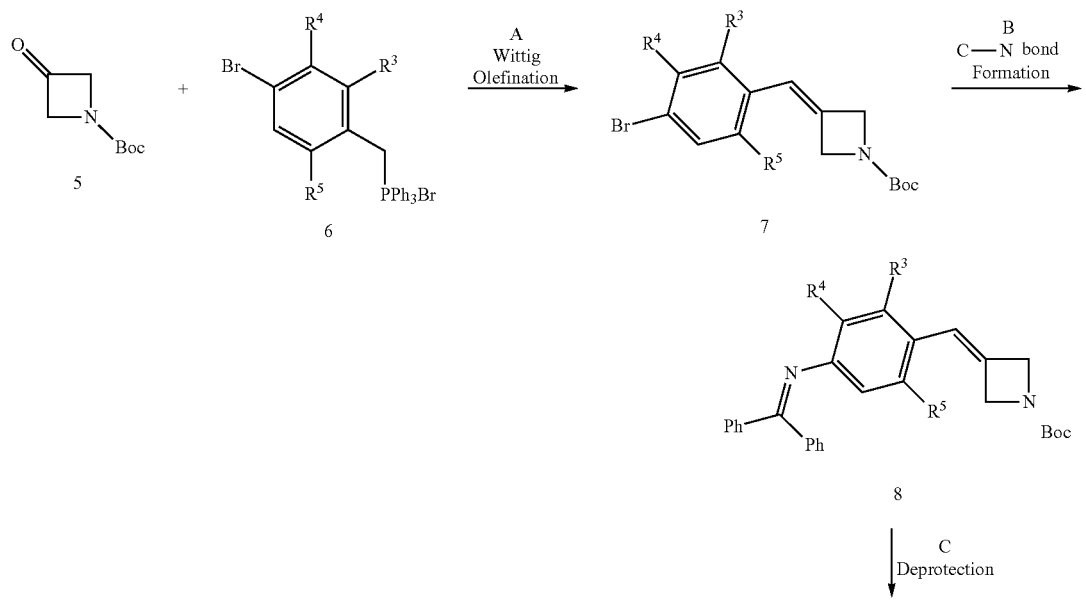

-continued

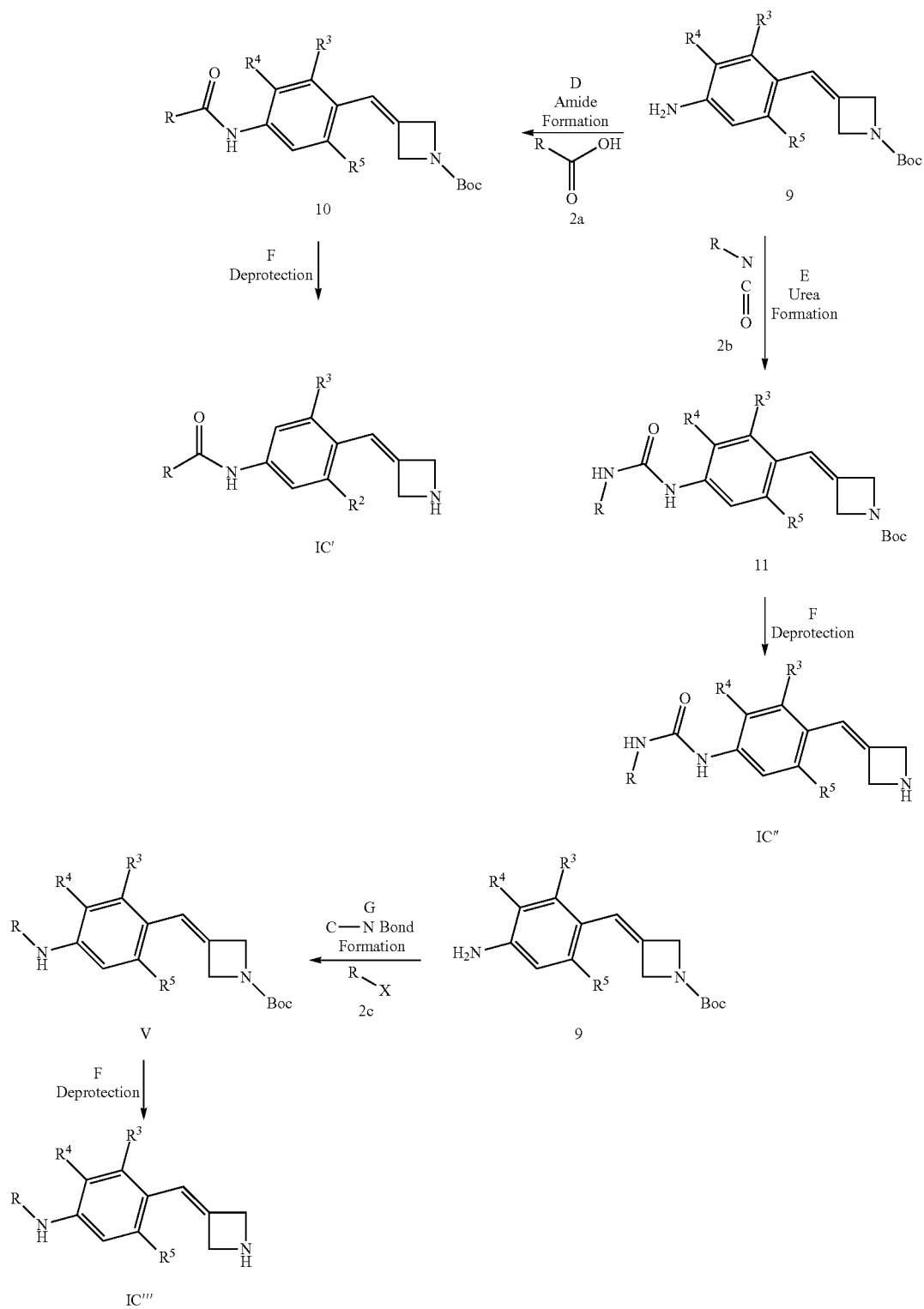

wherein R is phenyl optionally substituted by one or more substituents, selected from halogen, lower alkyl substituted by halogen or lower alkoxy, or is a five or six membered heteroaryl, selected from pyridinyl, pyrimidinyl, pyrazinyl, pyridazinyl or pyrazolyl, which heteroaryls are optionally substituted by one or more substituents, selected from halogen, lower alkyl, lower alkoxy, cyano, cycloalkyl, lower alkyl substituted by halogen, lower alkoxy substituted by halogen or by phenyl substituted by halogen, and wherein the substituents $R^3$, $R^4$ and $R^5$ and are as described above; X is halogen.

Step A:

A Wittig olefination reaction between commercially available azetidine 5 [CAS 398489-26-4] and triphenylphosphonium salt 6 [CAS 51044-13-4] can be accomplished in the presence of a base such as KO$^t$Bu, NaO$^t$Bu, NaH, KHMDS, NaHMDS in solvents such as 1,4-dioxane, DME, THF, DMF and DMSO.

Preferred conditions are sodium hydride in DMF at 0-65° C. for 16 hours.

Step B:

C—N bond formation can be accomplished by treatment of 7 with benzophenone imine in the presence of a palladium or copper catalyst, a ligand and a base in solvents such as dioxane, DME, THF, toluene, DMF and DMSO at elevated temperatures, for instance using a palladium-catalysed Buchwald-Hartwig reaction.

Preferred conditions are catalytic tris(dibenzylidineacetone)dipalladium(0), catalytic rac-2,2'-bis(diphenylphosphino)-1,1'-binaphthyl and sodium tert-butoxide in toluene at 100° C. for 3 hour.

Step C:

Removal of N-diphenylmethylene group can be accomplished by treatment with hydroxylamine hydrochloride, together with as base such as sodium acetate, potassium acetate, sodium carbonate, potassium carbonate, cesium carbonate in solvents such as MeOH, EtOH, dioxane, THF, DMF or mixture thereof.

Preferred conditions are hydroxylamine hydrochloride, together with sodium acetate, in MeOH at 50° C. for 16 hour.

Step D:

Amide formation can be accomplished by a coupling reaction between aniline 9 and a carboxylic acid 2a with a coupling reagent such as DCC, EDC, TBTU, HBTU or HATU in the presence of an organic base such as triethylamine, N,N-diisopropylethylamine or N-methylmorpholine in solvents such as dichloromethane, 1,2-dichloroethane, DMF, DMSO, or ethereal solvents including diethyl ether, 1,4-dioxane, THF, DME, or TBME.

Preferred conditions are HBTU with N-methylmorpholine in DMF at room temperature for 16 hours.

Step E:

Urea formation can be accomplished by a coupling reaction between aniline 9 and an isocyanate 2b, optionally in the presence of an organic base such as triethylamine, N,N-diisopropylethylamine or N-methylmorpholine in halogenated solvents such as dichloromethane, 1,2-dichloroethane, chlorobenzene or protic solvents such as DMF, NMP, DMA or ethereal solvents such as diethyl ether, 1,4-dioxane, THF, DME or TBME.

Preferred conditions are in absence of base in THF at 30-60° C. for 16-24 hours.

Step F:

Removal of the N-Boc protecting group can be effected with mineral acids such as HCl, $H_2SO_4$ or $H_3PO_4$ or organic acids such as $CF_3COOH$, $CHCl_2COOH$, HOAc or p-toluenesulfonic acid in solvents such as $CH_2Cl_2$, $CHCl_3$, THF, MeOH, EtOH or $H_2O$ at 0-80° C.

Preferred conditions are $CF_3COOH$ in $CH_2Cl_2$ at room temperature for 2 hours.

Step G:

Coupling reaction between aryl halide 2c and aniline 9 can be accomplished by using a palladium or copper catalyst, a ligand, and a base in solvents such as 1,4-dioxane, diglyme, DMF, THF, toluene, DMF and DMSO at elevated temperatures, for instance using a palladium-catalysed Buchwald-Hartwig reaction.

Preferred conditions are catalytic tris(dibenzylidineacetone)dipalladium(0), catalytic 4,5-Bis(diphenylphosphino)-9,9-dimethylxanthene (Xantphos), $Cs_2CO_3$ in 1,4-dioxane at 95° C. for 16 hours.

Scheme 3

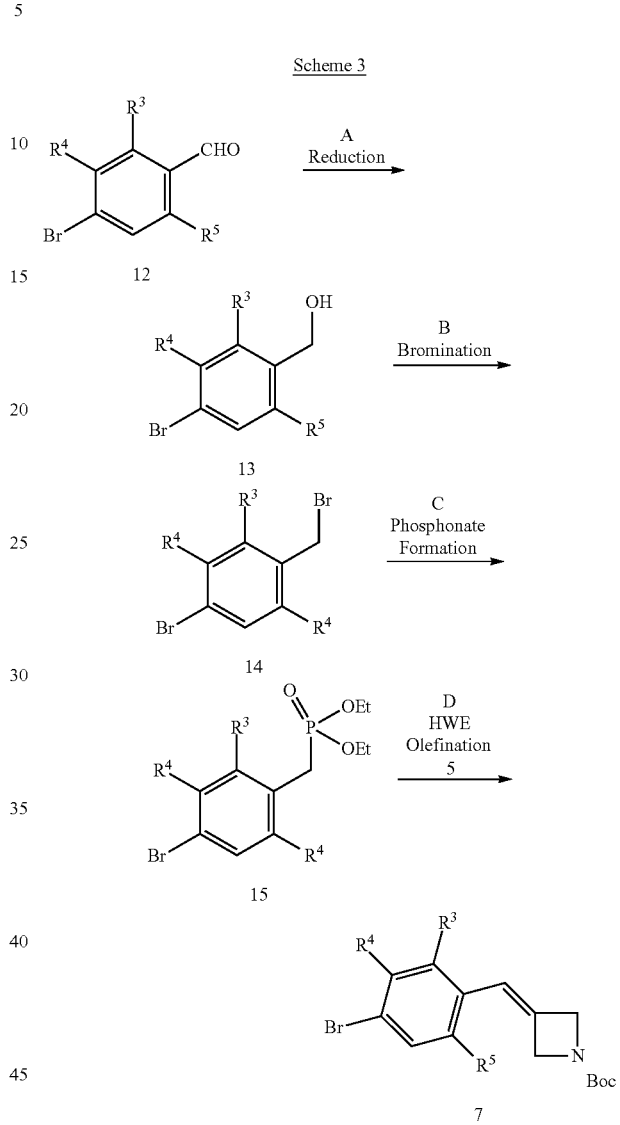

Step A:

Commercially available aldehyde 12 can be treated with a reducing agent such as $NaBH_4$ or $LiBH_4$ in a solvent such as MeOH, EtOH, THF, dioxane, dichloromethane or mixture thereof.

Preferred conditions are $NaBH_4$ in a 4:1 mixture of dichloromethane and methanol at 0° C. to room temperature for 1 hour.

Step B:

Conversion of alcohol 13 to benzyl bromide 14 can be accomplished by treatment with halogenating reagents such as bromine, $PBr_3$, $Ph_3PBr_2$, $Ph_3P$ and carbon tetrabromide, in solvents such as $CH_2Cl_2$, $CHCl_3$, benzene, or toluene, at 0° C. to elevated temperatures.

Preferred conditions are triphenylphosphine and carbon tetrabromide in $CH_2Cl_2$ at 0° C. to room temperature for 2 hours.

Step C:

Phosphonate formation can be accomplished by a reaction between benzyl bromide 14 and triethyl phosphite [CAS 122-52-1] in halogenated solvents such as dichloromethane, 1,2-dichloroethane, chlorobenzene or protic solvents such as DMF, NMP, DMA or ethereal solvents such as diethyl ether, 1,4-dioxane, THF, DME or TBME.

Preferred conditions are in absence of solvent at elevated temperature for 2 hours.

Step D:

A Horner-Wadsworth-Emmons (HWE) reaction between commercially available azetidine 5 [CAS 398489-26-4] and phosphonate 15 can be accomplished in the presence of a base such as KO$^t$Bu, NaO$^t$Bu, NaH, KHMDS, NaHMDS, LDA in solvents such as 1,4-dioxane, DME, THF, DMF and DMSO.

Preferred conditions are LDA in THF at −78° C. to room temperature for 1 hour.

The compounds of formula 7 may further be transformed in accordance with scheme 2.

Scheme 4

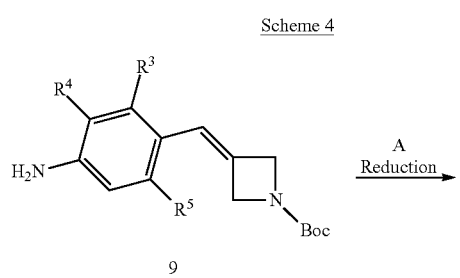

9

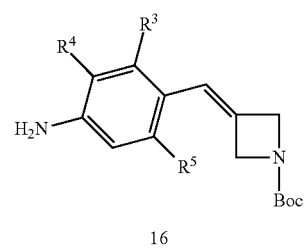

16

Wherein the substituents $R^3$, $R^4$, $R^5$ are described above;

Step A:

Reduction of alkene 9 can be effected by hydrogenation reaction with hydrogen under normal or elevated pressure or by transfer hydrogenation using ammonium formate or cyclohexadiene as hydrogen source in the presence of a palladium catalyst in solvents such as MeOH, EtOH, H$_2$O, dioxane, THF, HOAc, EtOAc, DMF or mixtures thereof.

Preferred conditions are palladium on charcoal in MeOH at room temperature and 1 atm H$_2$ for 4 hours.

The compounds of formula 16 may further be transformed in accordance with scheme 2.

Scheme 5

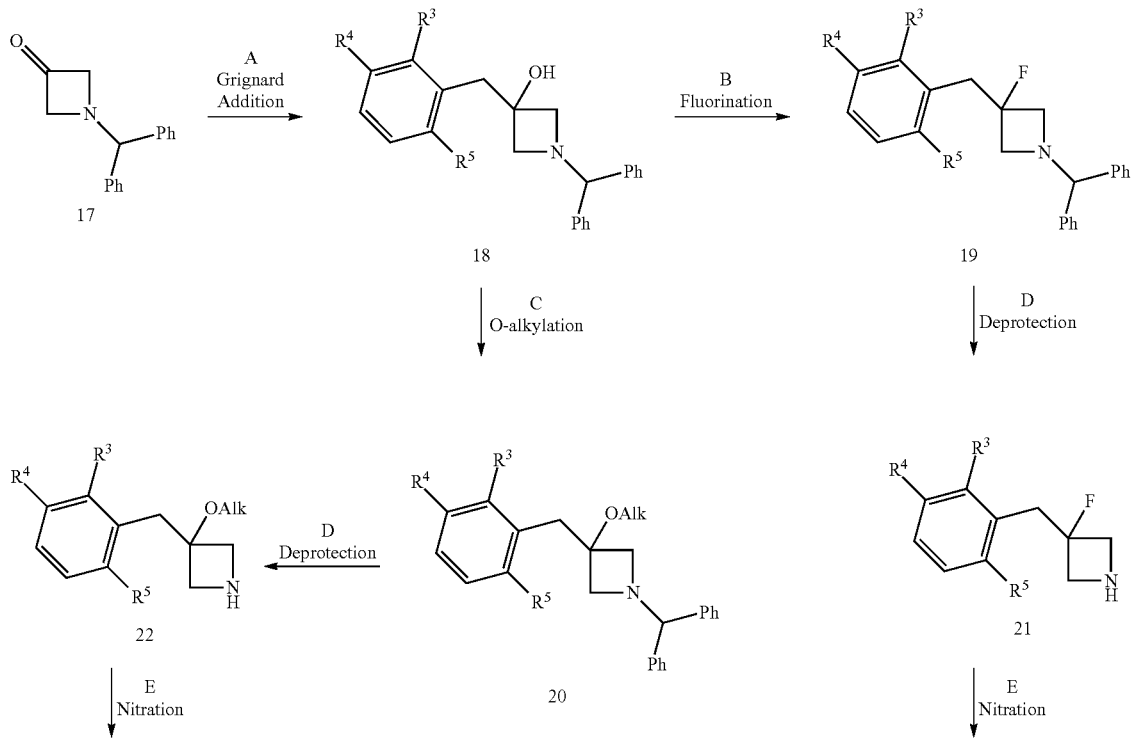

-continued

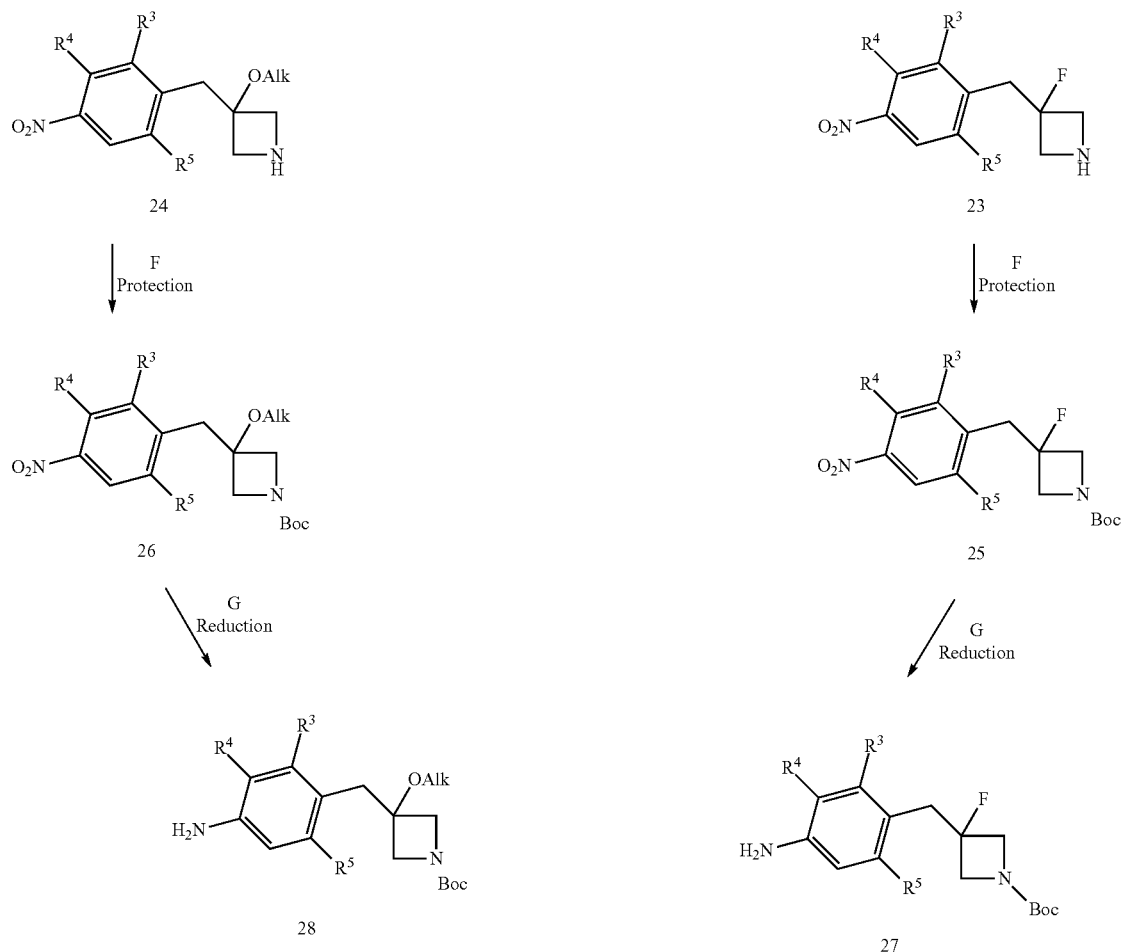

Wherein the substituents $R^3$, $R^4$, $R^5$ are described above and Alk is lower alkyl.

Step A:

Grignard addition of benzyl magnesium chloride to ketone 17 [CAS 40320-60-3] can be accomplished in ethereal solvents such as diethyl ether, 1,4-dioxane, THF, DME, or TBME at low temperatures.

Preferred conditions are in THF at −78° C. to room temperature for 16 hours.

Step B:

Conversion of tertiary alcohol 18 to the corresponding organofluorine compound 19 can be performed by treatment with fluorinating agents such as diethylaminosulfur trifluoride (DAST), morpholinosulfur trifluoride, 2,2-difluoro-1,3-dimethylimidazolidine, bis(2-methoxyethyl)aminosulfur trifluoride (Deoxo-Fluor™), $Et_3N(HF)_3$ in combination with PBSF, in solvents such as THF, DME, DCE or dichloromethane.

Preferred conditions are using Deoxo-Fluor™ in dichloromethane at −78° C. to room temperature for 1 hour.

Step C:

O-alkylation reaction of tertiary alcohol 18 to the corresponding ether 20 can be performed in presence of a base such as KO$^t$Bu, NaO$^t$Bu, NaH, KHMDS, NaHMDS, LDA in solvents such as 1,4-dioxane, DME, THF, DMF and DMSO by treatment with an alkylating agents such as methyl iodide, ethyl iodide.

Preferred conditions are NaH in THF at 0° C. to room temperature for 16 hours.

Step D:

Cleavage of N-benzhydryl protecting group in 19 and 20 can be accomplished by either a hydrogenation reaction catalyzed by a Pd catalyst or treatment with chloroformates such as $ClC(O)OCH_2CH_2Cl$, $ClC(O)OCH(Cl)Me$, $ClC(O)OCH_2Ph$, and $ClC(O)OCH_2CCl_3$, and optionally with an base such as triethylamine, diisopropylethylamine, and sodium hydroxide, in solvents such as dichloromethane, 1,2-dichloroethane, toluene, THF, diethylether, dioxane, TBME, methanol, and ethanol, at room temperature to elevated temperatures.

Preferred conditions are using palladium on charcoal in MeOH in presence of a stoichiometric amount of aqueous hydrochloride at room temperature and 1 atm $H_2$ for 16 hours.

Step E:

Regioselective nitration of the phenyl ring in 21 and 22 can be effected by treatment with a mixture of nitric acid and sulfuric acid, optionally in the presence of a co-solvent such as dichloromethane.

Preferred conditions are using stoichiometric amount of nitric acid in a 2:1 mixture of sulfuric acid and dichloromethane at −20° C. to 0° C. for 1 hour.

Step F:

Protection of the secondary amino group in 23 and 24 can be effected by treatment with di-tert-butyl carbonate, optionally in the presence of an organic base such as triethylamine, N,N-diisopropylethylamine or N-methylmorpholine, in halogenated solvents such as dichloromethane or 1,2-dichloroethane or ethereal solvents such as diethyl ether, dioxane, THF or TBME or protic solvents such as MeOH, EtOH.

of a catalyst such as $PtO_2$, Pd—C or Raney nickel in solvents such as MeOH, EtOH, $H_2O$, dioxane, THF, HOAc, EtOAc, DMF or mixtures thereof.

Preferred conditions are palladium on charcoal in EtOAc at room temperature and 1 atm $H_2$ for 16 hours.

Compounds of formulas 27 and 28 may be further transformed into compounds of formula IB-1 according to scheme 2.

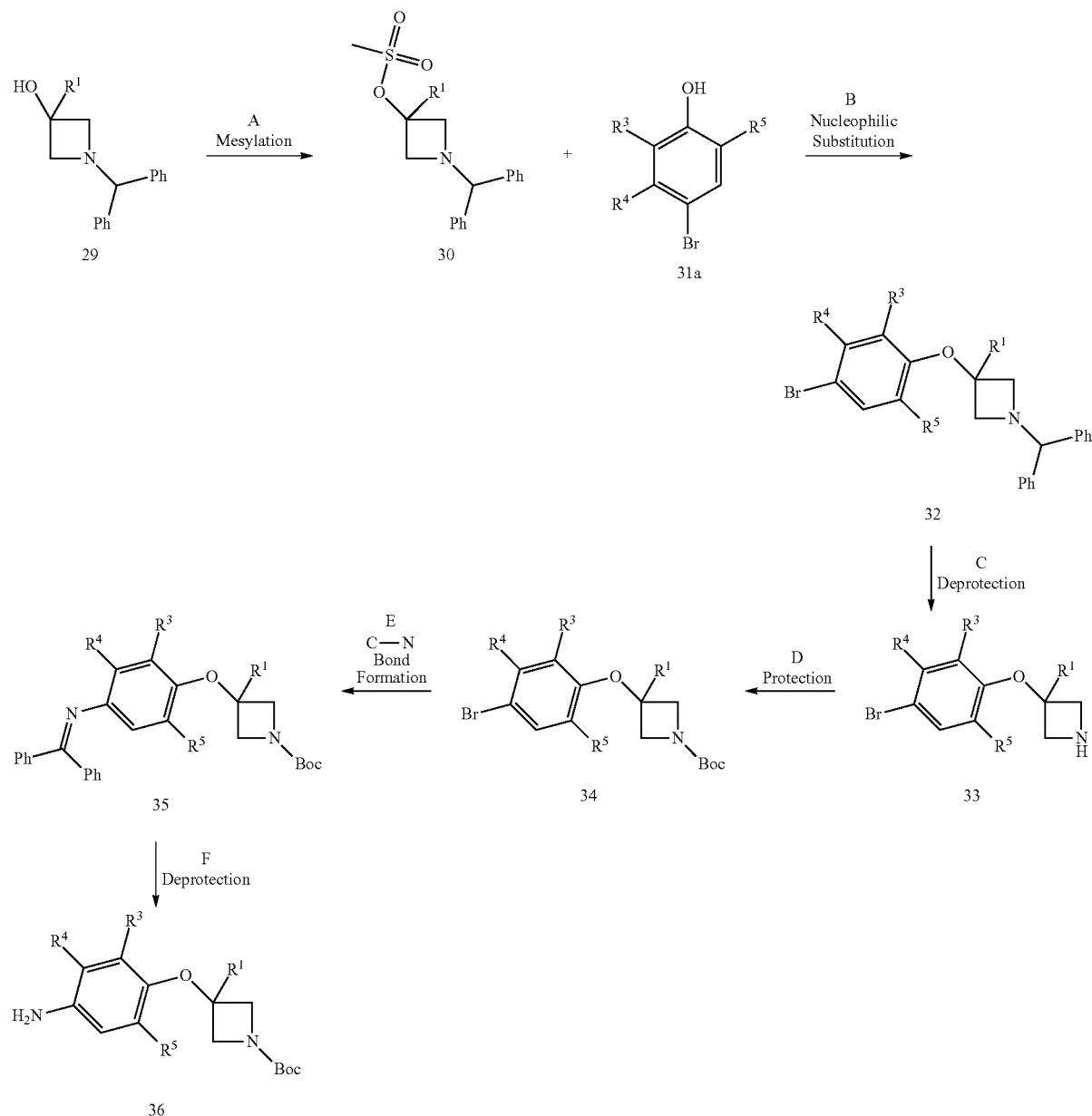

Scheme 6

Preferred conditions are using N,N-diisopropylethylamine in MeOH at room temperature for 16 hours.

Step G:

Reduction of the nitro group of 25 and 26 to aniline 27 and 28, respectively, can be effected by hydrogenation with hydrogen under normal or elevated pressure in the presence Wherein the substituents $R^1$, $R^3$, $R^4$ and $R^5$ are as described above.

Step A:

Sulphonate ester formation can be accomplished by treatment of secondary alcohol 29 [CAS 18621-17-5] with methanesulfonyl chloride in the presence of an organic base such as triethylamine, N,N-diisopropylethylamine or N-methylmorpholine in ethereal solvents such as diethyl ether, dioxane, THF or TBME or halogenated solvents such as dichloromethane, DCE, chlorobenzene or chloroform.

Preferred conditions are triethylamine in dichloromethane at −20° C. to room temperature for 16 hours.

Step B:

Nucleophilic substitution reaction between mesylate 30 and a phenol 31a can be promoted by a base such as KO$^t$Bu, NaO$^t$Bu, NaH, KHMDS, $K_2CO_3$, $Cs_2CO_3$, NaHMDS, LDA in solvents such as 1,4-dioxane, DME, THF, DMF or DMSO.

Preferred conditions are NaH in DMF at 0-80° C. for 16 hours.

Step C:

Cleavage of N-benzhydryl protecting group in 32 can be accomplished by treatment with chloroformates such as ClC(O)OCH$_2$CH$_2$Cl, ClC(O)OCH(Cl)Me, ClC(O)OCH$_2$Ph, and ClC(O)OCH$_2$CCl$_3$, and optionally with an base such as triethylamine, diisopropylethylamine, and sodium hydroxide, in solvents such as dichloromethane, 1,2-dichloroethane, toluene, THF, diethylether, dioxane or TBME followed by treatment with methanol or ethanol, at room temperature to elevated temperatures.

Preferred conditions are ClC(O)OCH(Cl)Me in 1,2-dichloroethane in absence of a base followed by treatment with MeOH at reflux for 1-2 hours.

Step D:

Protection of the secondary amino group in 33 can be effected by treatment with di-tert-butyl carbonate, optionally in the presence of an organic base such as triethylamine, N,N-diisopropylethylamine or N-methylmorpholine, in halogenated solvents such as dichloromethane or 1,2-dichloroethane or ethereal solvents such as diethyl ether, dioxane, THF or TBME or protic solvents such as MeOH, EtOH.

Preferred conditions are using N,N-diisopropylethylamine in MeOH at room temperature for 16 hours.

Step E:

C—N bond formation can be accomplished by treatment of an aryl bromide 34 with benzophenone imine in the presence of a palladium or copper catalyst, a ligand and a base in solvents such as dioxane, DME, THF, toluene, DMF and DMSO at elevated temperatures, for instance using a palladium-catalysed Buchwald-Hartwig reaction.

Preferred conditions are catalytic tris(dibenzylidineacetone)dipalladium(0), catalytic rac-2,2'-bis(diphenylphosphino)-1,1'-binaphthyl and sodium tert-butoxide in toluene at 90° C. for 16 hour.

Step F:

Removal of N-diphenylmethylene group can be accomplished by hydrogenation with hydrogen under normal or elevated pressure or by transfer hydrogenation using ammonium formate or cyclohexadiene as hydrogen source with a catalyst such as PtO$_2$, Pd—C or Raney nickel in solvents such as MeOH, EtOH, H$_2$O, 1,4-dioxane, THF, EtOAc, dichloromethane, chloroform, DMF or mixture thereof.

The transformation can also be effected by treatment with hydroxylamine hydrochloride, together with a base such as sodium acetate, potassium acetate, sodium carbonate, potassium carbonate, cesium carbonate in solvents such as MeOH, EtOH, 1,4-dioxane, THF, DMF or mixture thereof.

Preferred conditions are hydroxylamine hydrochloride, together with sodium acetate, in MeOH at 50° C. for 16 hour.

The compound of formula 36 may further transformed to a compound of formula IB-3 according to scheme 2.

Scheme 7

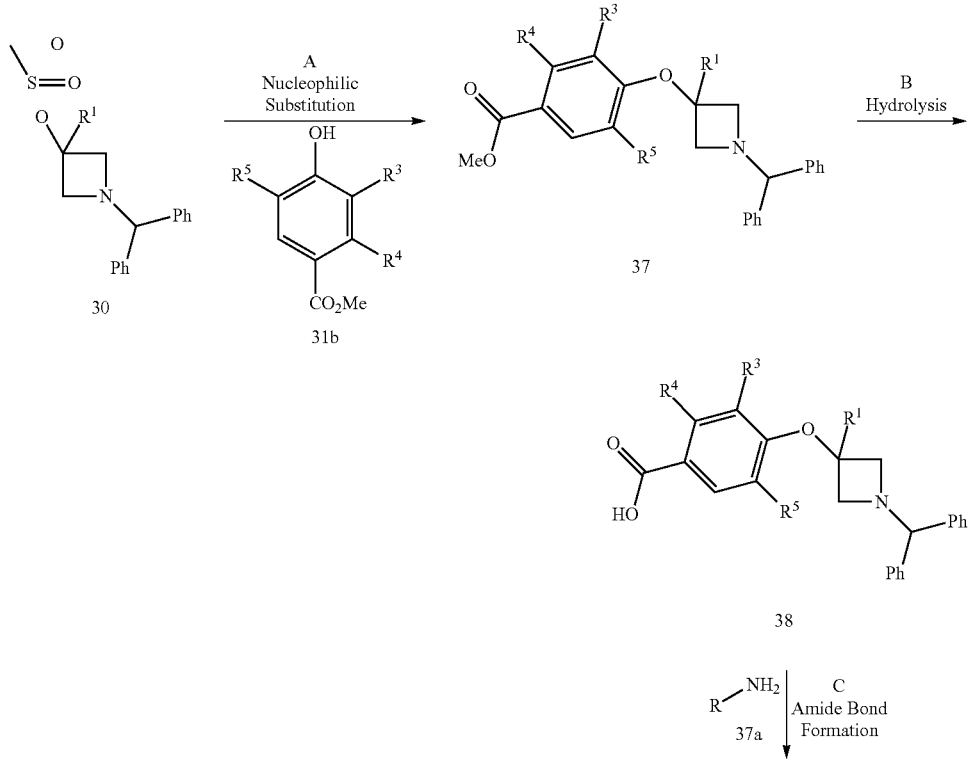

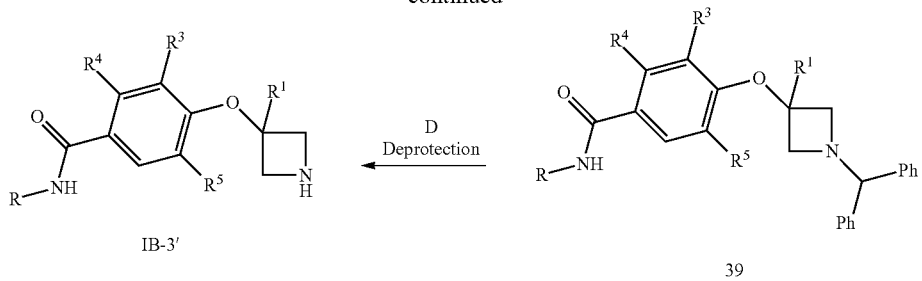

IB-3′     D Deprotection     39 wherein the substituents R, $R^3$, $R^4$ and $R^5$ are as described above.

Step A:

Nucleophilic substitution reaction between mesylate 30 and a phenol 31b can be promoted by a base such as KO$^t$Bu, NaO$^t$Bu, NaH, KHMDS, K$_2$CO$_3$, Cs$_2$CO$_3$, NaHMDS, LDA in solvents such as 1,4-dioxane, DME, THF, DMF or DMSO.

Preferred conditions are NaH in DMF at 0-80° C. for 16 hours.

Step B:

Hydrolysis of methyl ester 37 to carboxylic acid 38 can be performed under basic conditions in presence of water. Typical conditions involved treatment with an inorganic base such as LiOH, NaOH, KOH, K$_2$CO$_3$ in a mixture of an organic solvent such as MeOH, EtOH, THF, CH$_3$CN, DMF, DMSO and water at room temperature to elevated temperatures.

Preferred conditions are LiOH in a 2:1 mixture of MeOH and water at 45° C. for 4 hours.

Step C:

Amide formation can be accomplished by a coupling reaction between carboxylic acid 38 and an amine 37a with a coupling reagent such as DCC, EDC, TBTU, HBTU or HATU in the presence of an organic base such as triethylamine, N,N-diisopropylethylamine or N-methylmorpholine in solvents such as dichloromethane, 1,2-dichloroethane, DMF, DMSO, or ethereal solvents including diethyl ether, 1,4-dioxane, THF, DME, or TBME.

Preferred conditions are HBTU with N-methylmorpholine in DMF at room temperature for 16 hours.

Step D:

Cleavage of N-benzhydryl protecting group in 39 can be accomplished by either a hydrogenation reaction catalyzed by a Pd catalyst or treatment with chloroformates such as ClC(O)OCH$_2$CH$_2$Cl, ClC(O)OCH(Cl)Me, ClC(O)OCH$_2$Ph, and ClC(O)OCH$_2$CCl$_3$, and optionally with an base such as triethylamine, diisopropylethylamine, and sodium hydroxide, in solvents such as dichloromethane, 1,2-dichloroethane, toluene, THF, diethylether, dioxane, TBME, methanol, and ethanol, at room temperature to elevated temperatures.

Preferred conditions are using palladium on charcoal in MeOH in presence of a stoichiometric amount of aqueous hydrochloride at room temperature and 1 atm H$_2$ for 16 hours.

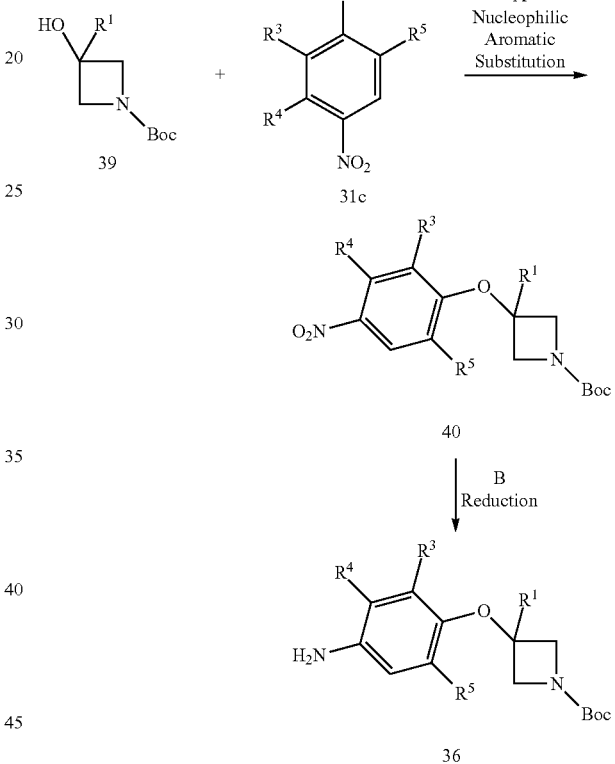

Scheme 8 wherein the substituents $R^1$, $R^3$, $R^4$ and $R^5$ are as described above.

Step A:

An alternative synthesis of compounds of general formula I-c is described in scheme 8. Nucleophilic aromatic substitution between secondary alcohol 39 [CAS 141699-55-0] and an aryl fluoride 31c can be performed by treatment with a base such as KO$^t$Bu, NaO$^t$Bu, NaH, KHMDS, NaHMDS, LDA in solvents such as 1,4-dioxane, DME, THF, DMF or DMSO.

Preferred conditions are KHMDS in THF at 0° C. to room temperature for 2 hours.

Step B:

Reduction of the nitro group of 40 to aniline 36 can be effected by hydrogenation reaction with hydrogen under normal or elevated pressure in the presence of a catalyst such as PtO$_2$, Pd—C or Raney nickel in solvents such as MeOH, EtOH, H$_2$O, dioxane, THF, HOAc, EtOAc, DMF or mixtures thereof.

Preferred conditions are palladium on charcoal in EtOAc at room temperature and 1 atm H$_2$ for 16 hours.

The compounds of formula 36 may be transformed to compounds of formula IB-3 as described in scheme 2.

Scheme 9

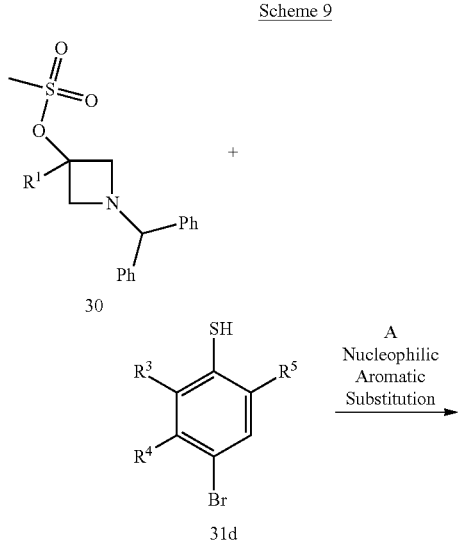

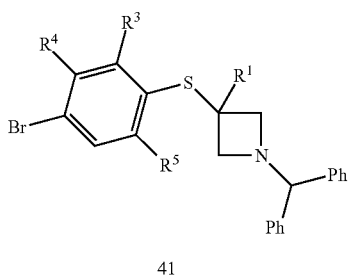

wherein the substituents R$^1$, R$^3$, R$^4$ and R$^5$ are as described above.

Step A:

In a similar fashion to the synthesis of compounds IB-3 described in scheme 6, compounds of general formula IIB-4 can be prepared by a nucleophilic substitution reaction between mesylate 30 and a thiol 31d in presence of a base such as KO$^t$Bu, NaO$^t$Bu, NaH, KHMDS, K$_2$CO$_3$, Cs$_2$CO$_3$, NaHMDS, LDA in solvents such as 1,4-dioxane, DME, THF, DMF or DMSO, as described in scheme 2.

Preferred conditions are NaH in DMF at 0-60° C. for 16 hours.

Scheme 10

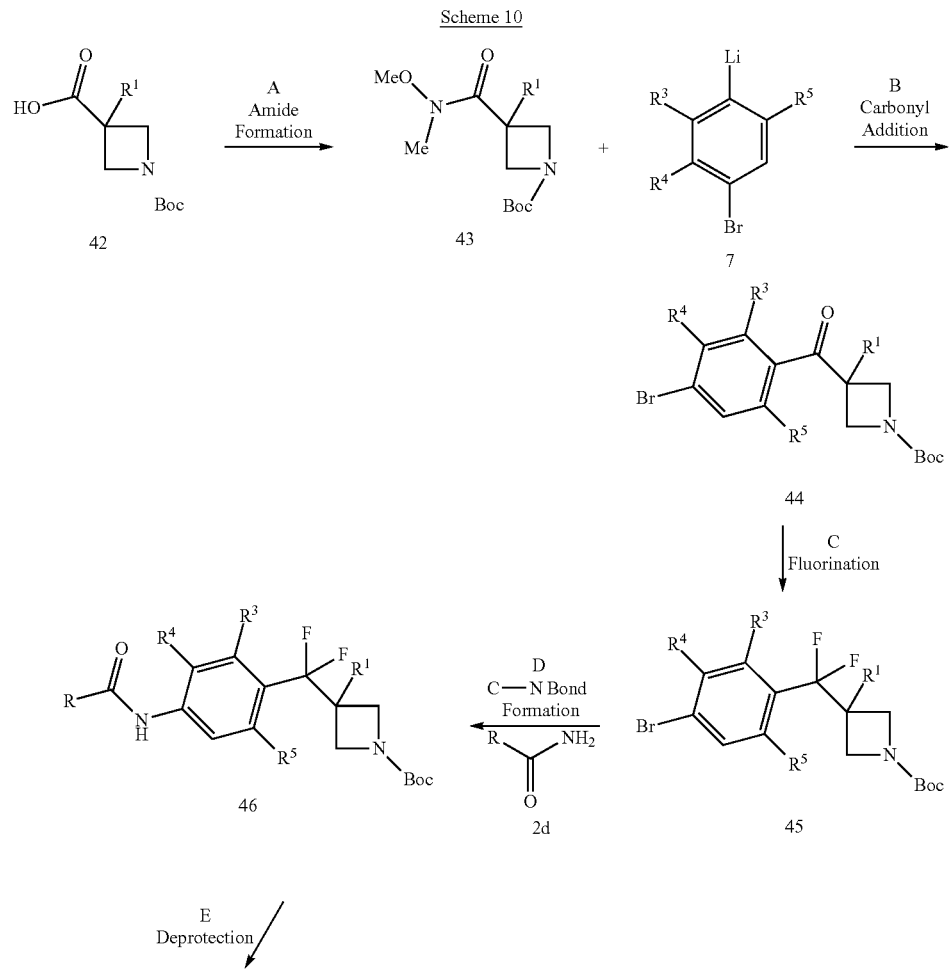

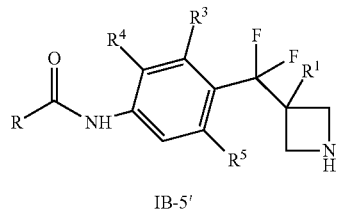

IB-5' wherein the substituent $R^1$, $R^3$, $R^4$, $R^5$ are described above and R is phenyl optionally substituted by one or more substituents, selected from halogen, lower alkyl substituted by halogen or lower alkoxy, or is a five or six membered heteroaryl, selected from pyridinyl, pyrimidinyl, pyrazinyl, pyridazinyl or pyrazolyl, which heteroaryls are optionally substituted by one or more substituents, selected from halogen, lower alkyl, lower alkoxy, cyano, cycloalkyl, lower alkyl substituted by halogen, lower alkoxy substituted by halogen or by phenyl substituted by halogen;

Step A:

Amide coupling between commercially available azetidine 42 [CAS 142253-55-2] and N,O-dimethylhydroxylamine hydrochloride can be accomplished with a coupling reagent such as DCC, EDC, TBTU, HBTU or HATU in the presence of an organic base such as triethylamine, N,N-diisopropylethylamine or N-methylmorpholine in solvents such as dichloromethane, 1,2-dichloroethane, DMF, DMSO, or ethereal solvents including diethyl ether, 1,4-dioxane, THF, DME, or TBME.

Preferred conditions are HBTU with N-methylmorpholine in DMF at room temperature for 16 hours.

Step B:

Ketone 44 can be obtained by a stepwise process involving aryl lithium intermediates. 1,4-dibromobenzene can be converted to the corresponding (4-bromophenyl)lithium by reaction with butyllithium in ethereal solvents such as diethyl ether, 1,4-dioxane, THF, DME, or TBME at low temperatures.

Preferred conditions are in THF at −78° C. to −25° C. for 30 minutes.

In the second step, addition of (4-bromophenyl)lithium to Weinreb amide 43 in ethereal solvents such as diethyl ether, 1,4-dioxane, THF, DME, or TBME at low temperatures delivered the desired ketone 44.

Preferred conditions are in THF at −78° C. for 90 minutes followed by warm up to −25° C. for 4 hours.

Step C:

Fluorination of ketone 44 to the corresponding gem-difluoro derivative 45 can be performed by treatment with fluorinating agents such as diethylaminosulfur trifluoride (DAST), morpholinosulfur trifluoride, 2,2-difluoro-1,3-dimethylimidazolidine, bis(2-methoxyethyl) aminosulfur trifluoride (Deoxo-Fluor™), $Et_3N(HF)_3$ in combination with PBSF, in solvents such as THF, DME, DCE or dichloromethane.

Preferred conditions are using Deoxo-Fluor™ in dichloromethane at room temperature for 5 days.

Step D:

Coupling reaction between aryl bromide 45 and a primary amide of general formula 2d can be accomplished by using a palladium catalyst, a ligand, and a base in solvents such as 1,4-dioxane, diglyme, DMF, THF, toluene, DMF and DMSO at elevated temperatures, for instance using a palladium-catalysed Buchwald-Hartwig reaction.

Preferred conditions are catalytic tris(dibenzylidineacetone)dipalladium(0), catalytic 4,5-Bis(diphenylphosphino)-9,9-dimethylxanthene (Xantphos), $K_3PO_4$ in 1,4-dioxane at 100° C. for 16 hours.

Step E:

Removal of N-Boc protecting group can be effected with mineral acids such as HCl, $H_2SO_4$, or $H_3PO_4$ or organic acids such as $CF_3COOH$, $CHCl_2COOH$, HOAc or p-toluenesulfonic acid in solvents such as $CH_2Cl_2$, $CHCl_3$, THF, MeOH, EtOH, or $H_2O$ at 0-80° C.

Preferred conditions are using $CF_3COOH$ in $CH_2Cl_2$ at room temperature for 2 hour.

Scheme 11

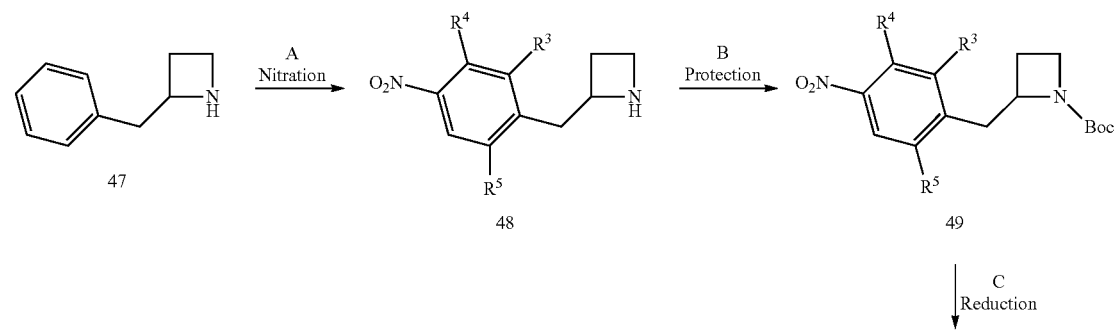

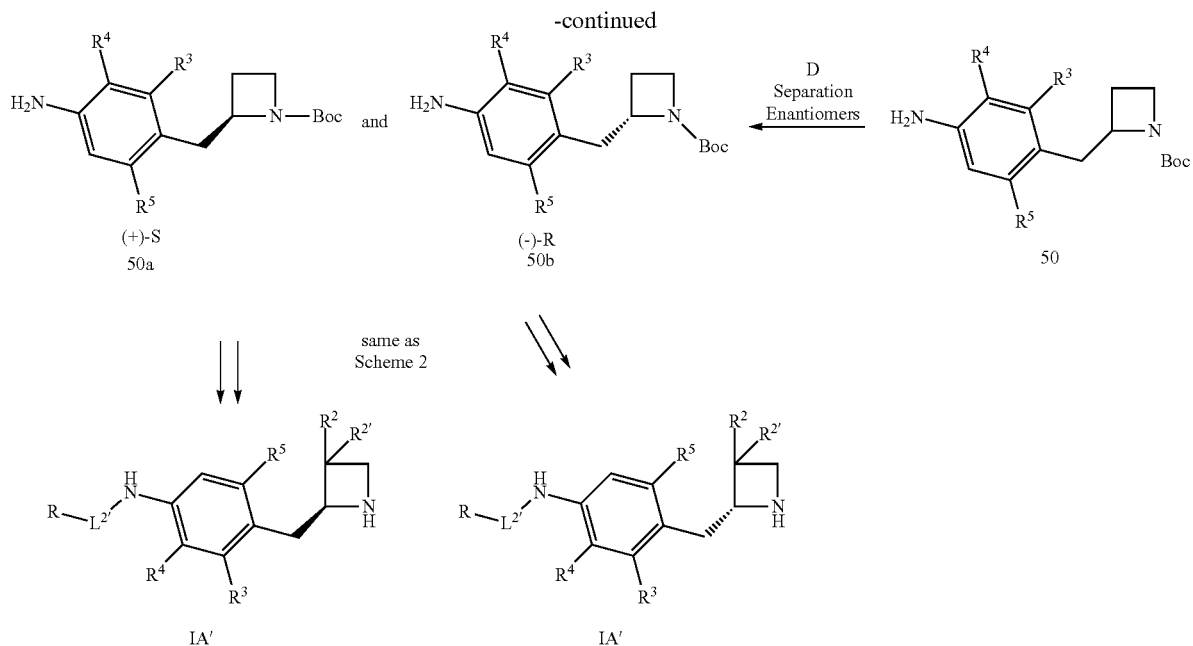

wherein the substituents R, $R^2$, $R^{2'}$, $R^3$, $R^4$ are as described above, and the definition $L^2$ is a bond or —NHC(O)— and R is phenyl optionally substituted by one or more substituents, selected from halogen, lower alkyl substituted by halogen or lower alkoxy, or is a five or six membered heteroaryl, selected from pyridinyl, pyrimidinyl, pyrazinyl, pyridazinyl or pyrazolyl, which heteroaryls are optionally substituted by one or more substituents, selected from halogen, lower alkyl, lower alkoxy, cyano, cycloalkyl, lower alkyl substituted by halogen, lower alkoxy substituted by halogen or by phenyl substituted by halogen;

Step A:

Regioselective aromatic nitration of commercially available azetidine 2-benzylazetidine 47 can be effected by treatment with a mixture of nitric acid and sulfuric acid, optionally in the presence of a co-solvent such as dichloromethane.

Preferred conditions are using stoichiometric amount of nitric acid in a 2:1 mixture of sulfuric acid and dichloromethane at −20° C. to 0° C. for 1 hour.

Step B:

Protection of the secondary amino group in 48 can be effected by treatment with di-tert-butyl carbonate, optionally in the presence of an organic base such as triethylamine, N,N-diisopropylethylamine or N-methylmorpholine, in halogenated solvents such as dichloromethane or 1,2-dichloroethane or ethereal solvents such as diethyl ether, dioxane, THF or TBME or protic solvents such as MeOH, EtOH.

Preferred conditions are using N,N-diisopropylethylamine in MeOH at room temperature for 16 hours.

Step C:

Reduction of the nitro group in 49 to the corresponding aniline 50 can be effected by hydrogenation with hydrogen under normal or elevated pressure in the presence of a catalyst such as $PtO_2$, Pd—C or Raney nickel in solvents such as MeOH, EtOH, $H_2O$, dioxane, THF, HOAc, EtOAc, DMF or mixtures thereof.

Preferred conditions are palladium on charcoal in EtOAc at room temperature and 1 atm $H_2$ for 16 hours.

Step D:

Enantiomers of 50 (50a and 50b) can be separated using chiral HPLC or SFC. Preferred conditions are using HPLC (column: Reprosil Chiral-NR, 250×50 mm; eluent: 10% ethanol/heptane; pressure: 18 bar; flow rate: 35 mL/min)

In detail, the compounds of formula IA may be prepared in accordance with example 90.

Scheme 12

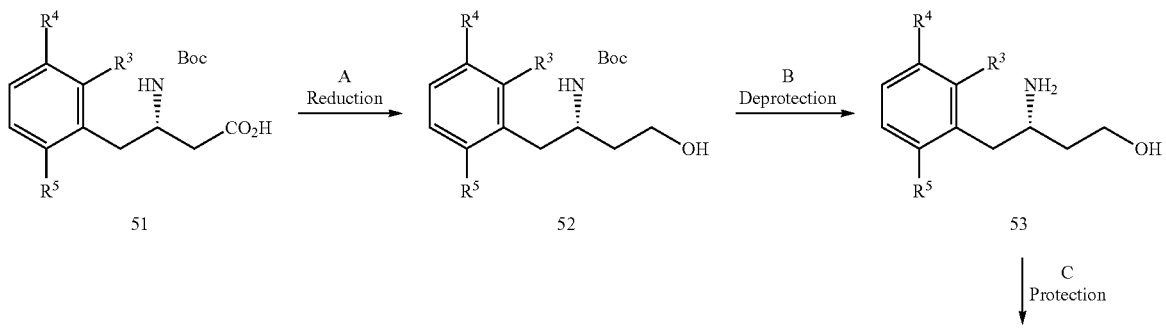

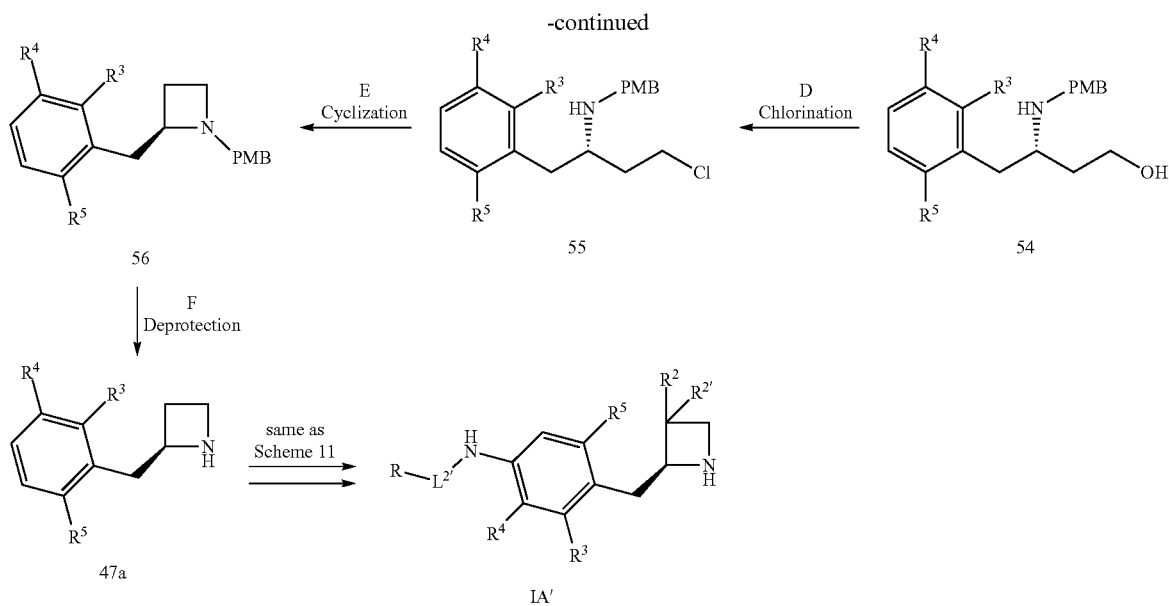

wherein the substituents $R^5$, $R^2$, $R^{2'}$, $R^3$, $R^4$ are as described above, and the definition $L^{2'}$ is a bond or —NHC(O)— and R is phenyl optionally substituted by one or more substituents, selected from halogen, lower alkyl substituted by halogen or lower alkoxy, or is a five or six membered heteroaryl, selected from pyridinyl, pyrimidinyl, pyrazinyl, pyridazinyl or pyrazolyl, which heteroaryls are optionally substituted by one or more substituents, selected from halogen, lower alkyl, lower alkoxy, cyano, cycloalkyl, lower alkyl substituted by halogen, lower alkoxy substituted by halogen or by phenyl substituted by halogen;

Step A:

An alternative asymmetric synthesis of compounds of general formula III is described in scheme 12. Reduction of the commercially available chiral carboxylic acid 51 [CAS 51871-62-6] to alcohol 52 can be accomplished by a stepwise process involving a mixed anhydride formation by treatment of 51 with methyl chloroformate or ethyl chloroformate in presence of a base such as triethylamine, N,N-diisopropylethylamine or N-methylmorpholine, in ethereal solvents such as diethyl ether, dioxane, THF or TBME, followed by reduction with $NaBH_4$ or $LiBH_4$ in a solvent such as MeOH, EtOH, THF, dioxane, dichloromethane, water or mixture thereof.

Preferred conditions are methyl chloroformate, N-methylmorpholine in THF at 0° C. for 2 hour followed by reduction with $NaBH_4$ in water at 0° C. to room temperature for 1 hour.

Step B:

Removal of the N-Boc protecting group can be effected with mineral acids such as HCl, $H_2SO_4$ or $H_3PO_4$ or organic acids such as $CF_3COOH$, $CHCl_2COOH$, HOAc or p-toluenesulfonic acid in solvents such as $CH_2Cl_2$, $CHCl_3$, THF, MeOH, EtOH or $H_2O$ at 0-80° C.

Preferred conditions are 4.0 M HCl in 1,4-dioxane at 60° C. for 2 hours then allowed to cool to room temperature for 16 hours.

Step C:

N-4-methoxybenzyl protection of primary amine 53 can be accomplished by a stepwise process involving imine formation between 4-methoxybenzaldehyde [CAS 123-11-5] and 53 in presence of a base such as triethylamine, N,N-diisopropylethylamine or N-methylmorpholine, in solvents such as MeOH, EtOH, dichloromethane, toluene, trimethyl orthoformate, followed by reduction with $NaBH_3CN$, $NaBH(OAc)_3$, $NaBH_4$ or $LiBH_4$.

Preferred conditions are N,N-diisopropylethylamine, in MeOH at room temperature for 16 hours followed by reduction with $NaBH_4$ at room temperature for 1 hour.

Step D:

Conversion of alcohol 54 to chloride 55 can be accomplished by treatment with chlorinating reagents such as $(COCl)_2$, $SOCl_2$, $PCl_3$, or $Ph_3P.CCl_4$, optionally in solvents such as $CH_2Cl_2$, $CHCl_3$, benzene, or toluene, at 0° C. to elevated temperatures.

Preferred conditions are $SOCl_2$ in $CH_2Cl_2$ at 0° C. to 45° C. for 2 hours.

Step E:

Cyclisation of chloride 55 to azetidine 56 can be performed in the presence of a non-nucleophilic base such as sodium hydride, potassium tert-butoxide, potassium 2-methyl-2-butoxide, LDA, LiHMDS, KHMDS in ethereal solvents such as diethyl either, 1,4-dioxane, THF, or TBME.

Preferred conditions are using LiHMDS in THF at 0° C. to 65° C. for 5 hours.

Step F:

Removal of the N-4-methoxybenzyl protecting group can be effected by hydrogenation with hydrogen under normal or elevated pressure or by transfer hydrogenation using ammonium formate or cyclohexadiene as hydrogen source with a catalyst such as $PtO_2$, Pd—C or Raney nickel in solvents such as MeOH, EtOH, $H_2O$, dioxane, THF, HOAc, EtOAc $CH_2Cl_2$, $CHCl_3$, DMF or mixtures thereof. In alternative, N-4-methoxybenzyl protecting group can be removed by treatment with a strong oxidant such as ceric ammonium nitrate (IV), $K_2S_2O_8$ or DDQ in solvents such as $H_2O$, dioxane, THF, acetone, dichloromethane, $CH_3CN$ or mixtures thereof.

Preferred conditions are using $(NH_4)_2Ce(NO_3)_6$ in a 4:1 mixture of $CH_3CN$ and water at room temperature for 48 hours.

Scheme 13

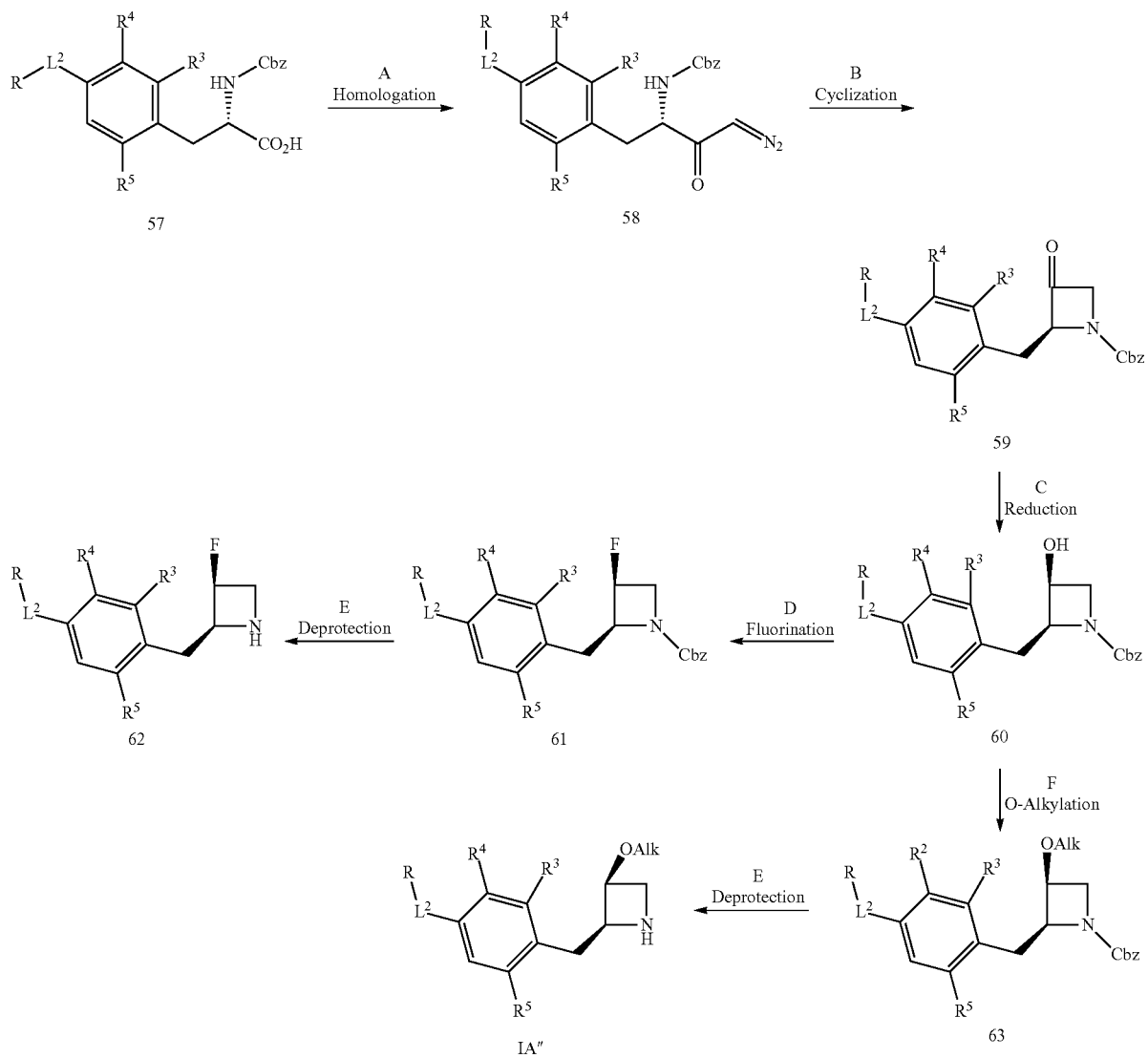

Wherein the substituent R is hydrogen, methoxy or bromide, Alk is lower alkyl and the other substituents are as described above.

Step A:

Homologation reaction of commercially available N-Cbz alpha-aminoacids 57 to alpha-diazo ketone 58 can be accomplished by a stepwise process involving acyl halide intermediates. Carboxylic acid 57 can be converted to corresponding acyl halides by treatment with halogenating reagents such as $(COCl)_2$, $SOCl_2$, $PCl_3$, $PBr_3$, $Ph_3P.Br_2$ or 1-chloro-N,N,2-trimethylpropenylamine optionally in solvents such as $CH_2Cl_2$, $CHCl_3$, benzene, or toluene, at 0° C. to elevated temperatures. In the second step, acyl halide intermediate can be treated with (trimethylsilyl)diazomethane in solvents such as hexanes, acetonitrile, THF, diethyl ether or mixture thereof at temperature between −10° C. and room temperature.

Preferred conditions are for the first step 1-chloro-N,N, 2-trimethylpropenylamine [CAS 26189-59-3] in $CH_2Cl_2$ at room temperature for 30 minutes, according to the method of Ghosez and co-workers (*J. Chem. Soc., Chem. Commun.* 1979, 1180; *Org. Synth.* 1980, 59, 26-34), and for the second step reaction with (trimethylsilyl)diazomethane in hexanes at −10° C. to room temperature for 1 hour.

Step B:

Cyclisation of alpha-diazo ketone 58 to azetidinone 59 can be accomplished by a rhodium-catalyzed intramolecular carbenoid insertion reaction according to the method of Hanessian and co-workers (*Can. J Chem.*, 2001, 79, 1812-1826).

Preferred conditions are using catalytic $Rh_2(OAc)_4$ in $CH_2Cl_2$ under anhydrous conditions using a catalytic amount of triethylamine and mixing the reactants at −40° C. and then allowing to react at room temperature overnight.

Step C:

Diastereoselective reduction of ketone 59 to alcohol 60 can be obtained by treatment with reducing agents such as $NaBH_4$, $LiBH_4$, $LiBH(sec-Bu)_3$ or borane in combination with chiral oxaborolidines as catalyst, according to the method of Corey and co-workers (*J. Org. Chem.*, 1988, 53, 2861-2863), in a solvent such as MeOH, EtOH, THF, dioxane, dichloromethane or mixture thereof.

Preferred conditions are using borane dimethyl sulfide and a catalytic amount of (−)-(S)-2-methyl-CBS-oxaborolidine [CAS 112022-81-8] in anhydrous THF at 0° C. for 2 hours.

Step D:

Conversion of secondary alcohol 60 to the corresponding organofluorine 61 can be performed by treatment with fluorinating agents such as diethylaminosulfur trifluoride (DAST), morpholinosulfur trifluoride, 2,2-difluoro-1,3-dimethylimidazolidine, bis(2-methoxyethyl) aminosulfur trifluoride (Deoxo-Fluor™), $Et_3N.(HF)_3$ in combination with PBSF or XtalFluor-E® in combination with $Et_3N.(HF)_3$ in solvents such as THF, DME, DCE or dichloromethane.

Preferred conditions are using XtalFluor-E® [CAS 63517-29-3] in combination with $Et_3N.(HF)_3$ in dichloromethane at room temperature for 1 hour. Extensive $^1$HNMR studies on 61 enabled its structural assignment as 2,3-cis isomer.

Step E:

Removal of N-Cbz protecting group can be effected by hydrogenation with hydrogen under normal or elevated pressure or by transfer hydrogenation using ammonium formate or cyclohexadiene as hydrogen source with a catalyst such as $PtO_2$, Pd—C or Raney nickel, optionally in presence of HCl, in solvents such as MeOH, EtOH, $H_2O$, dioxane, THF, HOAc, EtOAc $CH_2Cl_2$, $CHCl_3$, DMF or mixtures thereof.

Preferred conditions are palladium on charcoal in the presence of HCl in EtOH and 1 atm $H_2$ in MeOH at room temperature for 16 hours.

Separation of epimers at C3 can be conveniently performed at this stage using chiral HPLC.

Step F:

O-alkylation reaction of secondary alcohol 60 to the corresponding ether 63 can be performed in presence of a base such as KO$^t$Bu, NaO$^t$Bu, NaH, KHMDS, NaHMDS, LDA in solvents such as 1,4-dioxane, DME, THF, DMF and DMSO by treatment with alkylating agents such as methyl iodide or ethyl iodide.

Preferred conditions are NaH in THF at room temperature for 16 hours.

Scheme 14

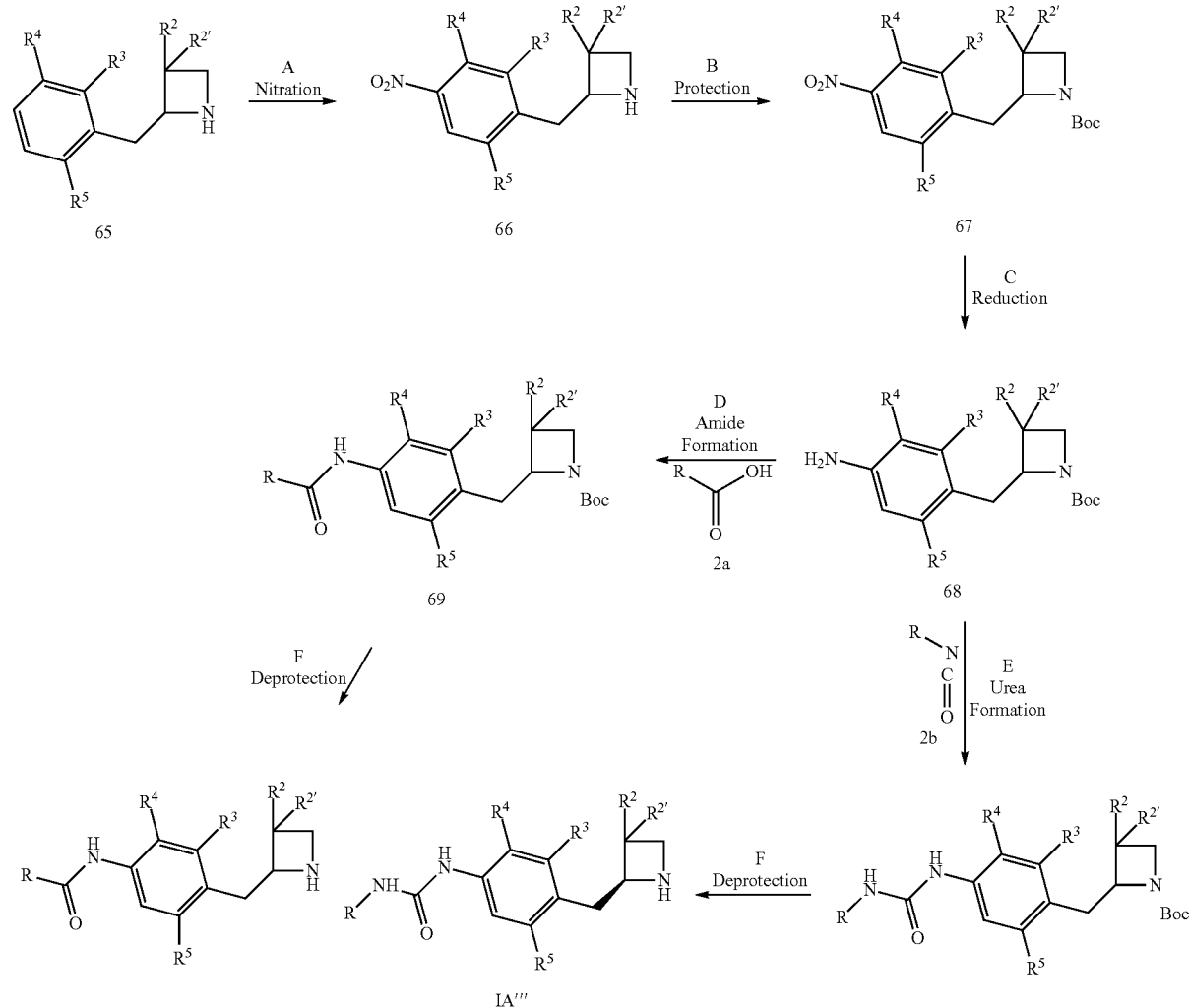

wherein R is phenyl optionally substituted by one or more substituents, selected from halogen, lower alkyl substituted by halogen or lower alkoxy, or is a five or six membered heteroaryl, selected from pyridinyl, pyrimidinyl, pyrazinyl, pyridazinyl or pyrazolyl, which heteroaryls are optionally substituted by one or more substituents, selected from halogen, lower alkyl, lower alkoxy, cyano, cycloalkyl, lower alkyl substituted by halogen, lower alkoxy substituted by halogen or by phenyl substituted by halogen;

The substituents $R^2$, $R^{2'}$, $R^3$, $R^4$ and $R^5$ are described above.

Step A:

Regioselective aromatic nitration of azetidine 65 can be effected by treatment with a mixture of nitric acid and sulfuric acid, optionally in the presence of a co-solvent such as dichloromethane.

Preferred conditions are using stoichiometric amount of nitric acid in a 2:1 mixture of sulfuric acid and dichloromethane at −20° C. to room temperature for 1 hour.

Step B:

Protection of the secondary amino group in 66 can be effected by treatment with di-tert-butyl carbonate, optionally in the presence of an organic base such as triethylamine, N,N-diisopropylethylamine or N-methylmorpholine, in halogenated solvents such as dichloromethane or 1,2-dichloroethane or ethereal solvents such as diethyl ether, dioxane, THF or TBME or protic solvents such as MeOH, EtOH.

Preferred conditions are using N,N-diisopropylethylamine in MeOH at room temperature for 16 hours.

Step C:

Reduction of the nitro group in 67 to the corresponding aniline 68 can be effected by hydrogenation with hydrogen under normal or elevated pressure in the presence of a catalyst such as $PtO_2$, Pd—C or Raney nickel in solvents such as MeOH, EtOH, $H_2O$, dioxane, THF, HOAc, EtOAc, DMF or mixtures thereof.

Preferred conditions are palladium on charcoal in MeOH at room temperature and 1 atm $H_2$ for 16 hours.

If desired, the minor meta and ortho isomers can be separated at this stage by preparative HPLC.

Step D:

Amide formation can be accomplished by a coupling reaction between a carboxylic acid 2a and aniline 68 with a coupling reagent such as DCC, EDC, TBTU, HBTU, HATU or 4-(4,6-dimethoxy-1,3,5-triazin-2-yl)-4-methylmorpholinium chloride, optionally in the presence of an organic base such as triethylamine, N,N-diisopropylethylamine or N-methylmorpholine in solvents such as dichloromethane, 1,2-dichloroethane, DMF, DMSO, or ethereal solvents including diethyl ether, 1,4-dioxane, THF, DME, or TBME or alcohols such as MeOH, EtOH or i-PrOH.

Preferred conditions are 4-(4,6-dimethoxy-1,3,5-triazin-2-yl)-4-methylmorpholinium chloride [CAS 3945-69-5] in absence of a base in MeOH at temperatures of 0° C. to 50° C. for 3 hours.

Step E:

Urea formation can be accomplished by a coupling reaction between aniline 68 and an isocyanate 2b, optionally in the presence of an organic base such as triethylamine, N,N-diisopropylethylamine or N-methylmorpholine in halogenated solvents such as dichloromethane, 1,2-dichloroethane, chlorobenzene or protic solvents such as DMF, NMP, DMA or ethereal solvents such as diethyl ether, 1,4-dioxane, THF, DME or TBME.

Preferred conditions are in absence of base in THF at 30-60° C. for 16-24 hours.

Step F:

Removal of the N-Boc protecting group can be effected with mineral acids such as HCl, $H_2SO_4$ or $H_3PO_4$ or organic acids such as $CF_3COOH$, $CHCl_2COOH$, HOAc or p-toluenesulfonic acid in solvents such as $CH_2Cl_2$, $CHCl_3$, THF, MeOH, EtOH or $H_2O$ at 0-80° C.

Preferred conditions are $CF_3COOH$ in $CH_2Cl_2$ at room temperature for 2 hours or 4.0 M HCl in 1,4-dioxane at 60° C. for 2 hours then allowed to cool to room temperature for 16 hours.

Scheme 15

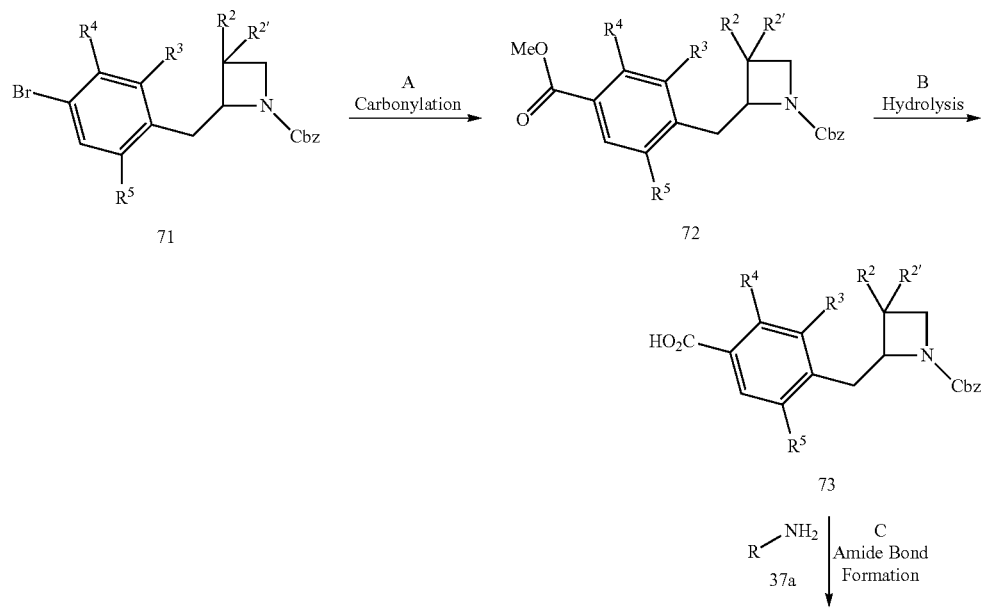

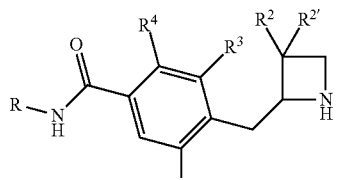 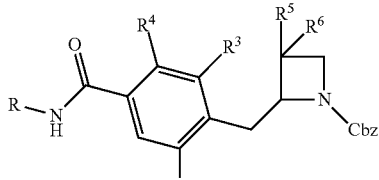

IA'''' ← D Deprotection — 74 wherein R is phenyl optionally substituted by one or more substituents, selected from halogen, lower alkyl substituted by halogen or lower alkoxy, or is a five or six membered heteroaryl, selected from pyridinyl, pyrimidinyl, pyrazinyl, pyridazinyl or pyrazolyl, which heteroaryls are optionally substituted by one or more substituents, selected from halogen, lower alkyl, lower alkoxy, cyano, cycloalkyl, lower alkyl substituted by halogen, lower alkoxy substituted by halogen or by phenyl substituted by halogen;

The substituents $R^2$, $R^{2'}$, $R^3$, $R^4$ and $R^5$ are described above.

Step A:

Methyl ester 72 can be obtained by a palladium-mediated carbonylation reaction between aryl bromide 71 and $CO_{(g)}$ in MeOH in the presence of an organic base such as triethylamine, N,N-diisopropylethylamine or N-methylmorpholine and a catalytic amount of phosphine ligand.

Preferred conditions are catalytic 1,1'-Bis(diphenylphosphino)ferrocene-palladium(II)dichloride·$CH_2Cl_2$ [CAS 95464-05-4], triethylamine as base in a 1:1 mixture of MeOH/EtOAc at 110° C. under 50 bar $CO_{(g)}$ for 16 hours.

Step B:

Hydrolysis of methyl ester 72 to carboxylic acid 73 can be performed under basic conditions by treatment with an inorganic base such as LiOH, NaOH, KOH, $K_2CO_3$ in a mixture of an organic solvent such as MeOH, EtOH, THF, $CH_3CN$, DMF, DMSO and water at room temperature to elevated temperatures.

Preferred conditions are LiOH in a 1:1 mixture of THF and water at room temperature for 12 hours.

Step C:

Amide bond formation can be accomplished by a coupling reaction between carboxylic acid 73 and an aniline 37a in the presence of a coupling reagent such as DCC, EDC, TBTU or HATU in the presence of an organic base such as triethylamine, N,N-diisopropylethylamine or N-methylmorpholine in halogenated solvents such as dichloromethane or 1,2-dichloroethane or ethereal solvents such as diethyl ether, 1,4-dioxane, THF, DME or TBME.

Alternatively, amide bond formation can be accomplished by a coupling reaction between an aniline 37a and an acyl chloride obtained in situ from the corresponding carboxylic acid 73 by treatment with oxalyl chloride or 1-chloro-N,N,2-trimethylpropenylamine in halogenated solvents such as dichloromethane or 1,2-dichloroethane or ethereal solvents such as diethyl ether, 1,4-dioxane, THF, DME or TBME in the presence of a catalyst such as DMF.

Preferred conditions are with 1-chloro-N,N,2-trimethylpropenylamine [CAS 26189-59-3] in dichloromethane, followed by addition of aniline in DMF in presence of N,N-diisopropylethylamine at room temperature for 1 hour.

Step D:

Removal of N-Cbz protecting group can be effected by hydrogenation with hydrogen under normal or elevated pressure or by transfer hydrogenation using ammonium formate or cyclohexadiene as hydrogen source with a catalyst such as $PtO_2$, Pd—C or Raney nickel, optionally in presence of HCl, in solvents such as MeOH, EtOH, $H_2O$, dioxane, THF, HOAc, EtOAc $CH_2Cl_2$, $CHCl_3$, DMF or mixtures thereof.

Preferred conditions are palladium on charcoal in MeOH at room temperature and 1 atm $H_2$ for 2 hours.

Isolation and Purification of the Compounds

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be had by reference to the preparations and examples herein below. However, other equivalent separation or isolation procedures could, of course, also be used. Racemic mixtures of chiral compounds of formula I can be separated using chiral HPLC. Racemic mixtures of chiral synthetic intermediates may also be separated using chiral HPLC.

Salts of Compounds of Formula I

The compounds of formula I are basic and may be converted to a corresponding acid addition salt. The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, 2,2,2-trifluoroacetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained between 0° C. and 50° C. The resulting salt precipitates spontaneously or may be brought out of solution with a less polar solvent.

Example 1

3-benzylazetidine

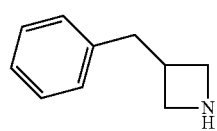 [SMILES: c1ccc(CC2CNC2)cc1]

a) tert-butyl 3-[(4-bromophenyl)methylene]azetidine-1-carboxylate

To a stirred solution of (4-bromobenzyl)triphenylphosphonium bromide (3.29 g, 6.43 mmol, CAS 51044-13-4) in DMF (40 mL) was added NaH (280 mg, 6.43 mmol, 60% in mineral oil). After 15 min, tert-butyl 3-oxoazetidine-1-carboxylate (1.0 g, 5.84 mmol, CAS 398489-26-4) in DMF (8 mL) was added via syringe. The reaction mixture was heated to 65° C. overnight, before being quenched by addition of saturated aqueous NH$_4$Cl and extracted with EtOAc. The organic phase was washed with water, brine, dried (Na$_2$SO$_4$) and concentrated in vacuo. The residue was purified by flash column chromatography (silica gel; gradient: 0% to 15% EtOAc in heptane) to afford the title compound (1.42 g, 75%) as a white solid. MS (ISP): 268 ([M-C$_4$H$_8$+H]$^+$).

b) 3-(4-bromobenzylidene)azetidinium 2,2,2-trifluoroacetate

To a stirred solution of tert-butyl 3-[(4-bromophenyl)methylene]azetidine-1-carboxylate (24 mg, 74.0 μmol) in CH$_2$Cl$_2$ (1.0 mL) was added TFA (198 μL, 2.59 mmol). The reaction mixture was stirred at room temperature for 12 hours. The resulting suspension was filtered through a sintered funnel. The collected 2,2,2-trifluoroacetate salt was washed with further anhydrous diethyl ether then dried under high vacuum to afford the title compound (21.4 mg, 85%) as a white powder. MS (ISP): 226.4 ([{$^{81}$Br}M+H]$^+$), 224.2 ([{$^{79}$Br}M+H]$^+$).

c) 3-benzylazetidinium 2,2,2-trifluoroacetate

To a stirred solution of 3-(4-bromobenzylidene)azetidinium 2,2,2-trifluoroacetate (16 mg, 47.3 μmol) in MeOH (2 mL) was added 10 wt. % Pd/C (2.52 mg, 2.37 μmol) and the resulting black suspension was purged by evacuation and then back filled with a stream of hydrogen (balloon) for three times. The mixture was stirred for 16 hours at room temperature under hydrogen atmosphere then filtered through a pad of dicalite. The filter cake was rinsed with MeOH and the filtrate was concentrated in vacuo. The residue was triturated and washed with anhydrous diethyl ether then dried under high vacuum to afford the title compound (8.0 mg, 64%) as a white solid. MS (ISP): 146.1 ([M+H]$^+$).

Example 2

N-[4-[azetidin-3-yl(methyl)amino]phenyl]-2-(trifluoromethyl)pyridine-4-carboxamide

a) N-(4-bromophenyl)-2-(trifluoromethyl)pyridine-4-carboxamide

To a stirred solution of 2-(trifluoromethyl)isonicotinic acid (500 mg, 2.62 mmol, CAS 131747-41-6) and 4-bromoaniline (540 mg, 3.14 mmol, CAS 106-40-1) in DMF (13.1 mL) was added sequentially N-methylmorpholine (863 μL, 7.85 mmol) and HBTU (1.49 g, 3.92 mmol, CAS 94790-37-1). The reaction mixture was stirred for 16 hours at room temperature. The reaction mixture was partitioned between aqueous citric acid (10 wt. %) and EtOAc. The layers were separated and the organic phase was washed with saturated aqueous NaHCO$_3$, dried (Na$_2$SO$_4$) and concentrated in vacuo. The residue was purified by flash column chromatography (silica gel; gradient: 0% to 30% EtOAc in heptane) to afford the title compound (761 mg, 84%) as viscous oil. MS (ISP): 347.2 ([{$^{81}$Br}M+H]$^+$), 345.2 ([{$^{79}$Br}M+H]$^+$).

b) tert-butyl 3-[N-methyl-4-[[2-(trifluoromethyl)pyridine-4-carbonyl]amino]anilino]azetidine-1-carboxylate A screw-cap vial was charged with tert-butyl 3-(methylamino)azetidine-1-carboxylate (17.8 mg, 95.6 μmol, CAS 454703-20-9), N-(4-bromophenyl)-2-(trifluoromethyl)pyridine-4-carboxamide (30 mg, 86.9 μmol, Eq: 1.00), tris(dibenzylideneacetone)dipalladium (0) (3.98 mg, 4.35 μmol) and 2-dicyclohexylphosphino-2'-(N,N-dimethylamino)biphenyl (3.42 mg, 8.69 μmol). The vial was then degassed by alternative evacuation and back filling with nitrogen. THF (190 μL) was added and the resulting mixture was flushed with a stream of nitrogen for 10 min. LiHMDS in THF (1.0 M, 191 μL, 191 μmol) was added dropwise and the resulting brown solution was heated to 65° C. in an oil bath for 17 hours then filtered directly through a plug of dicalite. The filter cake was rinsed with EtOAc and the filtrate was washed with brine, dried (Na$_2$SO$_4$) and concentrated in vacuo. The residue was purified by flash column chromatography (silica gel; gradient: 0% to 70% EtOAc in heptane) to afford the title compound (29 mg, 75%) as a yellow oil. MS (ISP): 395.2 ([M-C$_4$H$_8$+H]$^+$).

c) N-[4-[azetidin-3-yl(methyl)amino]phenyl]-2-(trifluoromethyl)pyridine-4-carboxamide 2,2,2-trifluoroacetic acid To a stirred solution of tert-butyl 3-[N-methyl-4-[[2-(trifluoromethyl)pyridine-4-carbonyl]amino]anilino]azetidine-1-carboxylate (29 mg, 64.4 μmol) in CH$_2$Cl$_2$ (308 μL) was added TFA (277 μL, 3.59 mmol). The resulting yellow solution was stirred at room temperature for 2 hours before all volatiles were removed under high vacuum to afford the title compound (30 mg, quantitative) as a light yellow oil. MS (ISP): 351 ([M+H]$^+$).

Example 3

N-[4-(azetidin-3-ylamino)phenyl]-2-(trifluoromethyl)pyridine-4-carboxamide

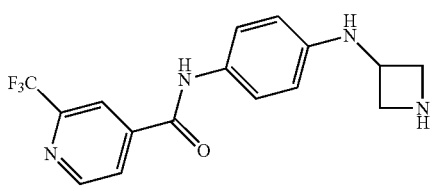 [SMILES: O=C(Nc1ccc(NC2CNC2)cc1)c1ccnc(C(F)(F)F)c1]

a) tert-butyl 3-[4-[[2-(trifluoromethyl)pyridine-4-carbonyl]amino]anilino]azetidine-1-carboxylate A screw-cap vial was charged with N-(4-bromophenyl)-2-(trifluoromethyl)pyridine-4-carboxamide (30 mg, 86.9 µmol), copper (I) iodide (1.66 mg, 8.69 µmol), L-proline (2.00 mg, 17.4 µmol, CAS 147-85-3) and potassium carbonate (24.0 mg, 174 µmol). The vial was then degassed by alternative evacuation and back filling with nitrogen. DMSO (435 µL) and tert-butyl 3-aminoazetidine-1-carboxylate (15.0 mg, 86.9 µmol, CAS 193269-78-2) were added and the resulting mixture was flushed with a stream of nitrogen for 10 min. The reaction mixture was heated to 60° C. in an oil bath for 17 hours, before being partitioned between water and EtOAc. The layers were separated and the organic phase was washed with brine, dried ($Na_2SO_4$) and concentrated in vacuo. The residue was purified by flash column chromatography (silica gel; gradient: 0% to 70% EtOAc in heptane) to afford the title compound (11 mg, 29%) as a yellow oil. MS (ISP): 381.2 ($[M-C_4H_8+H]^+$).

b) N-[4-(azetidin-3-ylamino)phenyl]-2-(trifluoromethyl)pyridine-4-carboxamide 2,2,2-trifluoroacetic acid To a stirred solution of (11 mg, 25.2 µmol) in $CH_2Cl_2$ (208 µL) was added TFA (108 µL, 1.41 mmol). The resulting yellow solution was stirred at room temperature for 2 hours before all volatiles were removed under high vacuum to afford the title compound (11.4 mg, 100%) as a light yellow oil. MS (ISP): 337 ($[M+H]^+$).

Example 4

N-(4-(azetidin-3-yloxy)phenyl)-4-chlorobenzamide

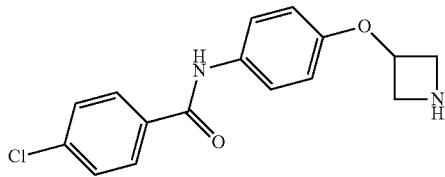 [SMILES: O=C(Nc1ccc(OC2CNC2)cc1)c1ccc(Cl)cc1]

a) tert-butyl 3-(4-nitrophenoxy)azetidine-1-carboxylate

To a stirred solution of tert-butyl 3-hydroxyazetidine-1-carboxylate (2.6142 g, 15.1 mmol) and 1-fluoro-4-nitrobenzene (2.24 g, 15.8 mmol, CAS 350-46-9) in THF (40 mL) at 0° C. was added KHMDS in toluene (0.5 M, 31.6 mL, 15.8 mmol). After 30 min, the reaction mixture was allowed to warm to room temperature and stirred for further 16 hours. The reaction was quenched by addition of water and extracted with EtOAc. The organic phase was washed with water, brine, dried ($Na_2SO_4$) and concentrated in vacuo to afford the title compound (3.85 g, 87%) as a brown oil which was used in the next step without further purification.

b) tert-butyl 3-(4-aminophenoxy)azetidine-1-carboxylate

To a stirred solution of tert-butyl 3-(4-nitrophenoxy)azetidine-1-carboxylate (3.8489 g, 13.1 mmol) in EtOAc (45 mL) was added 10 wt. % Pd/C (696 mg, 654 µmol) and the resulting black suspension was purged by evacuation and then back filled with a stream of hydrogen (balloon) for three times. The mixture was stirred for 16 hours at room temperature under hydrogen atmosphere. The resulting suspension was filtered directly through a plug of dicalite. The filter cake was rinsed with EtOAc and the filtrate was concentrated in vacuo. The residue was purified by flash column chromatography (silica gel; gradient: 0% to 50% EtOAc in heptane) to afford the title compound (2.45 g, 71%) as a light brown powder. MS (ISP): 209.4 ($[M-C_4H_8+H]^+$).

c) tert-butyl 3-[4-[(4-chlorobenzoyl)amino]phenoxy]azetidine-1-carboxylate

To a stirred solution of tert-butyl 3-(4-aminophenoxy)azetidine-1-carboxylate (23.85 mg, 90.2 µmol) in DMF (440 uL) were added sequentially N-methylmorpholine (29.8 µL, 271 µmol), HBTU (51.3 mg, 135 µmol) and 4-chlorobenzoic acid (19.3 mg, 0.123 mmol, CAS 74-11-3). The resulting mixture was stirred at room temperature overnight before being partitioned between EtOAc and saturated aqueous $NaHCO_3$ (10 mL). The organic layers were washed with brine, dried ($Na_2SO_4$) and concentrated in vacuo. The residue was purified by flash column chromatography (silica gel; gradient: 0% to 50% EtOAc in heptane) to afford the title compound (30.5 mg, 83%) as a white powder. MS (ISP): 379.2 ($[\{^{37}Cl\}M-C_4H_8+H]^+$), 377.1 ($[\{^{35}Cl\}M-C_4H_8+H]^+$).

d) N-(4-(azetidin-3-yloxy)phenyl)-4-chlorobenzamide hydrochloride

To a stirred solution of tert-butyl 3-[4-[(4-chlorobenzoyl)amino]phenoxy]azetidine-1-carboxylate (30.5 mg) in 1,4-dioxane (0.2 mL) was added a 4.0 M solution of HCl in dioxane (0.25 mL). The reaction mixture was stirred at 60° C. for 2 hours before being cooled to room temperature and stirred for further 6 hours. The resulting suspension was filtered through a sintered funnel. The collected hydrochloride salt was washed with further anhydrous diethyl ether then dried under high vacuum to afford the title compound (18.1 mg, 72%) as a white powder. MS (ISP): 303.2 ($[M+H]^+$).

Example 5

N-(4-(azetidin-3-yloxy)phenyl)-2-(trifluoromethyl)isonicotinamide

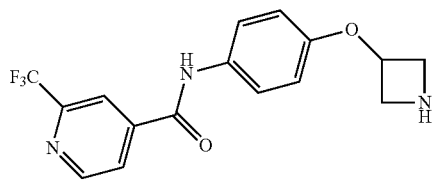

The title compound was obtained in analogy to example 4 using 2-(trifluoromethyl)isonicotinic acid (CAS 131747-41-6) in place of 4-chlorobenzoic acid in step (c). Off-white solid. MS (ISP): 336.7 ($[M+H]^+$).

Example 6

N-(4-(azetidin-3-yloxy)phenyl)-2-(trifluoromethyl)pyrimidine-5-carboxamide

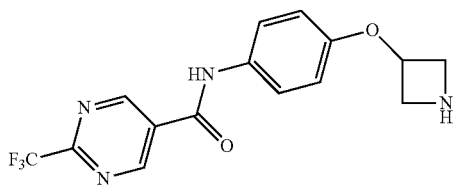 [SMILES: O=C(Nc1ccc(OC2CNC2)cc1)c1cnc(C(F)(F)F)nc1]

The title compound was obtained in analogy to example 4 using 2-(trifluoromethyl)pyrimidine-5-carboxylic acid (CAS 306960-74-7) in place of 4-chlorobenzoic acid in step (c). Off-white solid. MS (ISP): 337.7 ([M+H]+).

Example 7

N-(4-(azetidin-3-yloxy)phenyl)-2-cyano-6-methoxy-isonicotinamide

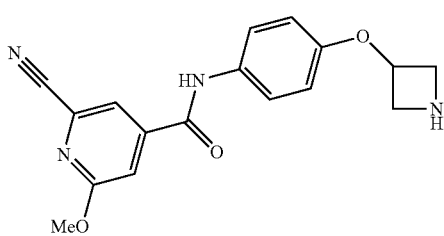 [SMILES: COc1cc(C(=O)Nc2ccc(OC3CNC3)cc2)cc(C#N)n1]

The title compound was obtained in analogy to example 4 using 2-cyano-6-methoxyisonicotinic acid in place of 4-chlorobenzoic acid in step (c). Off-white solid. MS (ISP): 323.7 ([M+H]+).

Example 8

N-[4-(azetidin-3-yloxy)phenyl]-2-(trifluoromethyl)pyrimidin-4-amine

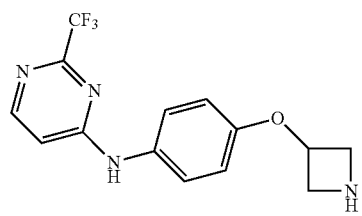 [SMILES: FC(F)(F)c1nccc(Nc2ccc(OC3CNC3)cc2)n1]

a) 1-benzhydrylazetidin-3-yl methanesulfonate

To a stirred solution of 1-benzhydrylazetidin-3-ol (4.0 g, 16.7 mmol, CAS 18621-17-5) in CH$_2$Cl$_2$ (40 mL) was added N,N-diisopropylethylamine (14.6 mL, 83.6 mmol). The reaction mixture was cooled to −20° C., followed by addition of methanesulfonyl chloride (1.95 mL, 25.1 mmol). After 30 min, the reaction mixture was allowed to warm to room temperature and stirred for further 16 hours. The mixture was diluted with CH$_2$Cl$_2$ and the organic phrase washed with aqueous citric acid, aqueous NaHCO$_3$ then brine. Organic layers were collected, dried (Na$_2$SO$_4$) and concentrated in vacuo to afford the title compound (4.85 g, 91%) as an orange solid. MS (ISP): 318.5 ([M+H]+).

b) 1-benzhydryl-3-(4-bromophenoxy)azetidine

To a stirred solution of 4-bromophenol (959 mg, 5.55 mmol, CAS 106-41-2) in DMF (20 mL) at 0° C. was added NaH (532 mg, 11.1 mmol, 60% in mineral oil). After 15 min, 1-benzhydrylazetidin-3-yl methanesulfonate (1.76 g, 5.55 mmol) in DMF (5 mL) was added via syringe. The resulting mixture was heated to 80° C. overnight. The reaction mixture was poured into water and extracted with EtOAc. The combined organic extracts were washed with brine, dried (Na$_2$SO$_4$) and concentrated in vacuo. The crude residue was purified by flash column chromatography (silica gel, 0% to 20% EtOAc in heptane) to afford the title compound (1.53 g, 70%) as a white solid. MS (ISP): 396.2 ([{$^{81}$Br}M+H]+), 394.1 ([{$^{79}$Br}M+H]+).

c) 3-(4-bromophenoxy)azetidine hydrochloride

To a stirred solution of 1-benzhydryl-3-(4-bromophenoxy)azetidine (845 mg, 2.14 mmol) in 1,2-dichloroethane (12 mL) was added 1-chloroethyl chloroformate (301 μL, 2.79 mmol). The reaction mixture was heated to 70° C. for 2 hours before being allowed to cool to room temperature. Methanol (12.0 mL) was added and reaction mixture was heated to reflux at 70° C. for further 2 hours before being concentrated in vacuo. The crude residue was triturated with diethyl ether then filtered and dried under high vacuum to afford the title compound (480 mg, 84%) as a white powder. MS (ISP): 230.0 ([{$^{81}$Br}M+H]+), 228.1 ([{$^{79}$Br}M+H]+).

d) tert-butyl 3-(3-bromophenoxy)azetidine-1-carboxylate

To a stirred solution of 3-(4-bromophenoxy)azetidine hydrochloride (443 mg, 1.67 mmol) in methanol (4 mL) was added N,N-diisopropylethylamine (585 μL, 3.35 mmol). After 15 min, di-tert-butyl dicarbonate (731 mg, 3.35 mmol) was added and the reaction was stirred overnight. The reaction was quenched by addition of water then extracted with ethyl acetate. The combined organic extracts were washed with brine, dried (Na$_2$SO$_4$) and concentrated in vacuo. The crude material was purified by flash chromatography (silica gel, 0% to 20% EtOAc in heptane) to afford the title compound as a white solid (428 mg, 74%). MS (ISP): 274.1 ([{$^{81}$Br}M-C$_4$H$_8$+H]+), 272.1 ([{$^{79}$Br}M-C$_4$H$_8$+H]+).

e) tert-butyl 3-(4-(diphenylmethyleneamino)phenoxy)azetidine-1-carboxylate

A microwave vial was charged with tert-butyl 3-(3-bromophenoxy)azetidine-1-carboxylate (274 mg, 835 μmol), benzophenone imine (66 mg, 918 μmol, CAS 1013-88-3), sodium tert-butoxide (128 mg, 1.34 mmol), rac-2,2'-bis(diphenylphosphino)-1,1'-binaphthyl (52.0 mg, 83.5 μmol), Pd$_2$(dba)$_3$ (22.9 mg, 25.0 μmol) and toluene (2 mL). The resulting mixture was degassed for 5 min by bubbling nitrogen through the reaction mixture. The reaction was heated to 90° C. overnight and then filtered directly through a pad of dicalite. The filter cake was rinsed with EtOAc and the filtrate concentrate in vacuo. The crude residue was purified by flash chromatography (silica gel, 0% to 30% EtOAc in heptane) to afford the title compound (321 mg, 89%) as a light yellow oil. MS (ISP): 429.1 ([M+H]⁺).

f) tert-butyl 3-(4-aminophenoxy)azetidine-1-carboxylate

To a stirred solution of tert-butyl 3-(4-(diphenylmethyl-eneamino)phenoxy)azetidine-1-carboxylate (312 mg, 728 µmol) in methanol (4 mL) was added under nitrogen sodium acetate (179 mg, 2.18 mmol) and hydroxylamine hydrochloride (111 mg, 1.6 mmol). The reaction mixture was stirred at 50° C. overnight. The resulting white precipitate was filtered off, while the filtrate was concentrated in vacuo and purified by flash chromatography (silica gel, 0% to 40% EtOAc in heptane) to afford the title compound (1.53 g, 70%) as a white solid. MS (ISP): 209.1 ([M-$C_4H_8$+H]⁺).

g) tert-butyl 3-(4-(2-(trifluoromethyl)pyrimidin-4-ylamino)phenoxy)azetidine-1-carboxylate A microwave vial was charged with tert-butyl 3-(4-aminophenoxy)azetidine-1-carboxylate (24.83 mg, 93.9 µmol), 4-chloro-2-(trifluoromethyl)pyrimidine (113 mol, CAS 1514-96-1), tris(dibenzylideneacetone)dipalladium(0) (8.6 mg, 9.39 µmol), 4,5-bis(diphenylphosphino)-9,9-dimethylxanthene (10.9 mg, 18.8 µmol), cesium carbonate (45.9 mg, 141 µmol) and diglyme (419 µL). The mixture was degassed for 5 min by bubbling with nitrogen through the reaction medium. The reaction was heated to 100° C. overnight and then filtered directly through a pad of dicalite. The filter cake was rinsed with EtOAc and the filtrate concentrate in vacuo. The crude residue was purified by flash chromatography (silica gel, 0% to 50% EtOAc in heptane) to afford the title compound (27.2 mg, 58%) as a yellow powder. MS (ISP): 411.2 ([M+H]⁺).

h) N-[4-(azetidin-3-yloxy)phenyl]-2-(trifluoromethyl)pyrimidin-4-amine hydrochloride To a stirred solution tert-butyl 3-(4-(2-(trifluoromethyl)pyrimidin-4-ylamino)phenoxy)azetidine-1-carboxylate of (24.2 mg) in 1,4-dioxane (300 µL) was added a 4.0 M solution of HCl in 1,4-dioxane (300 µL). The reaction mixture was stirred at 60° C. for 90 min then cooled to room temperature and stirred for further 16 hours. The resulting suspension was filtered through a sintered funnel. The collected hydrochloride salt was washed with further anhydrous diethyl ether then dried under high vacuum to afford the title compound (18 mg, 88%) as a white solid. MS (ISP): 311 ([M+H]⁺).

Example 9

N-(4-(azetidin-3-yloxy)phenyl)-5-(trifluoromethyl)pyrimidin-2-amine

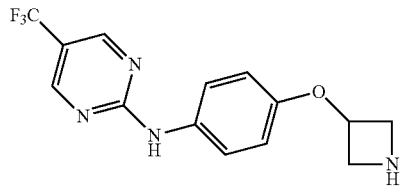 [SMILES: FC(F)(F)c1cnc(Nc2ccc(OC3CNC3)cc2)nc1]

The title compound was obtained in analogy to example 8 using 2-chloro-5-(trifluoromethyl)pyrimidine (CAS 69034-12-4) in place of 4-chloro-2-(trifluoromethyl)pyrimidine in step (g). colorless oil. MS (ISP): 311.3 ([M+H]⁺).

Example 10

N-(4-(azetidin-3-yloxy)phenyl)-3-cyclopropyl-1H-pyrazole-5-carboxamide

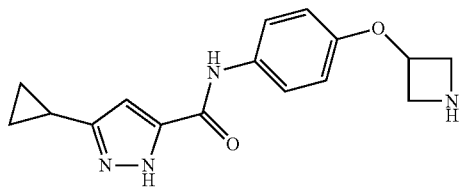 [SMILES: O=C(Nc1ccc(OC2CNC2)cc1)c1cc(C2CC2)n[nH]1]

a) tert-butyl 3-[4-[(3-cyclopropyl-1H-pyrazole-5-carbonyl)amino]phenoxy]azetidine-1-carboxylate To a stirred solution of tert-butyl 3-(4-aminophenoxy)azetidine-1-carboxylate (30 mg, 113 µmol) in DMF (500 µL) under nitrogen was added 3-cyclopropyl-1H-pyrazole-5-carboxylic acid (22.5 mg, 148 µmol, CAS 401629-04-7), N-methylmorpholine (37.4 µL, 340 µmol) and HBTU (64.6 mg, 170 µmol). The reaction mixture was stirred overnight at room temperature before being quenched by addition of saturated aqueous $NH_4Cl$. The reaction mixture was poured into water and extracted with EtOAc. The combined organic extracts were washed with saturated $NaHCO_3$, brine, then dried ($Na_2SO_4$) and concentrated in vacuo. The crude material was then purified by flash chromatography (silica gel, 0% to 50% EtOAc in heptane) to afford the title compound as a white solid (33.5 mg, 74%).

b) N-(4-(azetidin-3-yloxy)phenyl)-3-cyclopropyl-1H-pyrazole-5-carb oxamide

To a stirred solution tert-butyl 3-(4-(2-(trifluoromethyl)pyrimidin-4-ylamino)phenoxy)azetidine-1-carboxylate of (33.5 mg) in dioxane (400 µL) was added a 4.0 M solution of HCl in 1,4-dioxane (200 µL). The reaction mixture was stirred at 60° C. for 90 min then cooled to room temperature. All the volatiles were removed under vacuum and the residue was purified by preparative HPLC (mobile phase A: $H_2O$, B: $CH_3CN$ with 0.05% $Et_3N$, C18 column) to afford the title compound (28 mg, 92%) as a colorless oil. MS (ISP): 297.2 ([M−H]⁻).

Example 11

N-(4-(azetidin-3-yloxy)phenyl)-3-ethyl-4-methyl-1H-pyrazole-5-carboxamide

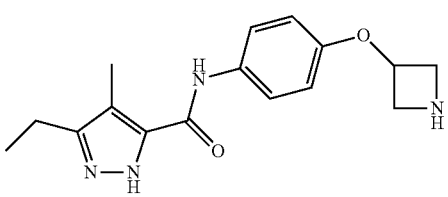 [SMILES: CCc1n[nH]c(C(=O)Nc2ccc(OC3CNC3)cc2)c1C]

The title compound was obtained in analogy to example 10 using 3-ethyl-4-methyl-1H-pyrazole-5-carboxylic acid (CAS 1094347-64-4) in place of 3-cyclopropyl-1H-pyrazole-5-carboxylic acid in step (a). White powder. MS (ISP): 301.4 ([M+H]$^+$).

Example 12

N-(4-(azetidin-3-yloxy)phenyl)-3-isopropyl-1H-pyrazole-5-carboxamide

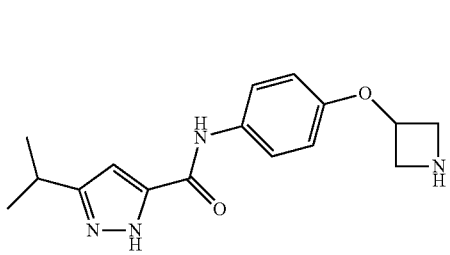 [SMILES: CC(C)c1cc(C(=O)Nc2ccc(OC3CNC3)cc2)[nH]n1]

The title compound was obtained in analogy to example 10 using 3-isopropyl-1H-pyrazole-5-carboxylic acid (CAS 92933-47-6) in place of 3-cyclopropyl-1H-pyrazole-5-carboxylic acid in step (a). Colorless oil. MS (ISP): 301.4 ([M+H]$^+$).

Example 13

N-(4-(azetidin-3-yloxy)phenyl)-4-chloro-3-cyclopropyl-1H-pyrazole-5-carboxamide

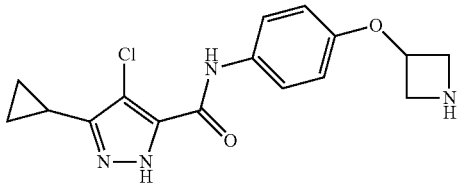 [SMILES: O=C(Nc1ccc(OC2CNC2)cc1)c1[nH]nc(C2CC2)c1Cl]

The title compound was obtained in analogy to example 10 using 4-chloro-3-cyclopropyl-1H-pyrazole-5-carboxylic acid in place of 3-cyclopropyl-1H-pyrazole-5-carboxylic acid in step (a). White powder. MS (ISP): 335.2 ([{$^{37}$Cl}M+H]$^+$), 333.2 ([{$^{35}$Cl}M+H]$^+$).

Example 14

N-(4-(azetidin-3-yloxy)phenyl)-2-cyclopropylpyrimidine-5-carboxamide

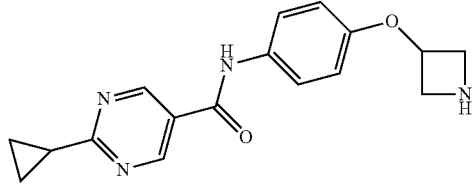 [SMILES: O=C(Nc1ccc(OC2CNC2)cc1)c1cnc(C2CC2)nc1]

The title compound was obtained in analogy to example 10 using 2-cyclopropylpyrimidine-5-carboxylic acid (CAS 648423-79-4) in place of 4-chlorobenzoic acid in step (a). White powder. MS (ISP): 311.3 ([M+H]$^+$).

Example 15

N-[4-(azetidin-3-yloxy)phenyl]-2-ethyl-pyrimidine-5-carboxamide

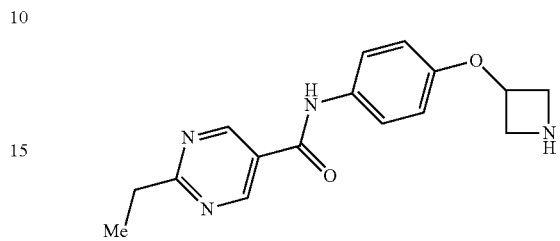

The title compound was obtained in analogy to example 10 using 2-ethylpyrimidine-5-carboxylic acid (CAS 72790-16-0) in place of 4-chlorobenzoic acid in step (a). White powder. MS (ISP): 299.2 ([M+H]$^+$).

Example 16

N-[4-(azetidin-3-yloxy)phenyl]-2-methyl-pyrimidine-5-carboxamide

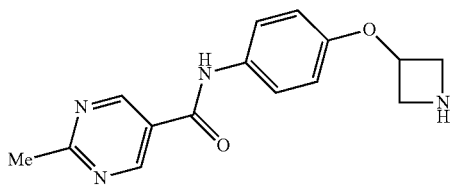 [SMILES: Cc1ncc(C(=O)Nc2ccc(OC3CNC3)cc2)cn1]

The title compound was obtained in analogy to example 10 using 2-methylpyrimidine-5-carboxylic acid (CAS 5194-32-1) in place of 4-chlorobenzoic acid in step (a). White powder. MS (ISP): 285.2 ([M+H]$^+$).

Example 17

N-[4-(azetidin-3-yloxy)phenyl]-2-methyl-5-(trifluoromethyl)pyrazole-3-carboxamide

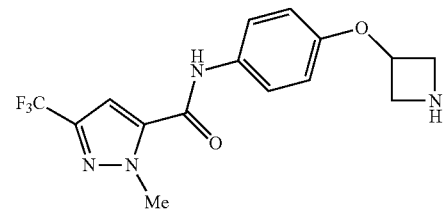 [SMILES: Cn1nc(C(F)(F)F)cc1C(=O)Nc1ccc(OC2CNC2)cc1]

The title compound was obtained in analogy to example 10 using 1-methyl-3-(trifluoromethyl)-1H-pyrazole-5-carboxylic acid (CAS 128694-63-3) in place of 4-chlorobenzoic acid in step (a). White powder. MS (ISP): 341.1 ([M+H]$^+$).

Example 18

4-(azetidin-3-yloxy)-N-[(4-fluorophenyl)methyl]benzamide

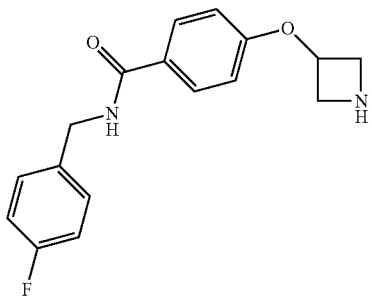 [SMILES: O=C(NCc1ccc(F)cc1)c1ccc(OC2CNC2)cc1]

a) methyl 4-(1-benzhydrylazetidin-3-yloxy)benzoate

To a stirred solution of methyl 4-hydroxybenzoate (610 mg, 4.01 mmol) in DMF (14 mL) at 0° C. was added NaH (321 mg, 6.68 mmol, 60% in mineral oil). After 15 min, 1-benzhydrylazetidin-3-yl methanesulfonate (1.06 g, 3.34 mmol) in DMF (4.5 mL) was added via syringe. The reaction mixture was heated to 80° C. overnight before being poured into water and extracted with EtOAc. The combined organic extracts were washed with brine, dried ($Na_2SO_4$) and concentrated in vacuo. The residue was purified by flash column chromatography (silica gel; gradient: 0% to 30% EtOAc in heptane) to afford the title compound (567 mg, 46%) as a white solid. MS (ISP): 374 ([M+H]$^+$).

b) 4-(1-benzhydrylazetidin-3-yloxy)benzoic acid

To a suspension of methyl 4-(1-benzhydrylazetidin-3-yloxy)benzoate (327 mg, 876 μmol) in methanol (11 mL) and water (5.5 mL) was added lithium hydroxide (105 mg, 4.38 mmol). The resulting mixture was stirred for 4 hours at 45° C. The reaction was quenched by addition of 3.0 M aqueous HCl to pH 2-3 and then extracted with EtOAc. Organic layers were washed with brine, dried ($Na_2SO_4$) and concentrated in vacuo to afford the title compound (214.1 mg, 68%) as a white solid. MS (ISP): 358.2 ([M−H]$^−$).

c) 4-(1-benzhydrylazetidin-3-yl)oxy-N-[(4-fluorophenyl)methyl]benzamide

To a stirred solution of 4-fluorobenzylamine (16.6 μL, 145 μmol, CAS 140-75-0) in DMF (500 μL) under nitrogen was added 4-(1-benzhydrylazetidin-3-yloxy)benzoic acid (40 mg, 111 μmol), N-methylmorpholine (36.7 μL, 334 μmol) and HBTU (63.3 mg, 167 μmol). The reaction mixture was stirred overnight at room temperature before being quenched by addition of saturated aqueous $NH_4Cl$. The reaction mixture was poured into water and extracted with EtOAc. The combined organic extracts were washed with saturated $NaHCO_3$, brine, dried ($Na_2SO_4$) and concentrated in vacuo. The crude material was purified by flash chromatography (silica gel, 0% to 50% EtOAc in heptane) to afford the title compound as a white solid (23 mg, 44%). MS (ISP): 467.4 ([M+H]$^+$).

d) 4-(azetidin-3-yloxy)-N-[(4-fluorophenyl)methyl]benzamide hydrochloride

To a stirred solution of 4-(1-benzhydrylazetidin-3-yl)oxy-N-[(4-fluorophenyl)methyl]benzamide (23 mg, 0.049 mmol) in 1,2-dichloroethane (500 μL) was added 1-chloroethyl chloroformate (0.064 mmol). The reaction mixture was heated at reflux for 2 hours before cooling to room temperature. Methanol (0.5 mL) was added and reaction mixture was heated at reflux for further 2 hours before being concentrated in vacuo. The crude residue was triturated with diethyl ether then filtered and dried under high vacuum to afford the title compound as a white solid (9.8 mg, 53%). MS (ISP): 301.3 ([M+H]$^+$).

Example 19

N-(4-(azetidin-3-yloxy)phenyl)-2-(2,2,2-trifluoroethoxy)pyrimidine-5-carboxamide

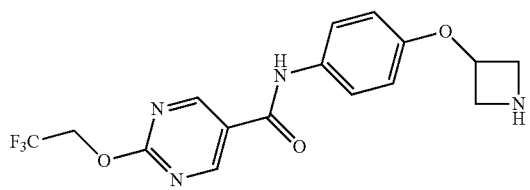 [SMILES: O=C(Nc1ccc(OC2CNC2)cc1)c1cnc(OCC(F)(F)F)nc1]

a) tert-butyl 3-[4-[[2-(2,2,2-trifluoroethoxy)pyrimidine-5-carbonyl]amino]phenoxy]azetidine-1-carboxylate To a stirred solution of 2-(2,2,2-trifluoroethoxy)pyrimidine-5-carboxylic acid (25.0 mg, 113 μmol) and tert-butyl 3-(4-aminophenoxy)azetidine-1-carboxylate (30 mg, 113 μmol) in DMF (500 μL) was added HBTU (64.6 mg, 170 μmol) and N-methylmorpholine (37.4 μL, 340 μmol). The reaction mixture was stirred for 16 hours at room temperature before being partitioned between aqueous $NH_4Cl$ and EtOAc. The layers were separated and the organic phase was washed with saturated aqueous $NaHCO_3$, dried ($Na_2SO_4$) and concentrated in vacuo. The residue was purified by flash column chromatography (silica gel, gradient: 0% to 50% EtOAc in heptane) to afford the title compound (27.2 mg, 51%) as viscous oil. MS (ISP): 469.3 ([M+H]$^+$).

b) N-(4-(azetidin-3-yloxy)phenyl)-2-(2,2,2-trifluoroethoxy)pyrimidine-5-carboxamide 2,2,2-trifluoroacetic acid To a stirred solution of tert-butyl3-[4-[[2-(2,2,2-trifluoroethoxy)pyrimidine-5-carbonyl]amino]phenoxy]azetidine-1-carboxylate (27.2 mg, 58 μmol) in $CH_2Cl_2$ (1 mL) was added 2,2,2-trifluoroacetic acid (0.5 mL). The reaction mixture was stirred for 2 hours at room temperature before all volatiles were removed under high vacuum. The residue was triturated with diethyl ether, filtered and dried under high vacuum to afford the title compound (20 mg, 94%) as a 2,2,2-trifluoroacetate salt. MS (ISP): 369.3 ([M+H]$^+$).

Example 20

4-(azetidin-3-yloxy)-N-phenyl-benzamide

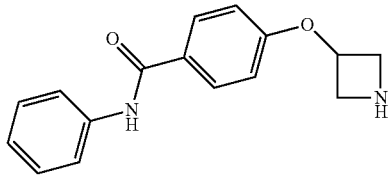 [SMILES: O=C(Nc1ccccc1)c1ccc(OC2CNC2)cc1]

The title compound was obtained in analogy to example 18 using aniline (CAS 62-53-3) in place of 4-fluorobenzylamine in step (c). White powder. MS (ISP): 269.2 ([M+H]$^+$).

Example 21

N-[4-(azetidin-3-yloxy)phenyl]-4-chloro-1-(2,2,2-trifluoroethyl)pyrazole-3-carboxamide

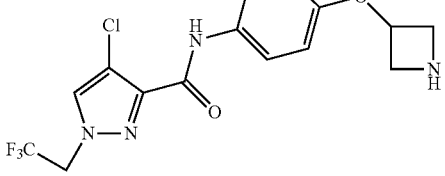

The title compound was obtained in analogy to example 19 using 4-chloro-1-(2,2,2-trifluoroethyl)-1H-pyrazole-3-carboxylic acid (CAS 1006448-63-0) in place of 2-(2,2,2-trifluoroethoxy)pyrimidine-5-carboxylic acid in step (a). Off-white powder. MS (ISP): 377.2 ([{$^{37}$Cl}M+H]$^+$), 375.5 ([{$^{35}$Cl}M+H]$^+$).

Example 22

N-[4-(azetidin-3-yloxy)phenyl]-4-chloro-1-ethyl-pyrazole-3-carboxamide

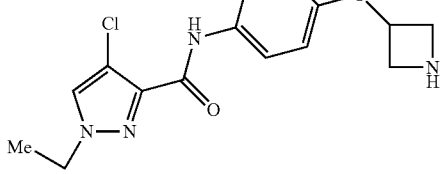

The title compound was obtained in analogy to example 19 using 4-chloro-1-ethyl-1H-pyrazole-3-carboxylic acid in place of 2-(2,2,2-trifluoroethoxy)pyrimidine-5-carboxylic acid in step (a). Off-white powder. MS (ISP): 323.3 ([{$^{37}$Cl}M+H]$^+$), 321.2 ([{$^{35}$Cl}M+H]$^+$).

Example 23

4-(azetidin-3-yloxy)-N-(4-chlorophenyl)benzamide

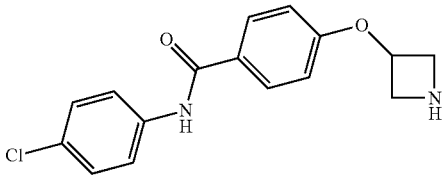 [SMILES: O=C(Nc1ccc(Cl)cc1)c1ccc(OC2CNC2)cc1]

The title compound was obtained in analogy to example 18 using 4-chloroaniline (CAS 106-47-8) in place of 4-fluorobenzylamine in step (c). White powder. MS (ISP): 305.3 ([{$^{37}$Cl}M+H]$^+$), 303.2 ([{$^{35}$Cl}M+H]$^+$).

Example 24

N-(4-(azetidin-3-yloxy)phenyl)-3-(trifluoromethyl)-1H-pyrazole-5-carboxamide

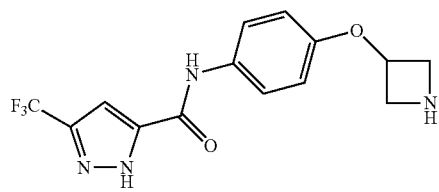 [SMILES: O=C(Nc1ccc(OC2CNC2)cc1)c1cc(C(F)(F)F)n[nH]1]

The title compound was obtained in analogy to example 19 using 3-(trifluoromethyl)-1H-pyrazole-5-carboxylic acid (CAS 129768-28-1) in place of 2-(2,2,2-trifluoroethoxy)pyrimidine-5-carboxylic acid in step (a). White powder. MS (ISP): 327.1 ([M+H]$^+$).

Example 25

N-[4-(azetidin-3-yloxy)-3-fluoro-phenyl]-4-chloro-3-cyclopropyl-1H-pyrazole-5-carboxamide

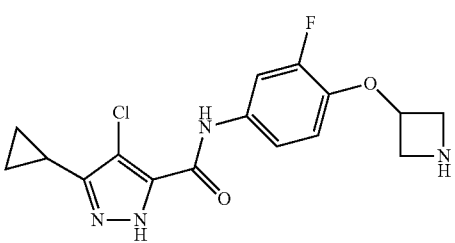 [SMILES: O=C(Nc1ccc(OC2CNC2)c(F)c1)c1[nH]nc(C2CC2)c1Cl]

a) tert-butyl 3-(2-fluoro-4-nitrophenoxy)azetidine-1-carboxylate

To a stirred solution of tert-butyl 3-hydroxyazetidine-1-carboxylate (2.7915 g, 16.1 mmol) and 1,2-difluoro-4-nitrobenzene (2.59 g, 16.3 mmol, CAS 369-34-6) in THF (41 mL) at 0° C. was added KHMDS in toluene (0.5 M, 33.8 mL, 16.9 mmol). After 30 min, the reaction mixture was allowed to warm to room temperature and stirred for an additional hour. The reaction was poured into water and extracted with EtOAc. The combined organic extracts were washed with brine, dried (Na$_2$SO$_4$) and concentrated in vacuo to afford the title compound (4.69 g, 93%) as a brown solid. MS (ISP): 257.2 ([M-C$_4$H$_8$+H]$^+$).

b) tert-butyl 3-(4-amino-2-fluorophenoxy)azetidine-1-carboxylate

To a stirred solution of tert-butyl 3-(2-fluoro-4-nitrophenoxy)azetidine-1-carboxylate (4.4 g, 14.1 mmol) in ethyl acetate (48 mL) under nitrogen atmosphere was added 10 wt. % Pd/C (750 mg, 705 µmol) and the resulting black suspension was purged by evacuation and then back filled with a stream of hydrogen (balloon) for three times. The mixture was stirred for 16 hours at room temperature under hydrogen atmosphere. The resulting suspension was filtered directly through a plug of dicalite. The filter cake was rinsed with EtOAc and the filtrate was concentrated in vacuo. The residue was purified by flash column chromatography (silica gel, gradient: 0% to 50% EtOAc in heptane) to afford the title compound (2.8 g, 70%) as a brown oil. MS (ISP): 227.2 ([M-C$_4$H$_8$+H]$^+$).

c) tert-butyl 3-[4-[(4-chloro-3-cyclopropyl-1H-pyrazole-5-carbonyl)amino]-2-fluoro-phenoxy]azetidine-1-carboxylate To a stirred solution of tert-butyl 3-(4-amino-2-fluorophenoxy)azetidine-1-carboxylate (30 mg, 106 µmol) in DMF (500 µL) under nitrogen was added 4-chloro-3-cyclopropyl-1H-pyrazole-5-carboxylic acid (25.8 mg, 138 µmol), N-methylmorpholine (35 µL, 319 µmol) and HBTU (60.3 mg, 159 µmol). The reaction mixture was stirred overnight at room temperature before being quenched by addition of saturated aqueous NH$_4$Cl. The reaction mixture was poured into water and extracted with EtOAc. The combined organic extracts were washed with saturated NaHCO$_3$, brine, then dried (Na$_2$SO$_4$) and concentrated in vacuo. The residue was purified by flash chromatography (silica gel, gradient: 0% to 50% EtOAc in heptane) to afford the title compound (33 mg, 69%) as a pink powder. MS (ISP): 397.2 ([{$^{37}$Cl}M-C$_4$H$_8$+H]$^+$), 395.1 ([{$^{35}$Cl}M-C$_4$H$_8$+H]$^+$).

d) N-[4-(azetidin-3-yloxy)-3-fluoro-phenyl]-4-chloro-3-cyclopropyl-1H-pyrazole-5-carboxamide 2,2,2-trifluoroacetic acid To a stirred solution of tert-butyl 3-[4-[(4-chloro-3-cyclopropyl-1H-pyrazole-5-carbonyl)amino]-2-fluoro-phenoxy] azetidine-1-carboxylate (33 mg, 73 µmol) in CH$_2$Cl$_2$ (1 mL) was added 2,2,2-trifluoroacetic acid (0.5 mL). The reaction mixture was stirred for 2 hours at room temperature before all volatiles were removed under high vacuum. The residue was triturated with diethyl ether, filtered and dried under high vacuum to afford the title compound as a 2,2,2-trifluoroacetate salt (30 mg, 65%) as a pink powder. MS (ISP): 353.2 ([{$^{37}$Cl}M+H]$^+$), 351.2 ([{$^{35}$Cl}M+H]$^+$).

Example 26

N-[4-(azetidin-3-yloxy)-3-fluoro-phenyl]-2-(trifluoromethyl)pyrimidine-5-carboxamide

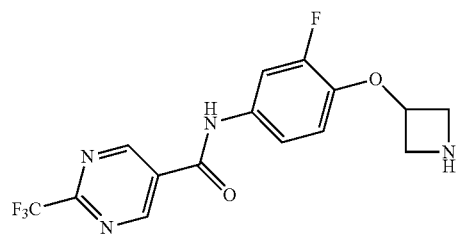 [SMILES: O=C(Nc1ccc(OC2CNC2)c(F)c1)c1cnc(C(F)(F)F)nc1]

The title compound was obtained in analogy to example 25 using 2-(trifluoromethyl)pyrimidine-5-carboxylic acid (CAS 306960-74-7) in place of 4-chloro-3-cyclopropyl-1H-pyrazole-5-carboxylic acid in step (c). White powder. MS (ISP): 357.2 ([M+H]$^+$).

Example 27

N-[4-(azetidin-3-yloxy)-3-fluoro-phenyl]-2-cyclopropyl-pyrimidine-5-carboxamide

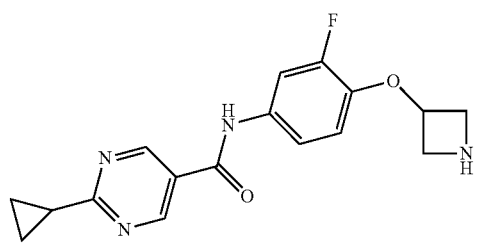 [SMILES: O=C(Nc1ccc(OC2CNC2)c(F)c1)c1cnc(C2CC2)nc1]

The title compound was obtained in analogy to example 25 using 2-cyclopropylpyrimidine-5-carboxylic acid (CAS 648423-79-4) in place of 4-chloro-3-cyclopropyl-1H-pyrazole-5-carboxylic acid in step (c). White powder. MS (ISP): 328.2 ([M+H]$^+$).

Example 28

N-[4-(azetidin-3-yloxy)-3-fluoro-phenyl]-6-ethoxypyridine-3-carboxamide

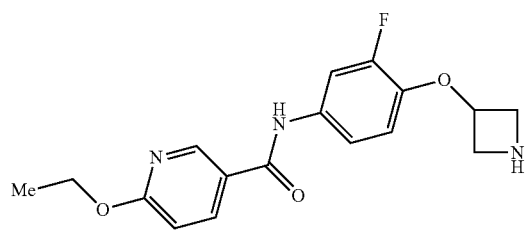 [SMILES: CCOc1ccc(C(=O)Nc2ccc(OC3CNC3)c(F)c2)cn1]

The title compound was obtained in analogy to example 25 using 6-ethoxynicotinic acid (CAS 97455-65-7) in place of 4-chloro-3-cyclopropyl-1H-pyrazole-5-carboxylic acid in step (c). White powder. MS (ISP): 332.3 ([M+H]$^+$).

Example 29

N-[4-(azetidin-3-yloxy)phenyl]-4-chloro-2-methyl-5-(trifluoromethyl)pyrazole-3-carboxamide

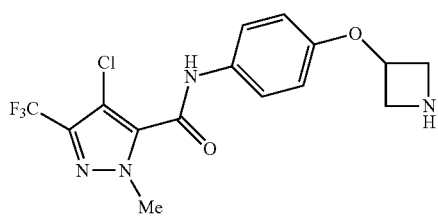 [SMILES: Cn1nc(C(F)(F)F)c(Cl)c1C(=O)Nc1ccc(OC2CNC2)cc1]

The title compound was obtained in analogy to example 19 using 4-chloro-1-methyl-3-(trifluoromethyl)-1H-pyrazole-5-carboxylic acid (CAS 128694-71-3) in place of 2-(2,2,2-trifluoroethoxy)pyrimidine-5-carboxylic acid in step (a). White powder. MS (ISP): 377.2 ([$\{^{37}Cl\}$M+H]$^+$), 375.2 ([$\{^{35}Cl\}$M+H]$^+$).

Example 30

4-(azetidin-3-yloxy)-N-(6-chloropyridin-3-yl)benzamide

The title compound was obtained in analogy to example 18 using 6-chloropyridin-3-amine (CAS 5350-93-6) in place of 4-fluorobenzylamine in step (c). White powder. MS (ISP): 306.2 ([$\{^{37}Cl\}$M+H]$^+$), 304.2 ([$\{^{35}Cl\}$M+H]$^+$).

Example 31

N-[4-(azetidin-3-yloxy)phenyl]-4-bromo-3-cyclopropyl-1H-pyrazole-5-carboxamide

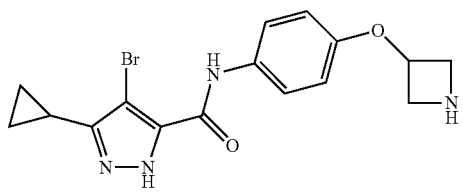

The title compound was obtained in analogy to example 19 using 4-bromo-3-cyclopropyl-1H-pyrazole-5-carboxylic acid in place of 2-(2,2,2-trifluoroethoxy)pyrimidine-5-carboxylic acid in step (a). White powder. MS (ISP): 379.2 ([$\{^{81}Br\}$M+H]$^+$), 377.1 ([$\{^{79}Br\}$M+H]$^+$).

Example 32

N-[4-(azetidin-3-yloxy)phenyl]-3-tert-butyl-4-chloro-1H-pyrazole-5-carboxamide

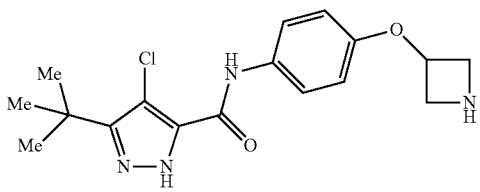 [SMILES: CC(C)(C)c1n[nH]c(C(=O)Nc2ccc(OC3CNC3)cc2)c1Cl]

The title compound was obtained in analogy to example 19 using 3-tert-butyl-4-chloro-1H-pyrazole-5-carboxylic acid in place of 2-(2,2,2-trifluoroethoxy)pyrimidine-5-carboxylic acid in step (a). White powder. MS (ISP): 351.2 ([$\{^{37}Cl\}$M+H]$^+$), 349.2 ([$\{^{35}Cl\}$M+H]$^+$).

Example 33

N-[4-(azetidin-3-yloxy)phenyl]-4-chloro-3-isopropyl-1H-pyrazole-5-carboxamide

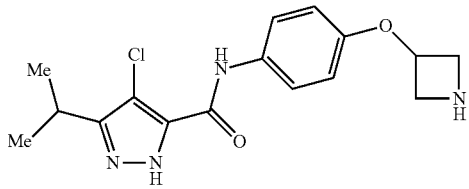 [SMILES: CC(C)c1n[nH]c(C(=O)Nc2ccc(OC3CNC3)cc2)c1Cl]

The title compound was obtained in analogy to example 19 using 4-chloro-3-isopropyl-1H-pyrazole-5-carboxylic acid in place of 2-(2,2,2-trifluoroethoxy)pyrimidine-5-carboxylic acid in step (a). White powder. MS (ISP): 337.2 ([$\{^{37}Cl\}$M+H]$^+$), 335.2 ([$\{^{35}Cl\}$M+H]$^+$).

Example 34

N-[4-(azetidin-3-yloxy)phenyl]-4-chloro-3-(4-chlorophenyl)-1H-pyrazole-5-carboxamide

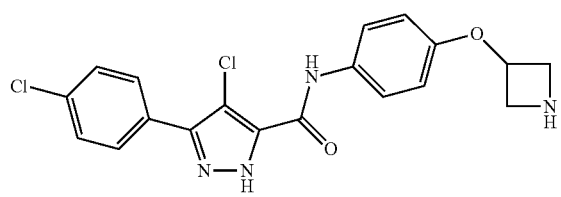 [SMILES: O=C(Nc1ccc(OC2CNC2)cc1)c1[nH]nc(-c2ccc(Cl)cc2)c1Cl]

The title compound was obtained in analogy to example 19 using 4-chloro-3-(4-chlorophenyl)-1H-pyrazole-5-carboxylic acid in place of 2-(2,2,2-trifluoroethoxy)pyrimidine-5-carboxylic acid in step (a). White powder. MS (ISP): 405.3 ([$\{^{37}Cl\}$M+H]$^+$), 403.1 ([$\{^{35}Cl\}$M+H]$^+$).

Example 35

N-[4-(azetidin-3-ylsulfanyl)phenyl]-4-chloro-3-cyclopropyl-1H-pyrazole-5-carboxamide

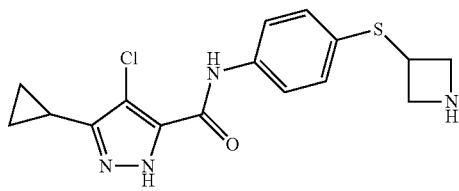

a) 1-benzhydryl-3-(4-bromophenylthio)azetidine

To a stirred solution of 4-bromobenzenethiol (1.43 g, 7.56 mmol) in DMF (12 mL) at 0° C. was added NaH (90.7 mg, 1.89 mmol, 60% in mineral oil). The reaction mixture was stirred for 15 min then 1-benzhydrylazetidin-3-yl methanesulfonate (2.0 g, 6.3 mmol) in DMF (10 mL) was added via syringe. The reaction mixture was heated to 60° C. overnight before being poured into water and extracted with EtOAc. The combined organic extracts were washed with water, dried ($Na_2SO_4$) and concentrated in vacuo. The residue was purified by flash column chromatography (silica gel, gradient: 0% to 25% EtOAc in heptane) to afford the title compound (1.62 g, 63%) as a white solid. MS (ISP): 412.2 ($[\{^{81}Br\}M+H]^+$), 410.1 ($[\{^{79}Br\}M+H]^+$).

b) 3-(4-bromophenylthio)azetidinium chloride

To a stirred solution of 1-benzhydryl-3-(4-bromophenylthio)azetidine (1.58 g, 3.87 mmol) in 1,2-dichloroethane (20 mL) was added 1-chloroethyl chloroformate (719 mg, 543 µL, 5.03 mmol). The reaction mixture was heated at reflux for 2 hours before cooling to room temperature. Methanol (20 mL) was added and reaction mixture was heated at reflux for further 2 hours then cooled to room temperature and concentrated in vacuo. The crude residue was triturated with diethyl ether then filtered and dried under high vacuum to afford the title compound as a white solid (1.17 g, 92%). MS (ISP): 246.0 ($[\{^{81}Br\}M+H]^+$), 244.0 ($[\{^{79}Br\}M+H]^+$).

c) tert-butyl 3-(4-bromophenylthio)azetidine-1-carboxylate

To a stirred solution of 3-(4-bromophenylthio)azetidinium chloride (1.15 g, 4.1 mmol) in methanol (25 mL) was added N,N-diisopropylethylamine (1.43 mL, 8.2 mmol). After 15 min, di-tert-butyl dicarbonate (1.79 g, 8.2 mmol) was added and the reaction was stirred overnight. The reaction was quenched by addition of water then extracted with ethyl acetate. The combined organic extracts were washed with brine, dried ($Na_2SO_4$) and concentrated in vacuo. The crude material was purified by flash chromatography (silica gel, gradient: 0% to 20% EtOAc in heptane) to afford the title compound as a white solid (0.933 g, 66%). MS (ISP): 290.1 ($[\{^{81}Br\}M-C_4H_8+H]^+$), 288.0 ($[\{^{79}Br\}M-C_4H_8+H]^+$).

d) tert-butyl 3-(4-(diphenylmethyleneamino)phenylthio)azetidine-1-carboxylate A microwave vial was charged with tert-butyl 3-(4-bromophenylthio)azetidine-1-carboxylate (926 mg, 2.69 mmol), diphenylmethanimine (536 mg, 2.96 mmol), sodium tert-butoxide (414 mg, 4.31 mmol), rac-2,2'-bis(diphenylphosphino)-1,1'-binaphthyl (168 mg, 269 µmol), $Pd_2(dba)_3$ (73.9 mg, 80.7 µmol) and dry toluene (6.5 mL). The resulting mixture was degassed for 5 min by bubbling nitrogen through the reaction medium. The reaction was heated to 90° C. overnight and then filtered directly through a pad of dicalite. The filter cake was rinsed with EtOAc and the filtrate concentrated in vacuo. The crude residue was purified by flash chromatography (silica gel, gradient: 0% to 20% EtOAc in heptane) to afford the title compound (1.11 g, 93%) as a yellow foam. MS (ISP): 445.2 ($[M+H]^+$).

e) tert-butyl 3-(4-aminophenylthio)azetidine-1-carboxylate

To a stirred solution of tert-butyl 3-(4-(diphenylmethyleneamino)phenylthio)azetidine-1-carboxylate (1.11 g, 2.5 mmol) in methanol (14 mL) was added under nitrogen sodium acetate (616 mg, 7.51 mmol) and hydroxylamine hydrochloride (383 mg, 5.51 mmol). The reaction mixture was stirred at 50° C. overnight. The resulting white precipitate was filtered off, while the filtrate was concentrated in vacuo and purified by flash chromatography (silica gel, gradient: 0% to 60% EtOAc in heptane) to afford the title compound (647 mg, 92%) as a pink crystalline solid. MS (ISP): 225.1 ($[M-C_4H_8+H]^+$).

f) tert-butyl 3-[4-[(4-chloro-3-cyclopropyl-1H-pyrazole-5-carbonyl)amino]phenyl]sulfonylazetidine-1-carboxylate To a stirred solution of tert-butyl 3-(4-aminophenylthio)azetidine-1-carboxylate (30 mg, 107 mol) in DMF (500 µL) under nitrogen was added the 4-chloro-3-cyclopropyl-1H-pyrazole-5-carboxylic acid (139 µmol), N-methylmorpholine (35.3 µL, 321 µmol) and HBTU (60.8 mg, 160 µmol). The reaction mixture was stirred overnight at room temperature before being quenched by addition of saturated aqueous $NH_4Cl$. The reaction mixture was poured into water and extracted with EtOAc. The combined organic extracts were washed with saturated $NaHCO_3$, brine, dried ($Na_2SO_4$) and concentrated in vacuo. The residue was purified by flash chromatography (silica gel, gradient: 0% to 50% EtOAc in heptane) to afford the title compound (35 mg, 72%) as a white powder. MS (ISP): 395.4 ($[\{^{37}Cl\}M-C_4H_8+H]^+$), 393.5 ($[\{^{35}Cl\}M-C_4H_8+H]^+$).

g) N-[4-(azetidin-3-ylsulfanyl)phenyl]-4-chloro-3-cyclopropyl-1H-pyrazole-5-carboxamide 2,2,2-trifluoroacetic acid To a stirred solution of tert-butyl 3-[4-[(4-chloro-3-cyclopropyl-1H-pyrazole-5-carbonyl)amino]phenyl]sulfanylazetidine-1-carboxylate (35 mg, 77 µmol) in $CH_2Cl_2$ (1 mL) was added 2,2,2-trifluoroacetic acid (0.5 mL). The reaction mixture was stirred for 2 hours at room temperature before all volatiles were removed under high vacuum. The residue was triturated with diethyl ether, filtered and dried under high vacuum to afford the title compound (23.3 mg, 65%) as a white powder. MS (ISP): 351.3 ($[\{^{37}Cl\}M+H]^+$), 349.4 ($[\{^{35}Cl\}M+H]^+$).

Example 36

N-[4-(azetidin-3-yloxy)-2-fluoro-phenyl]-4-chloro-3-cyclopropyl-1H-pyrazole-5-carboxamide

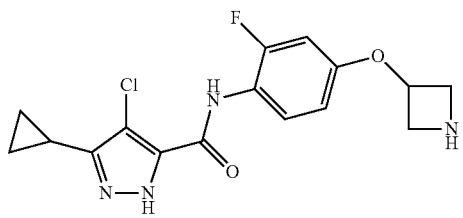 [SMILES: O=C(Nc1ccc(OC2CNC2)cc1F)c1[nH]nc(C2CC2)c1Cl]

The title compound was obtained in analogy to example 35 using 4-bromo-3-fluorophenol (CAS 121219-03-2) in place of 4-bromobenzenethiol in step (a). Off-white powder. MS (ISP): 353.1 ([{$^{37}$Cl}M+H]$^+$), 351.1 ([{$^{35}$Cl}M+H]$^+$).

Example 37

4-(azetidin-3-yloxy)-N-(4-chloro-3-(trifluoromethyl)phenyl)benzamide

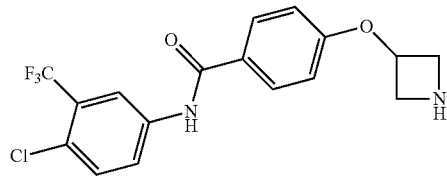 [SMILES: O=C(Nc1ccc(Cl)c(C(F)(F)F)c1)c1ccc(OC2CNC2)cc1]

The title compound was obtained in analogy to example 18 using 4-chloro-3-(trifluoromethyl)aniline (CAS 320-51-4) in place of 4-fluorobenzylamine in step (c). White powder. MS (ISP): 373.5 ([{$^{37}$Cl}M+H]$^+$), 371.5 ([{$^{35}$Cl}M+H]$^+$).

Example 38

N-[4-(azetidin-3-yloxy)-2-fluoro-phenyl]-2-cyclopropyl-pyrimidine-5-carboxamide

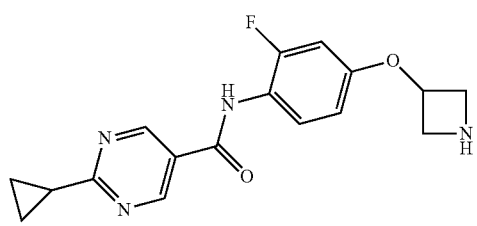 [SMILES: O=C(Nc1ccc(OC2CNC2)cc1F)c1cnc(C2CC2)nc1]

The title compound was obtained in analogy to example 35 using 4-bromo-3-fluorophenol (CAS 121219-03-2) in place of 4-bromobenzenethiol in step (a) and 2-cyclopropylpyrimidine-5-carboxylic acid (CAS 648423-79-4) in place of 4-chloro-3-cyclopropyl-1H-pyrazole-5-carboxylic acid in step (f). Off-white powder. MS (ISP): 329.3 ([M+H]$^+$).

Example 39

N-[4-(azetidin-3-yloxy)-2-fluoro-phenyl]-2-(trifluoromethyl)pyrimidine-5-carboxamide

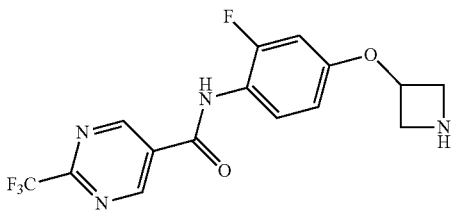 [SMILES: O=C(Nc1ccc(OC2CNC2)cc1F)c1cnc(C(F)(F)F)nc1]

The title compound was obtained in analogy to example 35 using 4-bromo-3-fluorophenol (CAS 121219-03-2) in place of 4-bromobenzenethiol in step (a) and 2-(trifluoromethyl)pyrimidine-5-carboxylic acid (CAS 306960-74-7) in place of 4-chloro-3-cyclopropyl-1H-pyrazole-5-carboxylic acid in step (f). Off-white powder. MS (ISP): 357.2 ([M+H]$^+$)

Example 40

N-[4-(azetidin-3-yloxy)phenyl]-4-chloro-3-(trifluoromethyl)-1H-pyrazole-5-carboxamide

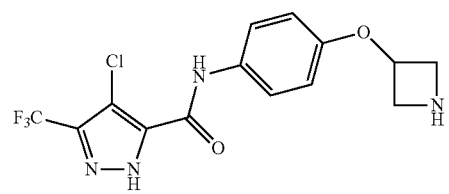 [SMILES: O=C(Nc1ccc(OC2CNC2)cc1)c1[nH]nc(C(F)(F)F)c1Cl]

The title compound was obtained in analogy to example 10 using 4-chloro-3-(trifluoromethyl)-1H-pyrazole-5-carboxylic acid in place of 3-cyclopropyl-1H-pyrazole-5-carboxylic acid in step (a). White powder. MS (ISP): 363.1 ([{$^{37}$Cl}M+H]$^+$), 361.2 ([{$^{35}$Cl}M+H]$^+$).

Example 41

N-[4-(azetidin-3-yloxy)phenyl]-4-chloro-3-ethyl-1H-pyrazole-5-carboxamide

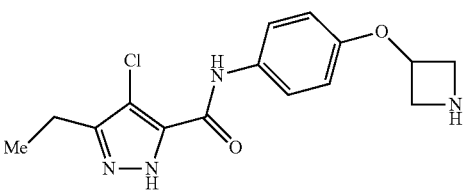 [SMILES: CCc1n[nH]c(C(=O)Nc2ccc(OC3CNC3)cc2)c1Cl]

The title compound was obtained in analogy to example 10 using 4-chloro-3-ethyl-1H-pyrazole-5-carboxylic acid in place of 3-cyclopropyl-1H-pyrazole-5-carboxylic acid in step (a). White powder. MS (ISP): 323.1 ([{$^{37}$Cl}M+H]$^+$), 321.2 ([{$^{35}$Cl}M+H]$^+$).

Example 42

N-[4-(azetidin-3-yloxy)phenyl]-3-cyclopropyl-4-fluoro-1H-pyrazole-5-carboxamide

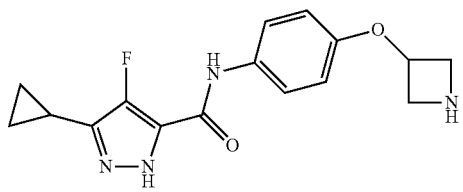

The title compound was obtained in analogy to example 10 using 3-cyclopropyl-4-fluoro-1H-pyrazole-5-carboxylic acid in place of 3-cyclopropyl-1H-pyrazole-5-carboxylic acid in step (a). White powder. MS (ISP): 317.3 ([M+H]$^+$).

Example 43

N-[4-(azetidin-3-yloxy)phenyl]-4-chloro-1-methyl-5-(trifluoromethyl)pyrazole-3-carboxamide

The title compound was obtained in analogy to example 10 using 4-chloro-1-methyl-5-(trifluoromethyl)-1H-pyrazole-3-carboxylic acid in place of 3-cyclopropyl-1H-pyrazole-5-carboxylic acid in step (a). White powder. MS (ISP): 377.1 ([{$^{37}$Cl}M+H]$^+$), 375.0 ([{$^{35}$Cl}M+H]$^+$).

Example 44

N-[4-(azetidin-3-ylsulfanyl)phenyl]-2-cyclopropyl-pyrimidine-5-carboxamide

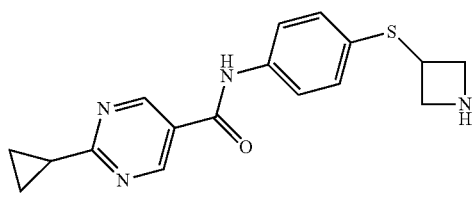

The title compound was obtained in analogy to example 35 using 2-cyclopropylpyrimidine-5-carboxylic acid (CAS 648423-79-4) in place of 4-chloro-3-cyclopropyl-1H-pyrazole-5-carboxylic acid in step (f). Off-white powder. MS (ISP): 327.4 ([M+H]$^+$).

Example 45

N-[4-(azetidin-3-ylsulfanyl)phenyl]-2-(trifluoromethyl)pyrimidine-5-carboxamide

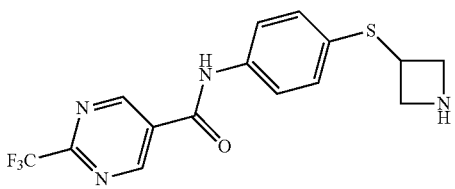 [SMILES: O=C(Nc1ccc(SC2CNC2)cc1)c1cnc(C(F)(F)F)nc1]

The title compound was obtained in analogy to example 35 using 2-(trifluoromethyl)pyrimidine-5-carboxylic acid (CAS 306960-74-7) in place of 4-chloro-3-cyclopropyl-1H-pyrazole-5-carboxylic acid in step (f). Off-white powder. MS (ISP): 355.3 ([M+H]$^+$).

Example 46

3-benzyl-3-fluoro-azetidine

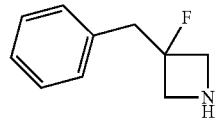 [SMILES: FC1(Cc2ccccc2)CNC1]

a) 1-benzhydryl-3-benzylazetidin-3-ol

To a solution of 1-benzhydrylazetidin-3-one (2.0 g, 8.43 mmol, CAS 40320-60-3) in THF (55 mL) at −78° C. was added a solution of benzylmagnesium chloride in THF (1.5 M, 8.43 mL, 12.6 mmol). After 20 min, the reaction mixture was allowed to warm to room temperature overnight. The reaction mixture was quenched by careful addition of water and saturated aqueous Na/K tartrate. After stirring for 30 min, the resultant suspension was filtered and the filtrate was extracted with EtOAc. The combined organic extracts were washed with brine, dried (Na$_2$SO$_4$) and concentrated in vacuo. The crude material was purified by flash chromatography (silica gel, 0% to 25% EtOAc in heptane) to afford the title compound (2.13 g, 76%) as a white solid. MS (ISP): 330.1 ([M+H]$^+$).

b) 1-benzhydryl-3-benzyl-3-fluoroazetidine

To a stirred solution of 1-benzhydryl-3-benzylazetidin-3-ol (1.4 g, 4.25 mmol) in CH$_2$Cl$_2$ (20 mL) at −78° C. was added Deoxo-Fluor™ in toluene (50 wt. %, 1.89 mL, 5.1 mmol). After 15 min, the reaction was allowed to warm to room temperature and stirred for further 30 min before being quenched by addition of aqueous sodium bicarbonate. The reaction mixture was poured into water and extracted with CH$_2$Cl$_2$. The combined organic extracts were washed with brine, dried (Na$_2$SO$_4$) and concentrated in vacuo. The residue was purified by flash chromatography (silica gel, gradient: 0% to 10% EtOAc in heptane) followed up by preparative HPLC (mobile phase A: H$_2$O, B: CH$_3$CN with 0.05% Et$_3$N, C18 column) to afford the title compound (764 mg, 54%) as a white solid. MS (ISP): 332.1 ([M+H]$^+$).

c) 3-benzyl-3-fluoroazetidinium chloride

To a stirred solution of 1-benzhydryl-3-benzyl-3-fluoroazetidine (315 mg, 950 µmol) in methanol (9 mL) under nitrogen was added aqueous HCl (3.0 M, 380 µL, 1.14 mmol) and 10 wt. % Pd/C (50.6 mg, 47.5 µmol). The resulting black suspension was purged by evacuation and then back filled with a stream of hydrogen (balloon) for three times. The mixture was stirred for 16 hours at room temperature under hydrogen atmosphere. The resulting suspension was filtered directly through a plug of dicalite. The filter cake was rinsed with methanol and the filtrate was concentrated in vacuo. The residue was triturated with diethyl ether, filtered and dried under high vacuum to afford the title compound (182 mg, 95%) as a light green powder. MS (ISP): 166.1 ([M+H]+).

Example 47

N-[4-(azetidin-3-yloxy)phenyl]-4-bromo-3-ethyl-1H-pyrazole-5-carboxamide

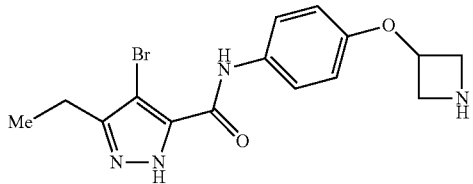 [SMILES: CCc1n[nH]c(C(=O)Nc2ccc(OC3CNC3)cc2)c1Br]

The title compound was obtained in analogy to example 10 using 4-bromo-3-ethyl-1H-pyrazole-5-carboxylic acid in place of 3-cyclopropyl-1H-pyrazole-5-carboxylic acid in step (a). White powder. MS (ISP): 367.3 ([{81Br}M+H]+), 365.3 ([{79Br}M+H]+).

Example 48

N-[4-(azetidin-3-yloxy)phenyl]-4-bromo-3-methyl-1H-pyrazole-5-carboxamide

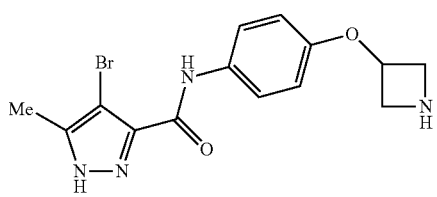 [SMILES: Cc1[nH]nc(C(=O)Nc2ccc(OC3CNC3)cc2)c1Br]

The title compound was obtained in analogy to example 10 using 4-bromo-3-methyl-1H-pyrazole-5-carboxylic acid in place of 3-cyclopropyl-1H-pyrazole-5-carboxylic acid in step (a). White powder. MS (ISP): 353.2 ([{81Br}M+H]+), 351.2 ([{79Br}M+H]+).

Example 49

3-[(4-bromophenyl)-difluoro-methyl]azetidine

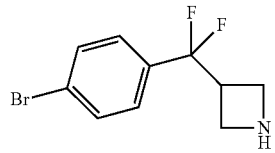 [SMILES: FC(F)(c1ccc(Br)cc1)C1CNC1]

a) tert-butyl 3-(methoxy(methyl)carbamoyl)azetidine-1-carboxylate

To a stirred solution of 1-(tert-butoxycarbonyl)azetidine-3-carboxylic acid (3.0 g, 14.9 mmol, CAS 142253-55-2) in DMF (45 mL) at room temperature was added N,O-dimethyl hydroxylamine hydrochloride (1.75 g, 17.9 mmol), HBTU (8.48 g, 22.4 mmol) and N-methyl morpholine (6.56 mL, 59.6 mmol). After 16 hours, the reaction mixture was poured into a 1:1 mixture of water and saturated NH4Cl and extracted with EtOAc. The combined organic extracts were washed with saturated aqueous NaHCO3 and brine, dried (Na2SO4) and concentrated in vacuo to afford the title compound (2.9 g, 80%) as a colorless oil. MS (ISP): 189.1 ([M-C4H8+H]+).

b) tert-butyl 3-(4-bromobenzoyl)azetidine-1-carboxylate

To stirred solution of 1,4-dibromobenzene (5.07 g, 21.5 mmol, CAS 106-37-6) in dry THF (25 mL) at −78° C. was added BuLi (1.6 M in hexane, 13.4 mL, 21.5 mmol). The reaction was allowed to warm up to −25° C. for 30 min before being transferred via cannula to a solution of tert-butyl 3-(methoxy(methyl)carbamoyl)azetidine-1-carboxylate (3.5 g, 14.3 mmol) in THF (25 mL) at −78° C. After 90 min, the reaction was allowed to warm to −25° C. before being quenched by addition of saturated aqueous NH4Cl. The reaction was poured into water and extracted with EtOAc. The combined organic extracts were washed with brine, dried (Na2SO4) and concentrated in vacuo. The residue was purified by flash chromatography (silica gel, gradient: 0% to 30% EtOAc in heptane) to afford the title compound (3.03 g, 62%) as a white solid. MS (ISP): 286.1 ([{81Br}M-C4H8+H]+), 284.2 ([{79Br}M-C4H8+H]+).

c) tert-butyl 3-((4-bromophenyl)difluoromethyl)azetidine-1-carboxylate

To a stirred solution of tert-butyl 3-(4-bromobenzoyl)azetidine-1-carboxylate (1.0 g, 2.94 mmol) in CH2Cl2 (15 mL) was added Deoxo-Fluor™ in toluene (50 wt. %, 10.9 mL, 29.4 mmol). The reaction mixture was stirred for 5 days at room temperature. Upon completion, the reaction was poured into ice and saturated aqueous NaHCO3 and extracted with CH2Cl2. The combined organic extracts were washed with brine, dried (Na2SO4) and concentrated in vacuo. The residue was purified by flash chromatography (silica gel, gradient: 0% to 15% EtOAc in heptane) to afford the title compound (844 mg, 79%) as a colorless oil. MS (ISP): 308.1 ([{81Br}M-C4H8+H]+), 306.1 ([{79Br}M-C4H8+H]+).

c) 3-[(4-bromophenyl)-difluoro-methyl]azetidine 2,2,2-trifluoroacetic acid

To a stirred solution of tert-butyl 3-((4-bromophenyl)difluoromethyl)azetidine-1-carboxylate (58.5 µmol) in CH₂Cl₂ (1.0 mL) was added 2,2,2-trifluoroacetic acid (0.5 mL). The reaction mixture was stirred for 2 hours at room temperature before all volatiles were removed under high vacuum. The residue was triturated with diethyl ether, filtered and dried under high vacuum to afford the title compound as a white powder (18.3 mg, 83%). MS (ISP): 264.0 ([{$^{81}$Br}M+H]$^+$), 262.1 ([{$^{79}$Br}M+H]$^+$).

Example 50

3-[(4-bromophenyl)methylene]azetidine

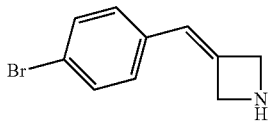 [SMILES: Brc1ccc(C=C2CNC2)cc1]

a) tert-butyl 3-(4-bromobenzylidene)azetidine-1-carboxylate

To a solution of (4-bromobenzyl)triphenylphosphonium bromide (3.29 g, 6.43 mmol, CAS 51044-13-4) in DMF (40 mL) at 0° C. was added NaH (280 mg, 6.43 mmol, 60% in mineral oil). After 15 min, tert-butyl 3-oxoazetidine-1-carboxylate (1.0 g, 5.84 mmol, CAS 398489-26-4) in DMF (8 mL) was added via syringe. The reaction mixture was heated to 65° C. overnight before being quenched by addition of saturated aqueous NH₄Cl. The reaction was poured into water and extracted with ethyl acetate. The combined organic extracts were washed with brine, dried (Na₂SO₄) and concentrated in vacuo. The residue was purified by flash chromatography (silica gel, gradient: 0% to 15% EtOAc in heptane) to afford the title compound (1.42 g, 75%) as a white solid. MS (ISP): 270.1 ([{$^{81}$Br}M-C₄H₈+H]$^+$), 268.1 ([{$^{79}$Br}M-C₄H₈+H]$^+$).

b) 3-[(4-bromophenyl)methylene]azetidine 2,2,2-trifluoroacetic acid

To a stirred solution of tert-butyl 3-(4-bromobenzylidene)azetidine-1-carboxylate (74 µmol) in CH₂Cl₂ (1.0 mL) was added 2,2,2-trifluoroacetic acid (0.5 mL). The reaction mixture was stirred for 2 hours at room temperature before all volatiles were removed under high vacuum. The residue was triturated with diethyl ether, filtered and dried under high vacuum to afford the title compound as a white powder (18.3 mg, 83%). MS (ISP): 226.0 ([{$^{81}$Br}M+H]$^+$), 224.1 ([{$^{79}$Br}M+H]$^+$).

Example 51

N-[4-[azetidin-3-yl(difluoro)methyl]phenyl]-4-chloro-benzamide

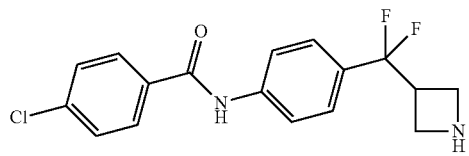 [SMILES: O=C(Nc1ccc(C(F)(F)C2CNC2)cc1)c1ccc(Cl)cc1]

a) tert-butyl 3-((4-(4-chlorobenzamido)phenyl)difluoromethyl)azetidine-1-carboxylate A microwave vial was charged with tert-butyl 3-((4-bromophenyl)difluoromethyl)azetidine-1-carboxylate (55 mg, 152 µmol), 4-chlorobenzamide (26.0 mg, 167 µmol, CAS 619-56-7), 4,5-bis(diphenylphosphino)-9,9-dimethylxanthene (1.76 mg, 3.04 µmol), Pd₂(dba)₃ (1.39 mg, 1.52 mol), K₃PO₄ (48.3 mg, 228 µmol) and dry 1,4-dioxane (0.75 mL). The resulting mixture was degassed for 5 min by bubbling nitrogen through the reaction mixture. The reaction was heated to 100° C. overnight and then filtered directly through a pad of dicalite. The filter cake was rinsed with EtOAc and the filtrate concentrate in vacuo. The crude residue was purified by flash chromatography (silica gel, gradient: 0% to 20% EtOAc in heptane) to afford the title compound (117 mg, 90%) as a light-brown solid. MS (ISP): 437.1 ([{$^{37}$Cl}M−H]$^−$), 435.0 ([{$^{35}$Cl}M−H]$^−$).

b) N-[4-[azetidin-3-yl(difluoro)methyl]phenyl]-4-chloro-benzamide 2,2,2-trifluoroacetic acid To a stirred solution of tert-butyl 3-((4-(4-chlorobenzamido)phenyl)difluoromethyl)azetidine-1-carboxylate (93.8 µmol) in CH₂Cl₂ (1.0 mL) was added 2,2,2-trifluoroacetic acid (0.5 mL). The reaction mixture was stirred for 2 hours at room temperature before all volatiles were removed under high vacuum. The residue was triturated with diethyl ether, filtered and dried under high vacuum to afford the title compound as a white powder (35 mg, 82%). MS (ISP): 339.1 ([{$^{37}$Cl}M+H]$^+$), 337.0 ([{$^{35}$Cl}M+H]$^+$).

Example 52

4-chloro-N-[4-[(3-fluoroazetidin-3-yl)methyl]phenyl]benzamide

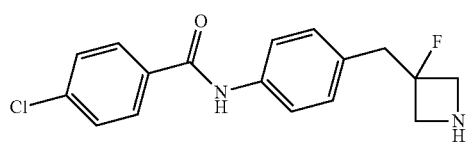 [SMILES: O=C(Nc1ccc(CC2(F)CNC2)cc1)c1ccc(Cl)cc1]

a) 3-fluoro-3-[(4-nitrophenyl)methyl]azetidine

To a stirred solution of 3-benzyl-3-fluoroazetidinium chloride (420 mg, 2.08 mmol) in sulfuric acid (1.67 mL, 31.2 mmol) at 0° C. was added CH₂Cl₂ (1 mL). The reaction mixture was cooled to −20° C. then nitric acid (158 µL, 2.29 mmol, 65 wt. %) was added. The reaction was allowed to warm to 0° C. then stirred for further 30 min before being quenched by addition of NaOH (6.0M) to pH 10-11. The mixture was extracted with $CH_2Cl_2$ and the combined organic extracts were dried ($Na_2SO_4$) and concentrated in vacuo to afford the title compound (345 mg, 79%) as an orange solid which was used in the next step without further purification.

b) tert-butyl 3-fluoro-3-[(4-nitrophenyl)methyl]azetidine-1-carboxylate

To a stirred solution of 3-fluoro-3-[(4-nitrophenyl)methyl]azetidine (50 mg, 238 μmol) in methanol (2.5 mL) was added N,N-diisopropylethylamine (74.8 μL, 428 μmol). After 15 min, di-tert-butyl dicarbonate (93.4 mg, 428 μmol) was added and the reaction was stirred overnight. The reaction was poured into water and extracted with EtOAc. The combined organic extracts were washed with brine, dried ($Na_2SO_4$) and concentrated in vacuo. The crude material was purified by flash chromatography (silica gel, gradient: 0% to 20% EtOAc in heptane) to afford the title compound as a light brown solid (34 mg, 51%). MS (ISP): 255.2 ($[M-C_4H_8+H]^+$).

c) tert-butyl 3-(4-aminobenzyl)-3-fluoroazetidine-1-carboxylate

To a stirred solution of tert-butyl 3-fluoro-3-(4-nitrobenzyl)azetidine-1-carboxylate (28.7 mg, 92.5 μmol) in ethyl acetate (1 mL) under nitrogen atmosphere was added 10 wt. % Pd/C (4.62 mol). The resulting black suspension was purged by evacuation and then back filled with a stream of hydrogen (balloon) for three times. The mixture was stirred for 16 hours at room temperature under hydrogen atmosphere. The resulting suspension was filtered directly through a plug of dicalite. The filter cake was rinsed with EtOAc and the filtrate was concentrated in vacuo.

The residue was purified by flash chromatography (silica gel, gradient: 0% to 30% EtOAc in heptane) to afford the title compound as an orange oil (19 mg, 73%). MS (ISP): 225.2 ($[M-C_4H_8+H]^+$).

d) tert-butyl 3-(4-(4-chlorobenzamido)benzyl)-3-fluoroazetidine-1-carboxylate

To a stirred solution of tert-butyl 3-(4-aminobenzyl)-3-fluoroazetidine-1-carboxylate (20 mg, 71.3 μmol) in DMF (500 μL) at room temperature was added 4-chlorobenzoic acid (14.5 mg, 92.7 μmol, CAS 74-11-3), N-methylmorpholine (23.5 μL, 214 μmol) and HBTU (40.6 mg, 107 mol). The reaction mixture was stirred overnight at room temperature before being quenched by addition of saturated aqueous $NH_4Cl$. The reaction mixture was poured into water and extracted with EtOAc. The combined organic extracts were washed with saturated aqueous $NaHCO_3$, brine, dried ($Na_2SO_4$) and concentrated in vacuo. The residue was then purified by flash chromatography (silica gel, gradient: 0% to 20% EtOAc in heptane) to afford the title compound as a white solid (20 mg, 67%). MS (ISP): 419.1 ($[\{^{37}Cl\}M-H]^-$), 417.0 ($[\{^{35}Cl\}M-H]^-$).

e) 4-chloro-N-[4-[(3-fluoroazetidin-3-yl)methyl]phenyl]benzamide hydrochloride

To a stirred solution of tert-butyl 3-(4-(4-chlorobenzamido)benzyl)-3-fluoroazetidine-1-carboxylate (47.7 μmol) in $CH_2Cl_2$ (1.0 mL) was added 2,2,2-trifluoroacetic acid (0.5 mL). The reaction mixture was stirred for 2 hours at room temperature before all volatiles were removed under high vacuum. The residue was triturated with diethyl ether, filtered and dried under high vacuum to afford the title compound as a white powder (16 mg, 77%). MS (ISP): 321.4 ($[\{^{37}Cl\}M+H]^+$), 319.4 ($[\{^{35}Cl\}M+H]^+$).

Example 53

4-(azetidin-3-yloxy)-2-chloro-N-(6-chloro-3-pyridyl)benzamide

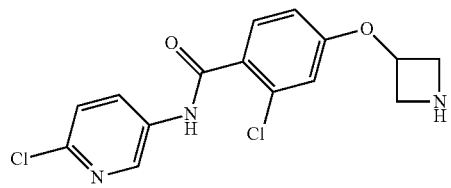 [SMILES: O=C(Nc1ccc(Cl)nc1)c1ccc(OC2CNC2)cc1Cl]

The title compound was obtained in analogy to example 18 using methyl 2-chloro-4-hydroxybenzoate in place of methyl 4-hydroxybenzoate in step (a) and 6-chloropyridin-3-amine (CAS 5350-93-6) in place of 4-fluorobenzylamine in step (c). White powder. MS (ISP): 339.7 ($[M+H]^+$).

Example 54

6-chloro-N-[4-[(3-fluoroazetidin-3-yl)methyl]phenyl]pyridine-3-carboxamide

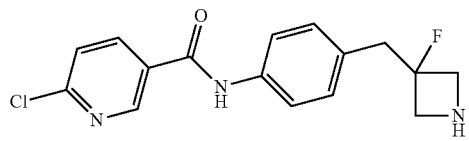 [SMILES: O=C(Nc1ccc(CC2(F)CNC2)cc1)c1ccc(Cl)nc1]

The title compound was obtained in analogy to example 52 using 6-chloronicotinic acid (CAS 5326-23-8) in place of 4-chlorobenzoic acid in step (d). White powder. MS (ISP): 322.2 ($[\{^{37}Cl\}M+H]^+$), 320.2 ($[\{^{35}Cl\}M+H]^+$).

Example 55

N-[4-[(3-fluoroazetidin-3-yl)methyl]phenyl]-2-(trifluoromethyl)pyrimidine-5-carboxamide

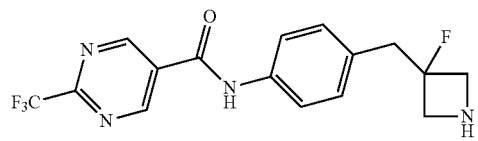 [SMILES: O=C(Nc1ccc(CC2(F)CNC2)cc1)c1cnc(C(F)(F)F)nc1]

The title compound was obtained in analogy to example 52 using 2-(trifluoromethyl)pyrimidine-5-carboxylic acid (CAS 306960-74-7) in place of 4-chlorobenzoic acid in step (d). White powder. MS (ISP): 355.1 ([M+H]+).

Example 56

4-chloro-3-cyclopropyl-N-[4-[(3-fluoroazetidin-3-yl)methyl]phenyl]-1H-pyrazole-5-carboxamide

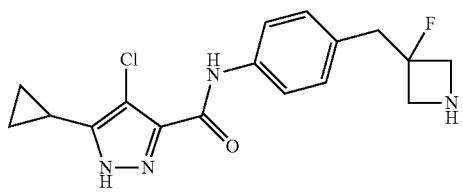 [SMILES: O=C(Nc1ccc(CC2(F)CNC2)cc1)c1n[nH]c(C2CC2)c1Cl]

The title compound was obtained in analogy to example 52 using 4-chloro-3-cyclopropyl-1H-pyrazole-5-carboxylic acid in place of 4-chlorobenzoic acid in step (d). White powder. MS (ISP): 351.1 ([{$^{37}$Cl}M+H]+), 349.1 ([{$^{35}$Cl}M+H]+).

Example 57

N-[4-[(3-fluoroazetidin-3-yl)methyl]phenyl]-5-(2,2,2-trifluoroethoxy)pyrazine-2-carboxamide

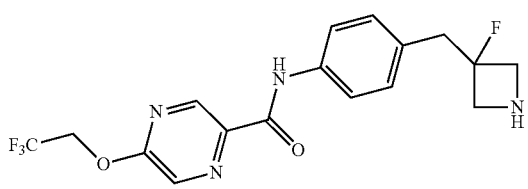 [SMILES: O=C(Nc1ccc(CC2(F)CNC2)cc1)c1cnc(OCC(F)(F)F)cn1]

The title compound was obtained in analogy to example 52 using 5-(2,2,2-trifluoroethoxy)pyrazine-2-carboxylic acid in place of 4-chlorobenzoic acid in step (d). White powder. MS (ISP): 385.2 ([M+H]+).

Example 58

N-[4-(azetidin-3-ylidenemethyl)phenyl]-4-chloro-3-cyclopropyl-1H-pyrazole-5-carboxamide

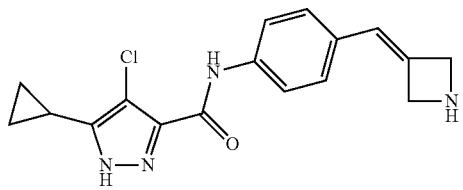 [SMILES: O=C(Nc1ccc(C=C2CNC2)cc1)c1n[nH]c(C2CC2)c1Cl]

a) tert-butyl 3-(4-(diphenylmethyleneamino)benzylidene)azetidine-1-carboxylate

A microwave vial was charged with tert-butyl 3-(4-bromobenzylidene)azetidine-1-carboxylate (200 mg, 617 µmol), benzophenone imine (123 mg, 679 µmol,), sodium tert-butoxide (94.9 mg, 987 µmol), rac-2,2'-bis(diphenylphosphino)-1,1'-binaphthyl (38.4 mg, 61.7 µmol), Pd$_2$(dba)$_3$ (16.9 mg, 18.5 µmol) and dry toluene (1.5 mL). The reaction mixture was degassed for 5 min by bubbling nitrogen through the reaction medium. The reaction was heated to 90° C. overnight and then filtered directly through a pad of dicalite. The filter cake was rinsed with EtOAc and the filtrate concentrated in vacuo. The crude residue was purified by flash chromatography (silica gel, gradient: 0% to 40% EtOAc in heptane) to afford the title compound (258 mg, 98%) as a yellow foam. MS (ISP): 425.4 ([M+H]+).

b) tert-butyl 3-(4-aminobenzylidene)azetidine-1-carboxylate

To a stirred solution of tert-butyl 3-(4-(diphenylmethyleneamino)benzylidene)azetidine-1-carboxylate (250 mg, 589 µmol) in methanol (9 mL) was added under a nitrogen atmosphere sodium acetate (145 mg, 1.77 mmol) and hydroxylamine hydrochloride (90.0 mg, 1.3 mmol).

The reaction mixture was stirred at 50° C. overnight. The resulting white precipitate was filtered off, while the filtrate was concentrated in vacuo and purified by flash chromatography (silica gel, gradient: 0% to 80% EtOAc in heptane) to afford the title compound (136 mg, 88%) as a white solid. MS (ISP): 261.4 ([M+H]+).

c) tert-butyl 3-[[4-[(4-chloro-3-cyclopropyl-1H-pyrazole-5-carbonyl)amino]phenyl]methylene]azetidine-1-carboxylate To a stirred solution of tert-butyl 3-(4-aminobenzylidene)azetidine-1-carboxylate (25 mg, 96 mol) in DMF (500 µL) under nitrogen was added 4-chloro-3-cyclopropyl-1H-pyrazole-5-carboxylic acid (21.5 mg, 115 µmol), N-methylmorpholine (31.7 µL, 288 µmol) and HBTU (54.6 mg, 144 µmol). The reaction mixture was stirred overnight at room temperature before being quenched by addition of saturated aqueous NH$_4$Cl. The reaction mixture was poured into water and extracted with EtOAc. The combined organic extracts were washed with saturated NaHCO$_3$, brine, dried (Na$_2$SO$_4$) and concentrated in vacuo. The crude residue was purified by flash chromatography (silica gel, gradient: 0% to 50% EtOAc in heptane) to afford the title compound as a white solid (30 mg, 73%). MS (ISP): 429.3 ([{$^{37}$Cl}M-H]-), 427.2 ([{$^{35}$Cl}M-H]-).

d) N-[4-(azetidin-3-ylidenemethyl)phenyl]-4-chloro-3-cyclopropyl-1H-pyrazole-5-carboxamide 2,2,2-trifluoroacetic acid To a stirred solution of tert-butyl 3-[[4-[(4-chloro-3-cyclopropyl-1H-pyrazole-5-carbonyl)amino]phenyl]methylene]azetidine-1-carboxylate (70 µmol) in CH$_2$Cl$_2$ (1 mL) was added 2,2,2-trifluoroacetic acid (0.5 mL). The reaction mixture was stirred for 2 hours at room temperature before all volatiles were removed under high vacuum. The residue was triturated with diethyl ether, filtered and dried under high vacuum to afford the title compound as a white powder (22.7 mg, 73%). MS (ISP): 331.4 ([{$^{37}$Cl}M+H]+), 329.4 ([{$^{35}$Cl}M+H]+).

Example 59

N-[4-(azetidin-3-ylidenemethyl)phenyl]-2-(trifluoromethyl)pyrimidine-5-carboxamide

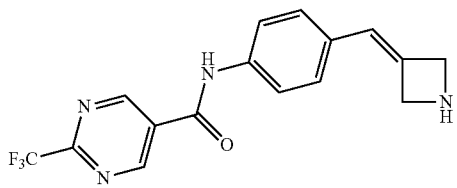 [SMILES: O=C(Nc1ccc(C=C2CNC2)cc1)c1cnc(C(F)(F)F)nc1]

The title compound was obtained in analogy to example 58 using 2-(trifluoromethyl)pyrimidine-5-carboxylic acid (CAS 306960-74-7) in place of 4-chloro-3-cyclopropyl-1H-pyrazole-5-carboxylic acid in step (c). White powder. MS (ISP): 335.2 ([M+H]$^+$).

Example 60

N-[4-(azetidin-3-ylidenemethyl)phenyl]-2-(trifluoromethyl)pyridine-4-carboxamide

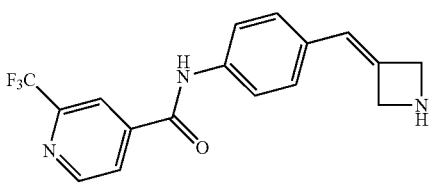 [SMILES: O=C(Nc1ccc(C=C2CNC2)cc1)c1ccnc(C(F)(F)F)c1]

The title compound was obtained in analogy to example 58 using 2-(trifluoromethyl)isonicotinic acid (CAS 131747-41-6) in place of 4-chloro-3-cyclopropyl-1H-pyrazole-5-carboxylic acid in step (c). White powder. MS (ISP): 334.2 ([M+H]$^+$).

Example 61

N-[4-(azetidin-3-ylidenemethyl)phenyl]-4-chlorobenzamide

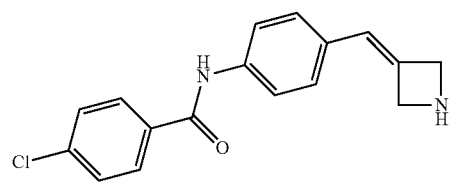 [SMILES: O=C(Nc1ccc(C=C2CNC2)cc1)c1ccc(Cl)cc1]

The title compound was obtained in analogy to example 58 using 4-chlorobenzoic acid (CAS 74-11-3) in place of 4-chloro-3-cyclopropyl-1H-pyrazole-5-carboxylic acid in step (c). White powder. MS (ISP): 301.3 ([{$^{37}$Cl}M+H]$^+$), 299.3 ([{$^{35}$Cl}M+H]$^+$).

Example 62

N-[4-(azetidin-3-ylidenemethyl)phenyl]-2-(trifluoromethyl)pyrimidin-4-amine

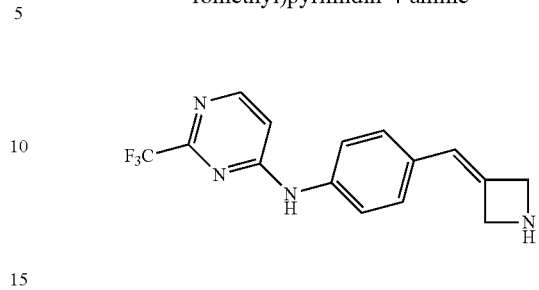

a) tert-butyl 3-[[4-[[2-(trifluoromethyl)pyrimidin-4-yl]amino]phenyl]methylene]azetidine-1-carboxylate A microwave vial was charged with tert-butyl 3-(4-aminobenzylidene)azetidine-1-carboxylate (25 mg, 96.0 µmol), 4-chloro-2-(trifluoromethyl)pyrimidine (17.7 mg, 97.0 µmol, CAS 1514-96-1), DMA (400 µL) and N,N-diisopropylethylamine (25.2 µL, 144 µmol). The reaction mixture was degassed for 5 min by bubbling nitrogen through the reaction medium. The vial was capped and heated in a microwave oven at 100° C. for 1 hour. The mixture was poured into water and extracted with EtOAc. The combined organic extracts were washed with brine, dried (Na$_2$SO$_4$) and concentrated in vacuo. The crude residue was purified by flash chromatography (silica gel, gradient: 0% to 30% EtOAc in heptane) to afford the title compound (14.7 mg, 38%) as a colourless oil. MS (ISP): 407.5 ([M+H]$^+$).

b) N-[4-(azetidin-3-ylidenemethyl)phenyl]-2-(trifluoromethyl)pyrimidin-4-amine 2,2,2-trifluoroacetic acid To a stirred solution of tert-butyl 3-[[4-[[2-(trifluoromethyl)pyrimidin-4-yl]amino]phenyl]methylene]azetidine-1-carboxylate (36.2 µmol) in CH$_2$Cl$_2$ (1.0 mL) was added 2,2,2-trifluoroacetic acid (0.5 mL). The reaction mixture was stirred for 2 hours at room temperature before all volatiles were removed under high vacuum. The residue was triturated with diethyl ether, filtered and dried under high vacuum to afford the title compound (10 mg, 63%) as a light brown powder. MS (ISP): 307.4 ([M+H]$^+$).

Example 63

N-[4-(azetidin-3-ylidenemethyl)phenyl]-5-(trifluoromethyl)pyrimidin-2-amine

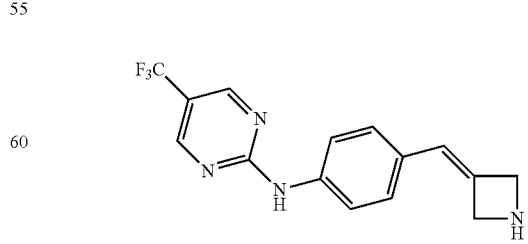

The title compound was obtained in analogy to example 62 using 2-chloro-5-(trifluoromethyl)pyrimidine (CAS 69034-12-4) in place of 4-chloro-2-(trifluoromethyl)pyrimidine in step (a). Light yellow powder. MS (ISP): 307.4 ([M+H]$^+$).

Example 64

N-[4-(azetidin-3-ylmethyl)phenyl]-6-chloro-pyridine-3-carboxamide

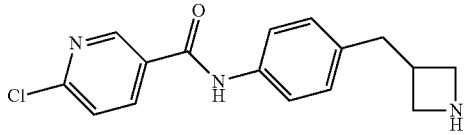 [SMILES: O=C(Nc1ccc(CC2CNC2)cc1)c1ccc(Cl)nc1]

a) tert-butyl 3-(4-aminobenzyl)azetidine-1-carboxylate

To a stirred solution of tert-butyl 3-[(4-aminophenyl)methylene]azetidine-1-carboxylate (350 mg, 1.34 mmol) in MeOH (8 mL) under nitrogen was added 10 wt. % Pd/C (71.5 mg, 67.2 µmol). The resulting black suspension was purged by evacuation and then back filled with a stream of hydrogen (balloon) for three times. The mixture was stirred for 16 hours at room temperature under hydrogen atmosphere. The resulting suspension was filtered directly through a plug of dicalite. The filter cake was rinsed with EtOAc and the filtrate was concentrated in vacuo to afford the title compound (344 mg, 97%) as a white solid. MS (ISP): 207.3 ([M-C$_4$H$_8$+H]$^+$).

b) tert-butyl 3-[[4-[(6-chloropyridine-3-carbonyl)amino]phenyl]methyl]azetidine-1-carboxylate To a stirred solution of tert-butyl 3-(4-aminobenzyl)azetidine-1-carboxylate (20.0 mg, 76.2 µmol) in DMF (500 µL) under nitrogen was added 6-chloronicotinic acid (11.2 mg 83.9 µmol, CAS 5326-23-8), N-methylmorpholine (25.1 µL, 229 µmol) and HBTU (43.3 mg, 114 µmol). The reaction mixture was stirred overnight at room temperature before being quenched by addition of saturated aqueous NH$_4$Cl. The reaction mixture was poured into water and extracted with EtOAc. The organic layers were washed with saturated NaHCO$_3$, brine, dried (Na$_2$SO$_4$) and concentrated in vacuo. The crude residue was purified by flash chromatography (silica gel, gradient: 0% to 50% EtOAc in heptane) to afford the title compound (23 mg, 75%) as a colorless oil. MS (ISP): 348.2 ([{$^{37}$Cl}M-C$_4$H$_8$+H]$^+$), 346.2 ([{$^{35}$Cl}M-C$_4$H$_8$+H]$^+$).

c) N-[4-(azetidin-3-ylmethyl)phenyl]-6-chloro-pyridine-3-carboxamide 2,2,2-trifluoroacetic acid To a stirred solution of tert-butyl 3-[[4-[(6-chloropyridine-3-carbonyl)amino]phenyl]methyl]azetidine-1-carboxylate (55 µmol) in CH$_2$Cl$_2$ (1.0 mL) was added 2,2,2-trifluoroacetic acid (0.5 mL). The reaction mixture was stirred for 2 hours at room temperature before all volatiles were removed under high vacuum. The residue was triturated with diethyl ether, filtered and dried under high vacuum to afford the title compound (18.1 mg, 79%) as a white powder. MS (ISP): 304.1 ([{$^{37}$Cl}M+H]$^+$), 302.1 ([{$^{35}$Cl}M+H]$^+$).

Example 65

N-[4-(azetidin-3-ylidenemethyl)phenyl]-6-chloropyridine-3-carboxamide

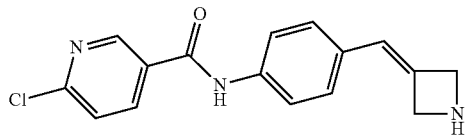 [SMILES: O=C(Nc1ccc(C=C2CNC2)cc1)c1ccc(Cl)nc1]

The title compound was obtained in analogy to example 58 using 6-chloronicotinic acid (CAS 5326-23-8) in place of 4-chloro-3-cyclopropyl-1H-pyrazole-5-carboxylic acid in step (c). White powder. MS (ISP): 302.2 ([{$^{37}$Cl}M+H]$^+$), 300.2 ([{$^{35}$Cl}M+H]$^+$).

Example 66

4-chloro-3-ethyl-N-[4-[(3-fluoroazetidin-3-yl)methyl]phenyl]-1H-pyrazole-5-carboxamide

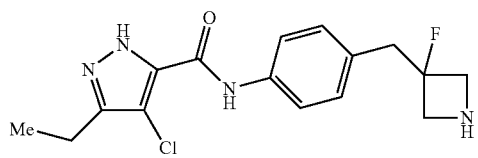 [SMILES: CCc1n[nH]c(C(=O)Nc2ccc(CC3(F)CNC3)cc2)c1Cl]

The title compound was obtained in analogy to example 52 using 4-chloro-3-ethyl-1H-pyrazole-5-carboxylic acid in place of 4-chlorobenzoic acid in step (d). White powder. MS (ISP): 339.2 ([{$^{37}$Cl}M+H]$^+$), 337.2 ([{$^{35}$Cl}M+H]$^+$).

Example 67

6-ethoxy-N-[4-[(3-fluoroazetidin-3-yl)methyl]phenyl]pyridazine-3-carboxamide

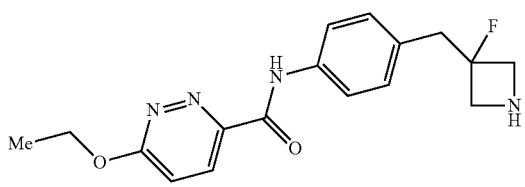 [SMILES: CCOc1ccc(C(=O)Nc2ccc(CC3(F)CNC3)cc2)nn1]

The title compound was obtained in analogy to example 52 using 6-ethoxypyridazine-3-carboxylic acid in place of 4-chlorobenzoic acid in step (d). White powder. MS (ISP): 331.2 ([M+H]$^+$).

Example 68

6 N-[4-[(3-fluoroazetidin-3-yl)methyl]phenyl]-6-methoxy-2-(trifluoromethyl)pyrimidine-4-carboxamide

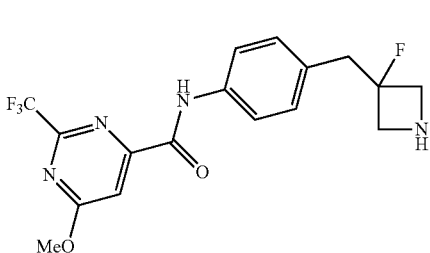 [SMILES: COc1cc(C(=O)Nc2ccc(CC3(F)CNC3)cc2)nc(C(F)(F)F)n1]

The title compound was obtained in analogy to example 52 using 6-methoxy-2-(trifluoromethyl)pyrimidine-4-carboxylic acid in place of 4-chlorobenzoic acid in step (d). White powder. MS (ISP): 385.2 ([M+H]+).

Example 69

N-[4-[(3-fluoroazetidin-3-yl)methyl]phenyl]-2-(2,2,2-trifluoroethoxy)pyrimidine-5-carboxamide

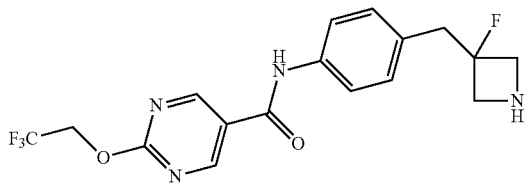 [SMILES: O=C(Nc1ccc(CC2(F)CNC2)cc1)c1cnc(OCC(F)(F)F)nc1]

The title compound was obtained in analogy to example 52 using 6-ethoxypyridazine-3-carboxylic acid in place of 4-chlorobenzoic acid in step (d). White powder. MS (ISP): 385.3 ([M+H]+).

Example 70

N-[4-[(3-fluoroazetidin-3-yl)methyl]phenyl]-5-(trifluoromethyl)pyrazine-2-carboxamide

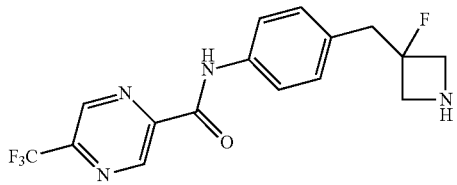 [SMILES: O=C(Nc1ccc(CC2(F)CNC2)cc1)c1cnc(C(F)(F)F)cn1]

The title compound was obtained in analogy to example 52 using 5-(trifluoromethyl)pyrazine-2-carboxylic acid in place of 4-chlorobenzoic acid in step (d). White powder. MS (ISP): 355.2 ([M+H]+).

Example 71

N-[4-[[(2S)-azetidin-2-yl]methyl]phenyl]-4-chlorobenzamide

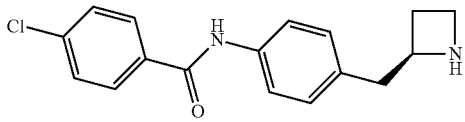 [SMILES: O=C(Nc1ccc(C[C@H]2CCN2)cc1)c1ccc(Cl)cc1]

a) (RS)-2-[(4-nitrophenyl)methyl]azetidine

To a stirred solution of racemic 2-benzylazetidine hydrochloride (141 mg, 0.768 mmol) in sulfuric acid (614 µL, 11.5 mmol) at 0° C. was added CH2Cl2 (1 mL). The reaction mixture was cooled to −20° C. then nitric acid (58.1 µL, 0.844 mmol, 65 wt. %) was added. The reaction was allowed to warm to 0° C. then stirred for further 30 min before being quenched by addition of NaOH (6.0M) to pH 10-11. The mixture was extracted with CH2Cl2 and the combined organic extracts were dried (Na2SO4) and concentrated in vacuo to afford the title compound (118 mg, 80%, orange oil) together with low amount of ortho and meta-isomers. MS (ISP): 193.1 ([M+H]+).

b) tert-butyl (RS)-2-[(4-nitrophenyl)methyl]azetidine-1-carboxylate

To a stirred solution of (RS)-2-[(4-nitrophenyl)methyl]azetidine (118 mg, 0.614 mmol) in methanol (3.5 mL) were added di-tert-butyl dicarbonate (268 mg, 1.23 mmol) and N,N-diisopropylethylamine (214 µL, 1.23 mmol) and the reaction was stirred at room temperature for 16 hour. The reaction was poured into water and extracted with EtOAc. The combined organic extracts were washed with brine, dried (MgSO4) and concentrated in vacuo. The crude residue was purified by flash chromatography (silica gel, gradient: 0% to 20% EtOAc in heptane) to afford the title compound (90 mg, 50%, orange oil) together with low amount of meta-isomer. MS (ISP): 237.2 ([M-C4H8+H]+).

c) tert-butyl (RS)-2-[(4-aminophenyl)methyl]azetidine-1-carboxylate

To a stirred solution of tert-butyl (RS)-2-[(4-nitrophenyl)methyl]azetidine-1-carboxylate (89 mg, 0.304 mmol) in EtOAc (1.5 mL) under nitrogen was added 10 wt. % Pd/C (16.2 mg, 15.2 µmol). The resulting black suspension was purged by evacuation and then back filled with a stream of hydrogen (balloon) for three times. The mixture was stirred for 16 hours at room temperature under hydrogen atmosphere. The resulting suspension was filtered directly through a plug of dicalite. The filter cake was rinsed with EtOAc and the filtrate was concentrated in vacuo to yield the title compound (80 mg, 99%, light yellow oil) together with low amount of meta-isomer. MS (ISP): 207.1 ([M-C4H8+H]+).

d) tert-butyl (S)-2-[(4-aminophenyl)methyl]azetidine-1-carboxylate & tert-butyl (R)-2-[(4-aminophenyl)methyl]azetidine-1-carboxylate The enantiomers of tert-butyl (RS)-2-[(4-aminophenyl)methyl]azetidine-1-carboxylate (80 mg) were separated using HPLC (column: Reprosil Chiral-NR, 250×20 mm I.D., 35 mL/min, eluent: EtOH/heptane: 15/85, 205 nm, 240 psi) affording:

(+)-tert-butyl (S)-2-[(4-aminophenyl)methyl]azetidine-1-carboxylate (28.4 mg, colorless oil), retention time=18.5 min (−)-tert-butyl (R)-2-[(4-aminophenyl)methyl]azetidine-1-carboxylate (24.2 mg, colorless oil), retention time=19.6 min e) tert-butyl (S)-2-[[4-[(4-chlorobenzoyl)amino]phenyl]methyl]azetidine-1-carboxylate To a stirred solution of tert-butyl (S)-2-[(4-aminophenyl)methyl]azetidine-1-carboxylate (11 mg, 42 µmol) in DMF (0.25 mL) at room temperature was added 4-chlorobenzoic acid (7.9 mg, 51 mol), N-methylmorpholine (13.8 µL, 126 µmol) and HBTU (23.8 mg, 63 µmol). The reaction mixture was stirred overnight at room temperature before being quenched by addition of saturated aqueous NH$_4$Cl. The reaction mixture was poured into water and extracted with EtOAc. The combined organic extracts were washed with saturated aqueous NaHCO$_3$, brine, dried (Na$_2$SO$_4$) and concentrated in vacuo. The residue was purified by flash chromatography (silica gel, gradient: 0% to 30% EtOAc in heptane) to afford the title compound (10.3 mg, 61%) as a white solid. MS (ISP): 401.3 ([{$^{37}$Cl}M−H]$^-$), 399.3 ([{$^{35}$Cl}M−H]$^-$).

f) N-[4-[[(2S)-azetidin-2-yl]methyl]phenyl]-4-chloro-benzamide 2,2,2-trifluoroacetic acid To a stirred solution of tert-butyl tert-butyl (S)-2-[[4-[(4-chlorobenzoyl)amino]phenyl]methyl]azetidine-1-carboxylate (25 µmol) in CH$_2$Cl$_2$ (0.5 mL) was added 2,2,2-trifluoroacetic acid (0.25 mL). The reaction mixture was stirred for 2 hours at room temperature before all volatiles were removed under high vacuum. The residue was triturated with diethyl ether, filtered and dried under high vacuum to afford the title compound (10 mg, 97%) as a white powder. MS (ISP): 303.1 ([{$^{37}$Cl}M+H]$^+$), 301.1 ([{$^{35}$Cl}M+H]$^+$).

Example 72

N-[4-[[(2R)-azetidin-2-yl]methyl]phenyl]-4-chloro-benzamide

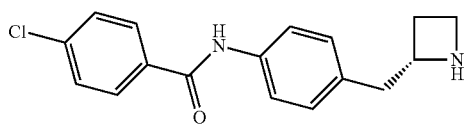 [SMILES: O=C(Nc1ccc(C[C@@H]2CCN2)cc1)c1ccc(Cl)cc1]

The title compound was obtained in analogy to example 71 using tert-butyl (R)-2-[(4-aminophenyl)methyl]azetidine-1-carboxylate in place of tert-butyl (S)-2-[(4-aminophenyl)methyl]azetidine-1-carboxylate in step (e). White powder. MS (ISP): 303.1 ([{$^{37}$Cl}M+H]$^+$), 301.1 ([{$^{35}$Cl}M+H]$^+$).

Example 73

6-chloro-N-[4-[(3-methoxyazetidin-3-yl)methyl]phenyl]pyridine-3-carboxamide

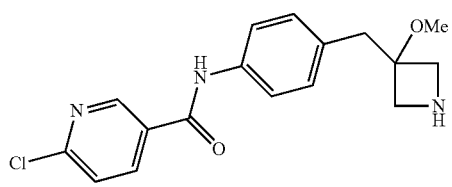 [SMILES: COC1(Cc2ccc(NC(=O)c3ccc(Cl)nc3)cc2)CNC1]

a) 1-benzhydryl-3-benzyl-3-methoxyazetidine

To a stirred solution of 1-benzhydryl-3-benzylazetidin-3-ol (400 mg, 1.21 mmol) in THF (5 mL) at room temperature was added NaH (58.3 mg, 1.21 mmol, 60% in mineral oil). After 30 min, iodomethane (106 µL, 1.7 mmol) was added and the reaction mixture was stirred overnight at room temperature. The reaction was quenched by careful addition of saturated aqueous NH$_4$Cl, diluted with water and extracted with EtOAc. The combined organic extracts were washed with brine, dried (Na$_2$SO$_4$) and concentrated in vacuo. The crude residue was purified by flash chromatography (silica gel, gradient: 0% to 10% EtOAc in heptane) to afford the title compound (313 mg, 75%) as a colorless oil. MS (ISP): 344.3 ([M+H]$^+$).

b) 3-benzyl-3-methoxyazetidine

To a stirred solution of 1-benzhydryl-3-benzyl-3-methoxyazetidine (300 mg, 873 µmol) in methanol (8 mL) under nitrogen was added aqueous HCl (2.0 M, 524 µL, 1.05 mmol) and 10 wt. % Pd/C (46.5 mg, 43.7 µmol). The resulting black suspension was purged by evacuation and then back filled with a stream of hydrogen (balloon) for three times. The mixture was stirred for 16 hours at room temperature under hydrogen atmosphere. The resulting suspension was filtered directly through a plug of dicalite. The filter cake was rinsed with methanol and the filtrate was concentrated in vacuo. The resulting residue was dissolved in 1.0 M aqueous HCl and the solution was extracted with diethyl ether. The organic phase was discarded while the water layers were neutralized to pH 11-12 by addition of 3.0 M aqueous NaOH. The mixture was extracted with CH$_2$Cl$_2$ and the layers separated. The organic phase was washed with brine, dried (Na$_2$SO$_4$) and concentrated in vacuo to afford the title compound (153 mg, 99%) as a colorless oil. MS (ISP): 178.1 ([M+H]$^+$).

c) 3-methoxy-3-(4-nitrobenzyl)azetidine

To a stirred solution of 3-benzyl-3-methoxyazetidine (140 mg, 790 µmol) in sulfuric acid (632 µL, 11.8 mmol) at 0° C. was added CH$_2$Cl$_2$ (1 mL). The reaction mixture was cooled to −20° C. then nitric acid (59.7 µL, 869 µmol, 65 wt. %) was added. The reaction was allowed to warm to 0° C. then stirred for further 30 min before being quenched by addition of aqueous NaOH (6.0M) to pH 10-11. The mixture was extracted with CH$_2$Cl$_2$ and the combined organic extracts were dried (Na$_2$SO$_4$) and concentrated in vacuo to afford the title compound (116 mg, 66%) as a yellow solid which was used in the next step without further purification.

d) tert-butyl 3-methoxy-3-(4-nitrobenzyl)azetidine-1-carboxylate

To a stirred solution of 3-methoxy-3-(4-nitrobenzyl)azetidine (116 mg, 448 µmol) in methanol (3 mL) was added N,N-diisopropylethylamine (157 µL, 897 µmol). After 15 min, di-tert-butyl dicarbonate (196 mg, 897 µmol) was added and the reaction was stirred overnight. The reaction was poured into water and extracted with EtOAc. The combined organic extracts were washed with brine, dried (Na₂SO₄) and concentrated in vacuo. The crude residue was purified by flash chromatography (silica gel, gradient: 0% to 20% EtOAc in heptane) to yield the title compound as an orange oil (70.8 mg, 49%). MS (ISP): 267.2 ([M-C$_4$H$_8$+H]$^+$).

e) tert-butyl 3-(4-aminobenzyl)-3-methoxyazetidine-1-carboxylate

To a stirred solution of tert-butyl 3-methoxy-3-(4-nitrobenzyl)azetidine-1-carboxylate (70.8 mg, 220 µmol) in ethyl acetate (2 mL) under nitrogen atmosphere was added 10 wt. % Pd/C (11.7 mg, 11.0 µmol). The resulting black suspension was purged by evacuation and then back filled with a stream of hydrogen (balloon) for three times. The mixture was stirred for 16 hours at room temperature under hydrogen atmosphere. The resulting suspension was filtered directly through a plug of dicalite. The filter cake was rinsed with EtOAc and the filtrate was concentrated in vacuo. The crude residue was purified by flash chromatography (silica gel, gradient: 0% to 30% EtOAc in heptane) to yield the title compound (57 mg, 89%) as a colorless oil. MS (ISP): 237.2 ([M-C$_4$H$_8$+H]$^+$).

f) tert-butyl 3-[[4-[(6-chloropyridine-3-carbonyl)amino]phenyl]methyl]-3-methoxy-azetidine-1-carboxylate To a stirred solution of tert-butyl 3-(4-aminobenzyl)-3-methoxyazetidine-1-carboxylate (25 mg, 85 µmol) in DMF (500 ul) at room temperature was added 6-chloronicotinic acid (16.2 mg, 103 mol), N-methylmorpholine (28.2 µL, 257 µmol) and HBTU (48.6 mg, 128 µmol). The reaction mixture was stirred overnight at room temperature before being quenched by addition of saturated aqueous NH₄Cl. The reaction mixture was poured into water and extracted with EtOAc. The combined organic extracts were washed with saturated aqueous NaHCO₃, brine, dried (Na₂SO₄) and concentrated in vacuo. The residue was purified by flash chromatography (silica gel, gradient: 0% to 40% EtOAc in heptane) to afford the title compound (16 mg, 43%) as a colorless oil. MS (ISP): 432.5 ([{$^{37}$Cl}M−H]$^−$), 430.4 ([{$^{35}$Cl}M−H]$^−$).

g) 6-chloro-N-[4-[(3-methoxyazetidin-3-yl)methyl]phenyl]pyridine-3-carboxamide 2,2,2-trifluoroacetic acid To a stirred solution of tert-butyl 3-[[4-[(6-chloropyridine-3-carbonyl)amino]phenyl]methyl]-3-methoxy-azetidine-1-carboxylate (37 µmol) in CH₂Cl₂ (1.0 mL) was added 2,2,2-trifluoroacetic acid (0.5 mL). The reaction mixture was stirred for 2 hours at room temperature before all volatiles were removed under high vacuum to afford the title compound (12 mg, 73%) as a colorless oil. MS (ISP): 334.3 ([{$^{37}$Cl}M+H]$^+$), 332.3 ([{$^{35}$Cl}M+H]$^+$).

Example 74

N-[4-[(3-methoxyazetidin-3-yl)methyl]phenyl]-2-(trifluoromethyl)pyrimidine-5-carboxamide

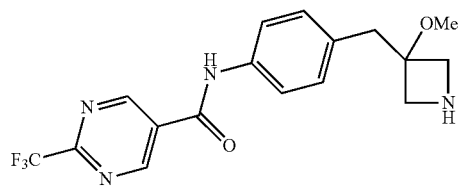 [SMILES: COC1(Cc2ccc(NC(=O)c3cnc(C(F)(F)F)nc3)cc2)CNC1]

The title compound was obtained in analogy to example 73 using 2-(trifluoromethyl)pyrimidine-5-carboxylic acid in place of 6-chloronicotinic acid in step (f). Light brown oil. MS (ISP): 367.3 ([M+H]$^+$).

Example 75

N-[4-(azetidin-3-yloxy)phenyl]-5-(trifluoromethyl)pyrazine-2-carboxamide

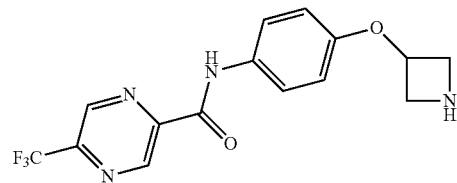 [SMILES: O=C(Nc1ccc(OC2CNC2)cc1)c1cnc(C(F)(F)F)cn1]

The title compound was obtained in analogy to example 10 using 5-(trifluoromethyl)pyrazine-2-carboxylic acid (CAS 1060814-50-7) in place of 3-cyclopropyl-1H-pyrazole-5-carboxylic acid in step (a). White powder. MS (ISP): 339.3 ([M+H]$^+$).

Example 76

N-[4-(azetidin-3-yloxy)phenyl]-6-ethoxy-pyridazine-3-carboxamide

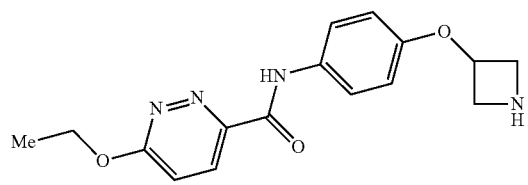 [SMILES: CCOc1ccc(C(=O)Nc2ccc(OC3CNC3)cc2)nn1]

The title compound was obtained in analogy to example 10 using 6-ethoxypyridazine-3-carboxylic acid (CAS 142054-74-8) in place of 3-cyclopropyl-1H-pyrazole-5-carboxylic acid in step (a). White powder. MS (ISP): 315.1 ([M+H]$^+$).

Example 77

N-[4-(azetidin-3-yloxy)phenyl]-5-(2,2,2-trifluoroethoxy)pyrazine-2-carboxamide

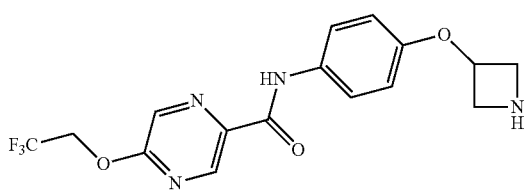 [SMILES: O=C(Nc1ccc(OC2CNC2)cc1)c1cnc(OCC(F)(F)F)cn1]

The title compound was obtained in analogy to example 10 using 5-(2,2,2-trifluoroethoxy)pyrazine-2-carboxylic acid in place of 3-cyclopropyl-1H-pyrazole-5-carboxylic acid in step (a). White powder. MS (ISP): 369.1 ([M+H]$^+$).

Example 78

N-[4-[[(2R)-azetidin-2-yl]methyl]phenyl]-2-(trifluoromethyl)pyrimidine-5-carboxamide

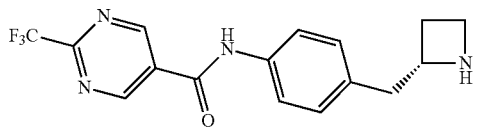 [SMILES: O=C(Nc1ccc(C[C@@H]2CCN2)cc1)c1cnc(C(F)(F)F)nc1]

The title compound was obtained in analogy to example 71 using tert-butyl (R)-2-[(4-aminophenyl)methyl]azetidine-1-carboxylate in place of tert-butyl (S)-2-[(4-aminophenyl)methyl]azetidine-1-carboxylate and 2-(trifluoromethyl)pyrimidine-5-carboxylic acid in place of 4-chlorobenzoic acid in step (e). Light yellow amorphous. MS (ISP): 337.3 ([M+H]$^+$).

Example 79

N-[4-[[(2R)-azetidin-2-yl]methyl]phenyl]-6-chloropyridine-3-carboxamide

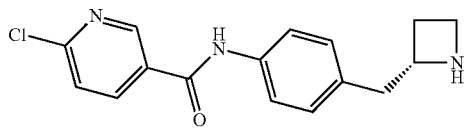 [SMILES: O=C(Nc1ccc(C[C@@H]2CCN2)cc1)c1ccc(Cl)nc1]

The title compound was obtained in analogy to example 71 using tert-butyl (R)-2-[(4-aminophenyl)methyl]azetidine-1-carboxylate in place of tert-butyl (S)-2-[(4-aminophenyl)methyl]azetidine-1-carboxylate and 6-chloropyridine-3-carboxylic acid in place of 4-chlorobenzoic acid in step (e). White amorphous. MS (ISP): 304.2 ([{$^{37}$Cl}M+H]$^+$), 302.2 ([{$^{35}$Cl}M+H]$^+$).

Example 80

N-[4-[[(2S)-azetidin-2-yl]methyl]phenyl]-2-(trifluoromethyl)pyrimidine-5-carboxamide

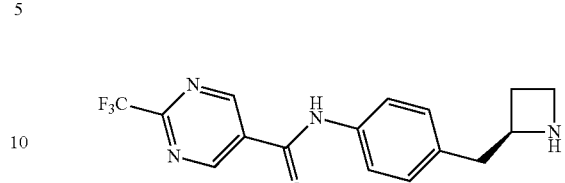

The title compound was obtained in analogy to example 71 using 2-(trifluoromethyl)pyrimidine-5-carboxylic acid in place of 4-chlorobenzoic acid in step (e). Light yellow amorphous. MS (ISP): 337.3 ([M+H]$^+$).

Example 81

N-[4-[[(2S)-azetidin-2-yl]methyl]phenyl]-6-chloropyridine-3-carboxamide

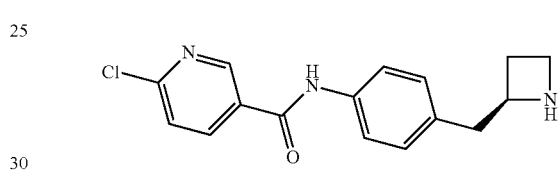

The title compound was obtained in analogy to example 71 using 6-chloropyridine-3-carboxylic acid in place of 4-chlorobenzoic acid in step (e). White amorphous. MS (ISP): 304.2 ([{$^{37}$Cl}M+H]$^+$), 302.2 ([{$^{35}$Cl}M+H]).

Example 82

N-(4-(azetidin-3-ylidenemethyl)-3,5-difluorophenyl)-6-methyl-2-(trifluoromethyl)pyrimidine-4-carboxamide

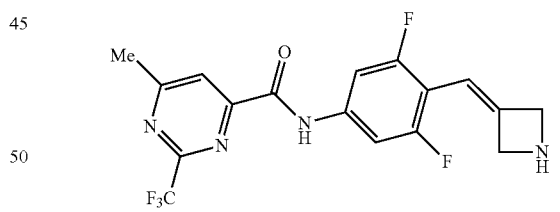

a) (4-bromo-2,6-difluoro-phenyl)methanol

To a stirred solution of 4-bromo-2,6-difluorobenzaldehyde (4.4 g, 19.9 mmol) in a 4:1 mixture of CH$_2$Cl$_2$ and MeOH (100 mL) at 0° C. was added in one portion NaBH$_4$ (829 mg, 21.9 mmol). The reaction mixture was stirred for 1 hour at 0° C. before being quenched by the careful addition of aqueous HCl (1.0 M). After 30 min, the reaction was poured into water and extracted with EtOAc. The combined organic extracts were washed with brine, dried (Na$_2$SO$_4$) and concentrated in vacuo to afford the title compound (4.24 g, 95%) as a white solid. MS (ISP): 223.2 ([{$^{81}$Br}M–H]$^-$), 221.2 ([{$^{79}$Br}M–H]$^-$).

b) 5-bromo-2-(bromomethyl)-1,3-difluoro-benzene

To a stirred solution of (4-bromo-2,6-difluoro-phenyl)methanol (4.2 g, 18.8 mmol) in CH$_2$Cl$_2$ (80 mL) at 0° C. was added CBr$_4$ (7.81 g, 23.5 mmol). After 5 min, a solution of triphenylphosphine (6.17 g, 23.5 mmol) in CH$_2$Cl$_2$ (20 mL) was added dropwise and the resulting mixture was stirred at room temperature for 2 hours. The mixture was concentrated in vacuo and the residue was taken up in heptane (100 mL). The resulting precipitate (white solid) was collected through a sintered glass and washed with further heptane. The filtrate was concentrated in vacuo to afford the title compound (6.90 g, 78%) as a colorless oil which was used in the following step without further purification.

c) 5-bromo-2-(diethoxyphosphorylmethyl)-1,3-difluoro-benzene

A round-bottomed flask was charged with 5-bromo-2-(bromomethyl)-1,3-difluoro-benzene (6.9 g, 18.8 mmol) and triethyl phosphite (4.69 g, 28.2 mmol, CAS 122-52-1). The resulting colorless solution was heated at 130° C. for 4 hours then the excess of triethyl phosphite was removed by distillation. The residue was purified by flash chromatography (silica gel, gradient: 0% to 30% CH$_2$Cl$_2$/MeOH in heptane) to afford the title compound (4.89 g, 75%) as colorless oil. MS (ISP): 345.3 ([{$^{81}$Br}M+H]$^+$), 343.3 ([{$^{79}$Br}M+H]$^+$).

d) tert-butyl 3-[(4-bromo-2,6-difluoro-phenyl)methylene]azetidine-1-carboxylate To a stirred solution of diisopropylamine (1.08 mL, 7.58 mmol) in THF (8 mL) at −78° C. was added dropwise BuLi (1.6 M in hexane, 4.74 mL, 7.58 mmol). After 5 min, the reaction was allowed to warm to 0° C. and stirred for 30 min before being cooled to −78° C. A solution of 5-bromo-2-(diethoxyphosphorylmethyl)-1,3-difluoro-benzene (2.0 g, 5.83 mmol) in THF (5 mL) was added dropwise and the reaction was stirred at −60° C. for further 15 min. The reaction mixture was re-cooled to −78° C. and a solution of tert-butyl 3-oxoazetidine-1-carboxylate (1.1 g, 6.41 mmol, CAS 398489-26-4) in THF (5 mL) was added dropwise over 10 min. The reaction was allowed to warm to room temperature and stirred for 30 min before being poured into aqueous HCl (0.5 M) and extracted with EtOAc. The combined organic extracts were washed with brine, dried (Na$_2$SO$_4$) and concentrated in vacuo. The residue was purified by flash chromatography (silica gel, gradient: 0% to 20% EtOAc in heptane) to afford the title compound (1.58 g, 75%) as a white solid. MS (ISP): 306.1 ([{$^{81}$Br}M-C$_4$H$_8$+H]$^+$), 304.0 ([{$^{79}$Br}M-C$_4$H$_8$+H]$^+$).

e) tert-butyl 3-[[4-(benzhydrylideneamino)-2,6-difluoro-phenyl]methylene]azetidine-1-carboxylate A microwave vial was charged with tert-butyl 3-[(4-bromo-2,6-difluoro-phenyl)methylene]azetidine-1-carboxylate (1.58 g, 4.39 mmol), benzophenone imine (0.810 mL, 4.83 mmol), sodium tert-butoxide (674 mg, 7.02 mmol), rac-2,2'-bis(diphenylphosphino)-1,1'-binaphthyl (273 mg, 439 µmol), Pd$_2$(dba)$_3$ (121 mg, 132 µmol) and dry toluene (10 mL). The reaction mixture was degassed for 5 min by bubbling nitrogen through the reaction medium. The reaction was heated to 90° C. overnight and then filtered directly through a pad of dicalite. The filter cake was rinsed with EtOAc and the filtrate concentrated in vacuo. The crude residue was purified by flash chromatography (silica gel, gradient: 0% to 25% EtOAc in hexanes) to afford the title compound (1.87 g, 93%) as a yellow oil. MS (ISP): 461.3 ([M+H]$^+$).

f) tert-butyl 3-[(4-amino-2,6-difluoro-phenyl)methylene]azetidine-1-carboxylate To a stirred solution of tert-butyl 3-[[4-(benzhydrylideneamino)-2,6-difluoro-phenyl]methylene]azetidine-1-carboxylate (1.87 g, 4.06 mmol) in methanol (15 mL) was added under nitrogen sodium acetate (0.999 g, 12.2 mmol) and hydroxylamine hydrochloride (621 mg, 8.93 mmol).

The reaction mixture was stirred at 50° C. overnight. The resulting white precipitate was filtered off, while the filtrate was concentrated in vacuo and purified by flash chromatography (silica gel, gradient: 0% to 50% EtOAc in hexanes) to afford the tittle compound (946 mg, 78%) as a yellow solid. MS (ISP): 241.2 ([M-C$_4$H$_8$+H]$^+$).

g) tert-butyl3-[[2,6-difluoro-4-[[6-methyl-2-(trifluoromethyl)pyrimidine-4-carbonyl]amino]phenyl]methylene]azetidine-1-carboxylate To a stirred solution of tert-butyl 3-[(4-amino-2,6-difluoro-phenyl)methylene]azetidine-1-carboxylate (150 mg, 506 µmol) in THF (4 mL) at room temperature was added 6-methyl-2-(trifluoromethyl)pyrimidine-4-carboxylic acid (125 mg, 607 µmol), HBTU (48.6 mg, 128 µmol) and N-methylmorpholine (223 µL, 2.02 mmol). The reaction mixture was stirred overnight at 50° C. before being quenched by addition of saturated aqueous NH$_4$Cl. The reaction mixture was poured into water and extracted with EtOAc. The combined organic extracts were washed with saturated aqueous NaHCO$_3$, brine, dried (Na$_2$SO$_4$) and concentrated in vacuo. The residue was purified by flash chromatography (silica gel, gradient: 0% to 50% EtOAc in heptane) to afford the title compound (191 mg, 78%) as a yellow solid. MS (ISP): 483.3 ([M−H]$^−$).

h) N-(4-(azetidin-3-ylidenemethyl)-3,5-difluorophenyl)-6-methyl-2-(trifluoromethyl)pyrimidine-4-carboxamide To a stirred solution of tert-butyl3-[[2,6-difluoro-4-[[6-methyl-2-(trifluoromethyl)pyrimidine-4-carbonyl]amino]phenyl]methylene]azetidine-1-carboxylate (190 mg, 392 µmol) in acetonitrile (4.0 mL) and water (8 mL) was added 2,2,2-trifluoroacetic acid (0.30 mL, 3.92 mmol). The reaction mixture was stirred for 4 hours at 80° C., before being poured into a 2:1 mixture of EtOAc and THF and extracted with 1.0 M aqueous NaOH. The organic layer was washed with brine, dried (Na$_2$SO$_4$) and concentrated in vacuo. The residue was purified by flash chromatography (NH2-silica gel, CH$_2$Cl$_2$+NH$_3$aq./MeOH) to afford the title compound (105 mg, 69%) as a white solid. MS (ISP): 385.2 ([M+H]$^+$).

Example 83

N-(4-(azetidin-3-ylidenemethyl)-3,5-difluorophenyl)-3-ethyl-4-methyl-1H-pyrazole-5-carboxamide

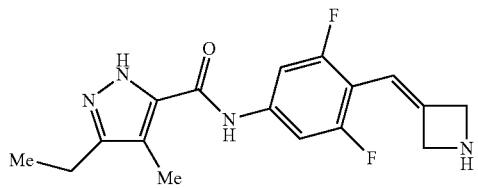 [SMILES: CCc1n[nH]c(C(=O)Nc2cc(F)c(C=C3CNC3)c(F)c2)c1C]

The title compound was obtained in analogy to example 82 using 3-ethyl-4-methyl-1H-pyrazole-5-carboxylic acid in place of 6-methyl-2-(trifluoromethyl)pyrimidine-4-carboxylic acid in step (g). White powder. MS (ISP): 333.2 ([M+H]$^+$).

Example 84

N-(4-(azetidin-3-ylidenemethyl)-3,5-difluorophenyl)-6-chloronicotinamide

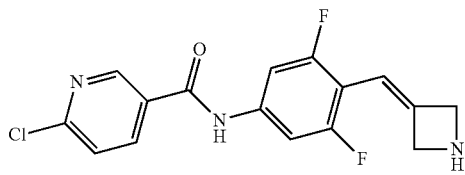 [SMILES: O=C(Nc1cc(F)c(C=C2CNC2)c(F)c1)c1ccc(Cl)nc1]

The title compound was obtained in analogy to example 82 using 6-chloronicotinic acid in place of 6-methyl-2-(trifluoromethyl)pyrimidine-4-carboxylic acid in step (g). Off-white solid. MS (ISP): 338.2 ([{$^{37}$Cl}M+H]$^+$), 336.2 ([{$^{35}$Cl}M+H]$^+$).

Example 85

N-(4-(azetidin-3-ylidenemethyl)-3-fluorophenyl)-6-methyl-2-(trifluoromethyl)pyrimidine-4-carboxamide

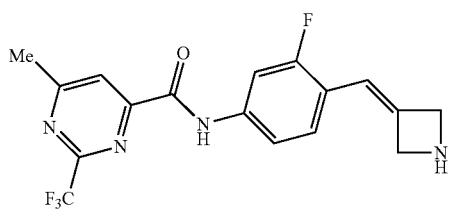 [SMILES: Cc1cc(C(=O)Nc2ccc(C=C3CNC3)c(F)c2)nc(C(F)(F)F)n1]

The title compound was obtained in analogy to example 82 using 4-bromo-1-(bromomethyl)-2-fluorobenzene (CAS 76283-09-5) in place of 5-bromo-2-(bromomethyl)-1,3-difluoro-benzene in step (c). Light yellow solid. MS (ISP): 367.2 ([M+H]$^+$).

Example 86

N-(4-(azetidin-3-ylidenemethyl)-3-fluorophenyl)-6-chloronicotinamide

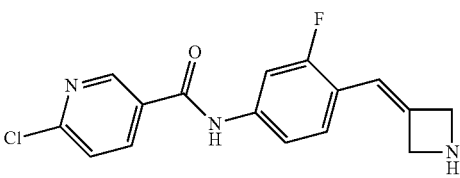 [SMILES: O=C(Nc1ccc(C=C2CNC2)c(F)c1)c1ccc(Cl)nc1]

The title compound was obtained in analogy to example 82 using 4-bromo-1-(bromomethyl)-2-fluorobenzene in place of 5-bromo-2-(bromomethyl)-1,3-difluoro-benzene in step (c) and 6-chloronicotinic acid in place of 6-methyl-2-(trifluoromethyl)pyrimidine-4-carboxylic acid in step (g). Off-white solid. MS (ISP): 320.2 ([{$^{37}$Cl}M+H]$^+$), 318.2 ([{$^{35}$Cl}M+H]$^+$).

Example 87

N-(4-(azetidin-3-ylidenemethyl)-3,5-difluorophenyl)-6-ethyl-2-(trifluoromethyl)pyrimidine-4-carboxamide

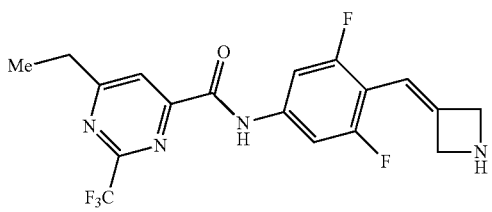 [SMILES: CCc1cc(C(=O)Nc2cc(F)c(C=C3CNC3)c(F)c2)nc(C(F)(F)F)n1]

The title compound was obtained in analogy to example 82 using 6-ethyl-2-(trifluoromethyl)pyrimidine-4-carboxylic acid in place of 6-methyl-2-(trifluoromethyl)pyrimidine-4-carboxylic acid in step (g). Yellow solid. MS (ISP): 399.3 ([M+H]$^+$).

Example 88

N-(4-(azetidin-3-ylidenemethyl)-3-fluorophenyl)-3-ethyl-4-methyl-1H-pyrazole-5-carboxamide

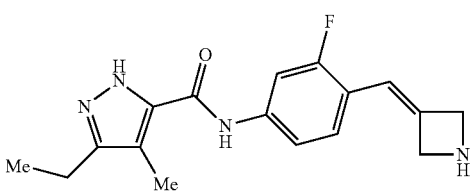 [SMILES: CCc1n[nH]c(C(=O)Nc2ccc(C=C3CNC3)c(F)c2)c1C]

The title compound was obtained in analogy to example 82 using 4-bromo-1-(bromomethyl)-2-fluorobenzene in place of 5-bromo-2-(bromomethyl)-1,3-difluoro-benzene in step (c) and 3-ethyl-4-methyl-1H-pyrazole-5-carboxylic acid in place of 6-methyl-2-(trifluoromethyl)pyrimidine-4-carboxylic acid in step (g). Orange solid. MS (ISP): 315.2 ([M+H]$^+$).

Example 89

(S)-2-benzylazetidine

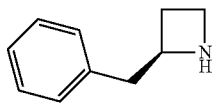 [SMILES: c1ccc(C[C@H]2CCN2)cc1]

a) tert-butyl N-[(1S)-1-benzyl-3-hydroxy-propyl]carbamate

To a stirred solution of (S)-3-(tert-butoxycarbonylamino)-4-phenyl-butanoic acid (2.16 g, 7.73 mmol, CAS 51871-62-6) in anhydrous THF (15 mL) at 0° C. was added N-methyl morpholine (1.02 mL, 9.28 mmol) followed by methyl chloroformate (0.719 mL, 9.28 mmol). After 1 hour, the resulting white suspension was filtered through a sintered funnel and the collected solid (N-methyl morpholinium chloride) washed with further anhydrous THF (10 mL). The filtrate was then re-cooled to 0° C. and treated with a solution of NaBH$_4$ (380 mg, 10.1 mmol) in water (4 mL). After 15 min, the reaction was allowed to warm up to room temperature and stirred for further 30 min before being quenched by the addition of aqueous saturated NaHCO3. The mixture was diluted with water and extracted with EtOAc. The combined organic extracts were washed with brine, dried (Na$_2$SO$_4$) and concentrated in vacuo to afford the title compound as (2.04 g, 99%) as a light yellow oil which was used in the following step without further purification.

b) (S)-3-amino-4-phenyl-butan-1-ol hydrochloride

To a stirred solution of tert-butyl N-[(1S)-1-benzyl-3-hydroxy-propyl]carbamate (677 mg, 2.55 mmol) in 1,4-dioxane (6.0 mL) was added a 4.0 M solution of HCl in 1,4-dioxane (6.38 mL, 25.5 mmol). The reaction mixture was stirred at 60° C. for 2 hours before being cooled to room temperature and stirred for further 12 hours. The resulting suspension was filtered through a sintered funnel. The collected hydrochloride salt was washed with further anhydrous diethyl ether then dried under high vacuum to afford the title compound (482 mg, 94%) as a white solid. MS (ISP): 166.1 ([M+H]$^+$).

c) (S)-3-[(4-methoxyphenyl)methylamino]-4-phenyl-butan-1-ol

To a stirred solution of (S)-3-amino-4-phenyl-butan-1-ol hydrochloride (480 mg, 2.38 mmol) in MeOH (4.0 mL) at room temperature was added N,N-diisopropylethylamine (0.5 mL, 2.86 mmol) and 4-methoxy benzaldehyde (324 al, 2.62 mmol, CAS 123-11-5). After 16 hours, NaBH$_4$ (135 mg, 3.57 mmol) was added in two portions and the mixture was stirred for further 2 hours at room temperature. The reaction mixture was poured into water and the pH was adjusted to 10-11 by addition of 2.0 M aqueous NaOH. The mixture was extracted with EtOAc and the combined organic extracts were dried (Na$_2$SO$_4$) and concentrated in vacuo to afford the title compound (844 mg, 124%) together with low amount of 4-methoxy benzyl alcohol.

d) (S)-4-chloro-N-[(4-methoxyphenyl)methyl]-1-phenyl-butan-2-amine

To a stirred solution of (S)-3-[(4-methoxyphenyl)methylamino]-4-phenyl-butan-1-ol (844 mg, 2.38 mmol) in CH$_2$Cl$_2$ (3.0 mL) at 0° C. was added dropwise a solution of thionyl chloride (237 μL, 3.25 mmol) in CH$_2$Cl$_2$ (0.5 mL). The reaction mixture was heated at reflux for 2 hours before being quenched by the addition of aqueous saturated NaHCO$_3$. The mixture was diluted with water and extracted with CH$_2$Cl$_2$. The combined organic extracts were washed with brine, dried (Na$_2$SO$_4$) and concentrated in vacuo. The residue was purified by flash chromatography (silica gel, 100% CH$_2$Cl$_2$) to afford the title compound (431 mg, 60%) as a colorless oil. MS (ISP): 306.1 ([{$^{37}$Cl}M+H]$^+$), 304.1 ([{$^{35}$Cl}M+H]$^+$).

e) (S)-2-benzyl-1-[(4-methoxyphenyl)methyl]azetidine

To a stirred solution of (S)-4-chloro-N-[(4-methoxyphenyl)methyl]-1-phenyl-butan-2-amine (1.22 g, 4.02 mmol) in anhydrous THF (20 mL) at 0° C. was added dropwise LiHMDS (1.0 M in THF, 8.03 mL, 8.03 mmol, CAS 4039-32-1). The reaction mixture was heated at reflux for 1 hour before being re-cooled to 0° C. then an additional equivalent of LiHMDS was added (4.02 mL, 4.02 mmol). The reaction mixture was heated at reflux for further 5 hours then allowed to warm to room temperature and quenched by the addition of saturated aqueous NH$_4$Cl. The mixture was diluted with water then extracted with EtOAc. The combined organic extracts were washed with brine, dried (Na$_2$SO$_4$) and concentrated in vacuo. The residue was purified by flash chromatography (silica gel, gradient: 0% to 50% EtOAc with 10% MeOH in heptane) to afford the title compound (965 mg, 90%) as a light brown oil. MS (ISP): 268.2 ([M+H]$^+$).

f) tert-butyl (S)-2-benzylazetidine-1-carboxylate

To a stirred solution of (S)-2-benzyl-1-[(4-methoxyphenyl)methyl]azetidine (865 mg, 3.24 mmol) in a 4:1 mixture of acetonitrile and water (20 mL) was added (NH$_4$)$_2$Ce(NO$_3$)$_6$ (5.43 g, 9.71 mmol) in one portion. The reaction mixture was stirred for 5 days at room temperature then diluted with water (40 mL) and extracted twice with diethyl ether. The organic layers were discarded while the water phase was evaporated to a dryness by azeotropic (toluene) removal of water. The resulting orange solid residue (5.53 g) was dissolved in MeOH and treated with N,N-diisopropylethylamine (5.05 mL, 28.9 mmol) followed by di-tert-butyl dicarbonate (2.0 g, 9.16 mmol). The reaction mixture was stirred at room temperature for 6 hours, before being partitioned between saturated aqueous NaHCO$_3$ and EtOAc. The organic phase was washed with brine, dried (Na$_2$SO$_4$) and concentrated in vacuo. The residue was purified by flash chromatography (silica gel, gradient: 0% to 10% EtOAc in heptane) to afford the title compound (445 mg, 55%) as a colorless oil. MS (ISP): 192.1 ([M-C$_4$H$_8$+H]$^+$).

g) (S)-2-benzylazetidine hydrochloride

To a stirred solution of tert-butyl (S)-2-benzylazetidine-1-carboxylate (290 mg, 1.17 mmol) in CH$_2$Cl$_2$ (5.0 mL) was added 2,2,2-trifluoroacetic acid (2.5 mL). The reaction mixture was stirred for 2 hours at room temperature before all volatiles were removed under high vacuum. The resulting viscous oil was re-dissolved in EtOH (2.0 mL) and treated with a 4.0 M solution of HCl in 1,4-dioxane (0.585 mL, 2.34 mmol). The resulting solution was evaporated to a dryness. The residue was triturated with diethyl ether, filtered and dried under high vacuum to afford the title compound (180 mg, 84%) as a white solid. MS (ISP): 148.0 ([M+H]$^+$).

Example 90

(2S,3S)-2-benzyl-3-fluoroazetidine

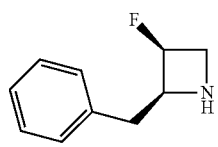 [SMILES: F[C@H]1CN[C@H]1Cc1ccccc1]

a) (S)-benzyl 4-diazo-3-oxo-1-phenylbutan-2-1 carbamate

To a stirred solution of (S)-2-(benzyloxycarbonylamino)-3-phenylpropanoic acid (10 g, 33.4 mmol, CAS 1161-13-3) in CH$_2$Cl$_2$ (100 mL) was added dropwise 1-chloro-N,N,2-trimethylpropenylamine (5.08 mL, 38.4 mmol) at room temperature. After 15 min, the reaction mixture was cooled to −10° C. and a solution of (trimethylsilyl)diazomethane in hexane (2.0 M, 20.0 mL, 40.1 mmol) was slowly added (caution: exothermic!). The reaction mixture was allowed to warm to room temperature till a red solution was obtained then the excess of diazomethane was destroyed by addition of AcOH (371 µL, 6.68 mmol) (caution: N$_2$ evolution!). The solvent was reduced to 10 mL by rotatory evaporation and the resulting residue was purified by flash chromatography (silica gel, gradient: 5% to 50% EtOAc in heptane to afford the title compound (7.93 g, 73%) as a yellow liquid. MS (ISP): 296.1 ([M-N$_2$+H]$^+$).

b) (S)-benzyl 2-benzyl-3-oxoazetidine-1-carboxylate

To a stirred solution of (S)-benzyl 4-diazo-3-oxo-1-phenylbutan-2-ylcarbamate (8.24 g, 25.5 mmol) in CH$_2$Cl$_2$ (600 mL) was added Et$_3$N (0.75 mL, 5.43 mmol) followed by 4 Å molecular sieves (~1.0 g). The reaction mixture was cooled to −40° C. and Rh$_2$(OAc)$_4$ (225 mg, 510 µmol) was added in one portion. The resulting green solution was stirred at −40° C. for 1 hour before allowed to warm to room temperature for 2 hours. Triphenylphosphine (478 mg, 1.82 mmol) was added and the reaction mixture was stirred at room temperature for further 15 min till a red solution was obtained. The solvent was evaporated by rotatory evaporation and the resulting residue was purified by flash chromatography (silica gel, gradient: 5% to 40% EtOAc in heptane) to afford the title compound (3.57 g, 47%) as a yellow solid. MS (ISP): 296.1 ([M+H]$^+$).

c) (2S)-benzyl 2-benzyl-3-hydroxyazetidine-1-carboxylate

To a stirred solution of (2S)-benzyl 2-benzyl-3-oxoazetidine-1-carboxylate (1.60 g, 5.4 mmol) in THF (18 mL) at 0° C. was added sodium borohydride (409 mg, 10.8 mmol) and the reaction mixture was stirred at room temperature for 1 hour. The reaction mixture was partitioned between saturated aqueous NH$_4$Cl and EtOAc. The organic layers were separated, washed with brine, dried (MgSO$_4$) and concentrated in vacuo. The residue was purified by flash chromatography (silica gel, gradient 5% to 50% EtOAc in heptane to afford the title compound (1.35 g, 84%, light yellow oil) as a 4:1 epimeric mixture at C3. MS (ISP): 298.1 ([M+H]$^+$).

d) (2S)-benzyl 2-benzyl-3-fluoroazetidine-1-carboxylate

To a stirred solution of triethylamine (58.3 µL, 420 µmol) and Et$_3$N.(HF)$_3$ (138 µL, 841 µmol) in CH$_2$Cl$_2$ (1.25 mL) were added XtalFluor-E® (144 mg, 631 µmol, CAS 63517-29-3) followed by (2S)-benzyl 2-benzyl-3-hydroxyazetidine-1-carboxylate (0.125 g, 420 µmol). The reaction mixture was stirred at room temperature for 1 hour before being quenched by addition of water and saturated aqueous NaHCO$_3$. The mixture was extracted with CH$_2$Cl$_2$ and the combined organic extracts were washed with brine, dried (MgSO$_4$) and concentrated in vacuo. The residue was purified by flash chromatography (silica gel, gradient: 5% to 40% EtOAc in heptane) to afford the title compound (102 mg, 81%, off-white solid) as a 4:1 epimeric mixture at C3. MS (ISP): 300.2 ([M+H]$^+$).

e) (2S,3S)-benzyl 2-benzyl-3-fluoroazetidine-1-carboxylate

The epimers at C3 of (2S)-benzyl 2-benzyl-3-fluoroazetidine-1-carboxylate were separated using chiral HPLC (column: Lux Amylose, 25 mL/min, i-PrOH/heptane: 30/70; 930 bar; 205 nm) affording:
(+)-benzyl (2S,3S)-2-benzyl-3-fluoro-azetidine-1-carboxylate (119 mg, white solid), retention time=14 min.
(+)-benzyl (2S,3R)-2-benzyl-3-fluoro-azetidine-1-carboxylate (30 mg, colorless oil), retention time=24 min.

f) (2S,3S)-2-benzyl-3-fluoro-azetidine hydrochloride

To a stirred solution of (2S,3S)-benzyl 2-benzyl-3-fluoroazetidine-1-carboxylate (115 mg, 384 mol) in methanol (1 mL) under nitrogen were added HCl in EtOH (9.0 M, 64.0 µL, 576 µmol) and 10 wt. % Pd/C (8.2 mg, 7.7 µmol). The resulting black suspension was purged by evacuation and then back filled with a stream of hydrogen (balloon) for three times. The mixture was stirred for 16 hours at room temperature under hydrogen atmosphere. The resulting suspension was filtered directly through a plug of dicalite. The filter cake was rinsed with methanol and the filtrate was concentrated in vacuo to afford the title compound (52 mg, 67%) as a light grey solid. MS (ISP): 166.1 ([M+H]$^+$).

Example 91

(2S,3R)-2-benzyl-3-fluoroazetidine

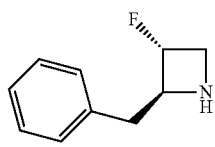 [SMILES: F[C@@H]1CN[C@H]1Cc1ccccc1]

The title compound was obtained in analogy to example 90 using (2S,3R)-benzyl 2-benzyl-3-fluoroazetidine-1-carboxylate in place of (2S,3S)-benzyl 2-benzyl-3-fluoroazetidine-1-carboxylate in step (f). Light grey solid. MS (ISP): 166.1 ([M+H]⁺).

Example 92

(2R,3R)-2-benzyl-3-fluoroazetidine

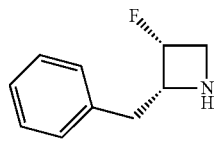 [SMILES: F[C@@H]1CN[C@@H]1Cc1ccccc1]

The title compound was obtained in analogy to example 90 using (R)-2-(benzyloxycarbonylamino)-3-phenylpropanoic acid (CAS 2448-45-5) in place of (S)-2-(benzyloxycarbonylamino)-3-phenylpropanoic acid in step (a), while in step (e), the epimers at C3 of (2R)-benzyl 2-benzyl-3-fluoroazetidine-1-carboxylate were separated using chiral HPLC (column: Lux Amylose, 25 mL/min, i-PrOH/heptane: 30/70; 860 bar; 205 nm) affording:

(−)-benzyl (2R,3S)-2-benzyl-3-fluoro-azetidine-1-carboxylate (16 mg, white solid), retention time=13 min.

(−)-benzyl (2R,3R)-2-benzyl-3-fluoro-azetidine-1-carboxylate (128 mg, colorless oil), retention time=19 min.

Light grey solid. MS (ISP): 166.1 ([M+H]⁺).

Example 93

(2R,3S)-2-benzyl-3-fluoroazetidine

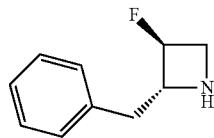 [SMILES: F[C@H]1CN[C@@H]1Cc1ccccc1]

To a stirred solution of (2R,3 S)-benzyl 2-benzyl-3-fluoroazetidine-1-carboxylate (16 mg, 53.5 mol) in methanol (1 mL) under nitrogen were added HCl in EtOH (9.0 M, 8.9 μL, 80.1 μmol) and 10 wt. % Pd/C (1.1 mg, 1.1 μmol). The resulting black suspension was purged by evacuation and then back filled with a stream of hydrogen (balloon) for three times. The mixture was stirred for 16 hours at room temperature under hydrogen atmosphere. The resulting suspension was filtered directly through a plug of dicalite. The filter cake was rinsed with methanol and the filtrate was concentrated in vacuo to afford the title compound (10 mg, 93%) as a light grey solid. MS (ISP): 166.1 ([M+H]⁺).

Example 94

(2S,3S)-2-benzyl-3-methoxyazetidine

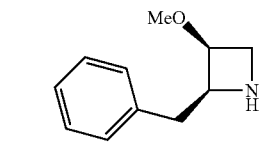 [SMILES: CO[C@H]1CN[C@H]1Cc1ccccc1]

a) (2S)-benzyl 2-benzyl-3-methoxyazetidine-1-carboxylate

To a stirred solution of (2S)-benzyl 2-benzyl-3-hydroxyazetidine-1-carboxylate (300 mg, 1.01 mmol) in THF (10 mL) was added at room temperature NaH (53.3 mg, 1.11 mmol, 60% in mineral oil). After 30 min, iodomethane (87.9 μL, 1.41 mmol) was added and the reaction was stirred at room temperature overnight. The reaction was quenched by careful addition of saturated aqueous NaHCO₃, diluted with water and extracted with EtOAc. The combined organic extracts were washed with brine, dried (MgSO₄) and concentrated in vacuo. The crude residue was purified by flash chromatography (silica gel, gradient: 5% to 40% EtOAc in heptane) to afford the title compound (227 mg, 72%, colorless oil) as a 4:1 epimeric mixture at C3. MS (ISP): 312.2 ([M+H]⁺).

b) benzyl-(2S,3S)-2-benzyl-3-methoxyazetidine-1-carboxylate

The epimers at C3 of (2S)-benzyl 2-benzyl-3-methoxyazetidine-1-carboxylate (227 mg, 729 μmol) were separated using chiral HPLC (column: Lux Amylose, 25 mL/min, EtOH/heptane: 40/60; 950 bar; 205 nm) affording:

(+)-benzyl (2S,3S)-2-benzyl-3-methoxyazetidine-1-carboxylate (164 mg, yellow oil), retention time=13 min.

(+)-benzyl (2S,3R)-2-benzyl-3-methoxyazetidine-1-carboxylate (35 mg, light yellow oil), retention time=24 min.

c) (2S,3S)-2-benzyl-3-methoxyazetidine hydrochloride

To a stirred solution of (2S,3S)-benzyl 2-benzyl-3-methoxyazetidine-1-carboxylate (164 mg, 527 μmol) in methanol (1 mL) under nitrogen were added HCl in EtOH (9.0 M, 87.8 μL, 791 μmol) followed by 10 wt. % Pd/C (11.2 mg, 10.5 μmol). The resulting black suspension was purged by evacuation and then back filled with a stream of hydrogen (balloon) for three times. The mixture was stirred for 16 hours at room temperature under hydrogen atmosphere. The resulting suspension was filtered directly through a plug of dicalite. The filter cake was rinsed with methanol and the filtrate was concentrated in vacuo to afford the title compound (97 mg, 86%) as a white solid. MS (ISP): 178.1 ([M+H]⁺).

Example 95

(2S,3R)-2-benzyl-3-methoxyazetidine

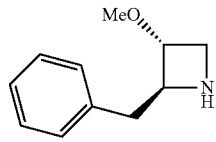 [SMILES: CO[C@@H]1CN[C@H]1Cc1ccccc1]

The title compound was obtained in analogy to example 94 using (2S,3R)-benzyl 2-benzyl-3-methoxyazetidine-1-carboxylate in place of (2S,3S)-benzyl 2-benzyl-3-methoxyazetidine-1-carboxylate in step (c). Light grey solid. MS (ISP): 178.1 ([M+H]$^+$).

Example 96

(2S,3S)-3-fluoro-2-(4-methoxybenzyl)azetidine

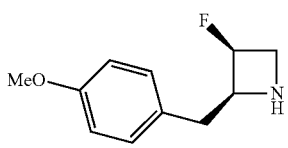 [SMILES: COc1ccc(C[C@@H]2NC[C@@H]2F)cc1]

a) (S)-benzyl 4-diazo-1-(4-methoxyphenyl)-3-oxobutan-2-ylcarbamate

To a stirred solution of (S)-2-(benzyloxycarbonylamino)-3-(4-methoxyphenyl)propanoic acid (10.7 g, 32.5 mmol, CAS 17554-34-6) in CH$_2$Cl$_2$ (107 mL) was added dropwise 1-chloro-N,N,2-trimethylpropenylamine (4.94 mL, 37.4 mmol) at room temperature. After 15 min, the reaction mixture was cooled to −10° C. and a solution of (trimethylsilyl)diazomethane in hexane (2.0 M, 19.5 mL, 39.0 mmol) was slowly added (caution: exothermic!). The reaction mixture was allowed to warm to room temperature till a red solution was obtained then the excess of diazomethane was destroyed by addition of AcOH (371 µL, 6.68 mmol) (caution: N$_2$ evolution!). The solvent was reduced to 10 mL by rotatory evaporation and the resulting residue was purified by flash chromatography (silica gel, gradient: 5% to 50% EtOAc in heptane to afford the title compound (970 mg, 8%) as a yellow oil. MS (ISP): 326.1 ([M−N$_2$+H]$^+$).

b) (S)-benzyl 2-(4-methoxybenzyl)-3-oxoazetidine-1-carboxylate

To a stirred solution of (S)-benzyl 4-diazo-1-(4-methoxyphenyl)-3-oxobutan-2-ylcarbamate (965 mg, 2.73 mmol) in CH$_2$Cl$_2$ (14 mL) was added Et$_3$N (4.82 µL, 34.8 µmol) followed by 4 Å molecular sieves (~0.5 g). The reaction mixture was cooled to −40° C. and Rh$_2$(OAc)$_4$ (24.1 mg, 54.6 µmol) was added in one portion. The resulting green solution was stirred at −40° C. for 1 hour before being allowed to warm to room temperature overnight. Triphenylphosphine (28.0 mg, 107 µmol) was added and the reaction mixture was stirred at room temperature for further 30 min till a red solution was obtained. The solvent was evaporated by rotatory evaporation and the resulting residue was purified by flash chromatography (silica gel, gradient: 5% to 40% EtOAc in heptane) to afford the title compound (387 mg, 44%) as a light yellow oil. MS (ISP): 326.2 ([M+H]$^+$).

c) (2S)-benzyl 3-hydroxy-2-(4-methoxybenzyl)azetidine-1-carboxylate

To a stirred solution of (S)-benzyl 2-(4-methoxybenzyl)-3-oxoazetidine-1-carboxylate (379 mg, 1.16 mmol) in THF (4 mL) at 0° C. was added sodium borohydride (88.1 mg, 2.33 mmol) and the reaction mixture was stirred at room temperature for 1 hour. The reaction mixture was partitioned between saturated aqueous NH$_4$Cl and EtOAc. The organic layers were separated, washed with brine, dried (MgSO$_4$) and concentrated in vacuo. The residue was purified by flash chromatography (silica gel, gradient: 5% to 50% EtOAc in heptane) to afford the title compound (270 mg, 71%, light yellow oil) as a 4:1 epimeric mixture at C3. MS (ISP): 328.2 ([M+H]$^+$).

d) (2 S)-benzyl-3-fluoro-2-(4-methoxybenzyl)azetidine-1-carboxylate

To a stirred solution of triethylamine (41.7 mg, 57.2 µL) and Et$_3$N.(HF)$_3$ (133 mg, 825 µmol) in CH$_2$Cl$_2$ (1.35 mL) were added XtalFluor-E® (142 mg, 618 µmol) followed by (2S)-benzyl 3-hydroxy-2-(4-methoxybenzyl)azetidine-1-carboxylate (0.135 g, 412 µmol). The reaction mixture was stirred at room temperature for 1 hour before being quenched by addition of water and saturated aqueous NaHCO$_3$. The mixture was extracted with CH$_2$Cl$_2$ and the combined organic extracts were washed with brine, dried (MgSO$_4$) and concentrated in vacuo. The residue was purified by flash chromatography to afford the title compound (108 mg, 80%, light yellow oil) as a 4:1 epimeric mixture at C3. MS (ISP): 330.2 ([M+H]$^+$).

e) (2S,3S)-benzyl 3-fluoro-2-(4-methoxybenzyl)azetidine-1-carboxylate

The epimers at C3 of (2S)-benzyl 3-fluoro-2-(4-methoxybenzyl)azetidine-1-carboxylate were separated using chiral HPLC (column: Chiralpak AD, 35 mL/min, i-PrOH/heptane: 10/90; 15 bar; 205 nm) affording:

(+)-benzyl (2S,3R)-3-fluoro-2-(4-methoxybenzyl)azetidine-1-carboxylate (20 mg, colorless oil), retention time=80 min.

(+)-benzyl (2S,3S)-3-fluoro-2-(4-methoxybenzyl)azetidine-1-carboxylate (59 mg, solid white), retention time=94 min.

f) (2S,3S)-3-fluoro-2-(4-methoxybenzyl)azetidine hydrochloride

To a stirred solution of (2S,3S)-benzyl 3-fluoro-2-(4-methoxybenzyl)azetidine-1-carboxylate (59 mg, 179 µmol) in methanol (1 mL) under nitrogen were added HCl in EtOH (9.0 M, 29.9 µL, 269 µmol) and 10 wt. % Pd/C (3.82 mg, 3.58 mol). The resulting black suspension was purged by evacuation and then back filled with a stream of hydrogen (balloon) for three times. The mixture was stirred for 16 hours at room temperature under hydrogen atmosphere. The resulting suspension was filtered directly through a plug of dicalite. The filter cake was rinsed with methanol and the filtrate was concentrated in vacuo to afford the title compound (33 mg, 80%) as a light grey solid. MS (ISP): 196.1 ([M+H]$^+$).

Example 97

(2S,3R)-3-fluoro-2-(4-methoxybenzyl)azetidine

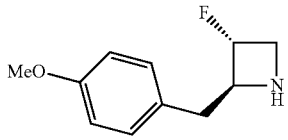 [SMILES: COc1ccc(C[C@@H]2NC[C@H]2F)cc1]

The title compound was obtained in analogy to example 96 using (2S,3R)-benzyl 3-fluoro-2-(4-methoxybenzyl)azetidine-1-carboxylate in place of (2S,3S)-benzyl 3-fluoro-2-(4-methoxybenzyl)azetidine-1-carboxylate in step (f). Light grey solid. MS (ISP): 196.1 ([M+H]$^+$).

Example 98

(2R,3R)-3-fluoro-2-(4-methoxybenzyl)azetidine

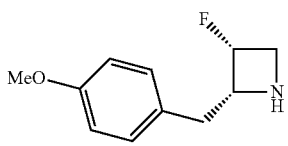 [SMILES: COc1ccc(C[C@H]2NC[C@H]2F)cc1]

The title compound was obtained in analogy to example 96 using (R)-2-(benzyloxycarbonylamino)-3-(4-methoxyphenyl)propanoic acid (CAS 65806-89-5) in place of (S)-2-(benzyloxycarbonylamino)-3-(4-methoxyphenyl)propanoic acid in step (a), while in step (e), the epimers at C3 of (2R)-benzyl 3-fluoro-2-(4-methoxybenzyl)azetidine-1-carboxylate were separated using chiral HPLC (column: chiralpak AD, 35 mL/min, i-PrOH/heptane: 10/90; 15 bar; 205 nm) affording:
 (−)-(2R,3S)-3-fluoro-2-(4-methoxybenzyl)azetidine-1-carboxylate (5 mg, colorless oil), retention time=84 min.
 (−)-(2R,3R)-3-fluoro-2-(4-methoxybenzyl)azetidine-1-carboxylate (20 mg, white solid), retention time=107 min.
 Light grey oil. MS (ISP): 196.1 ([M+H]$^+$).

Example 99

(2R,3S)-3-fluoro-2-(4-methoxybenzyl)azetidine

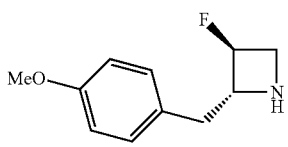 [SMILES: COc1ccc(C[C@H]2NC[C@@H]2F)cc1]

To a stirred solution of (2R,3S)-benzyl 3-fluoro-2-(4-methoxybenzyl)azetidine-1-carboxylate (5 mg, 15.2 μmol) in methanol (0.5 mL) under nitrogen were added HCl in EtOH (9.0 M, 2.5 μL, 22.8 μmol) and 10 wt. % Pd/C (0.3 mg, 0.3 μmol). The resulting black suspension was purged by evacuation and then back filled with a stream of hydrogen (balloon) for three times. The mixture was stirred for 16 hours at room temperature under hydrogen atmosphere. The resulting suspension was filtered directly through a plug of dicalite. The filter cake was rinsed with methanol and the filtrate was concentrated in vacuo to afford the title compound (2.3 mg, 65%) as a light grey solid. MS (ISP): 196.1 ([M+H]$^+$).

Example 100

(2R,3R)-2-benzyl-3-methoxyazetidine

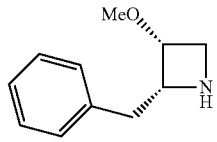 [SMILES: CO[C@@H]1CN[C@@H]1Cc1ccccc1]

a) (2R)-benzyl 2-benzyl-3-hydroxyazetidine-1-carboxylate

The title compound was obtained in analogy to example 90 (steps a, b and c) using (R)-2-(benzyloxycarbonylamino)-3-phenylpropanoic acid (CAS 2448-45-5) in place of (S)-2-(benzyloxycarbonylamino)-3-phenylpropanoic acid in step (a). Colorless oil. 4:1 mixture of epimers at C3. MS (ISP): 298.2 ([M+H]$^+$).

b) (2R)-benzyl 2-benzyl-3-methoxyazetidine-1-carboxylate

To a stirred solution of (2R)-benzyl 2-benzyl-3-hydroxyazetidine-1-carboxylate (0.300 g, 1.01 mmol) in THF (10 mL) was added at room temperature NaH (53.3 mg, 1.11 mmol, 60% in mineral oil). After 30 min, iodomethane (87.9 μL, 1.41 mmol) was added and the reaction was stirred at room temperature overnight. The reaction was quenched by careful addition of saturated aqueous NaHCO$_3$, diluted with water and extracted with EtOAc. The combined organic extracts were washed with brine, dried (MgSO$_4$) and concentrated in vacuo. The crude residue was purified by flash chromatography (silica gel, gradient: 5% to 40% EtOAc in heptane) to afford the title compound (232 mg, 74%, colorless oil) as a 4:1 epimeric mixture at C3. MS (ISP): 312.2 ([M+H]$^+$).

c) benzyl-(2R,3R)-2-benzyl-3-methoxyazetidine-1-carboxylate

The epimers at C3 of (2R)-benzyl 2-benzyl-3-methoxyazetidine-1-carboxylate (230 mg, 739 mol) were separated using chiral HPLC (column: Chiralpak AD, 35 mL/min, EtOH/heptane 18/82; 15 bar; 205 nm) affording:
 (−)-benzyl (2R,3R)-2-benzyl-3-methoxyazetidine-1-carboxylate (124 mg, yellow oil), retention time=54 min.
 (−)-benzyl (2R,3S)-2-benzyl-3-methoxyazetidine-1-carboxylate (31 mg, light yellow oil), retention time=71 min.

d) (2R,3R)-2-benzyl-3-methoxyazetidine hydrochloride

To a stirred solution of (2R,3R)-benzyl 2-benzyl-3-methoxyazetidine-1-carboxylate (124 mg, 398 μmol) in methanol (1 mL) under nitrogen were added HCl in EtOH (9.0 M, 66.3 μL, 597 mol) and 10 wt. % Pd/C (8.4 mg, 7.9 μmol). The resulting black suspension was purged by evacuation and then back filled with a stream of hydrogen (balloon) for three times. The mixture was stirred for 16 hours at room temperature under hydrogen atmosphere. The resulting suspension was filtered directly through a plug of dicalite. The filter cake was rinsed with methanol and the filtrate was concentrated in vacuo to afford the title compound (75 mg, 88%) as a light grey solid. MS (ISP): 178.1 ([M+H]$^+$).

Example 101

(2R,3S)-2-benzyl-3-methoxyazetidine

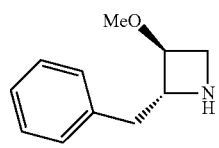 [SMILES: CO[C@H]1CN[C@@H]1Cc1ccccc1]

The title compound was obtained in analogy to example 100 using (2R,3S)-benzyl 2-benzyl-3-methoxyazetidine-1-carboxylate in place of (2R,3R)-benzyl 2-benzyl-3-methoxyazetidine-1-carboxylate in step (d). Light grey solid. MS (ISP): 178.1 ([M+H]$^+$).

Example 102

3-ethyl-N-(4-(((2S,3S)-3-fluoroazetidin-2-yl)methyl)phenyl)-4-methyl-1H-pyrazole-5-carboxamide

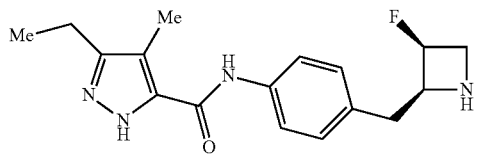 [SMILES: CCc1n[nH]c(C(=O)Nc2ccc(C[C@@H]3NC[C@@H]3F)cc2)c1C]

a) (2S,3S)-benzyl 2-benzyl-3-hydroxyazetidine-1-carboxylate

To a stirred solution of borane dimethyl sulfide complex (11.4 mL, 22.7 mmol) and (R)-(+)-2-methyl-CBS-oxazaborolidine in THF (1.0 M, 4.54 mL, 4.54 mmol, CAS 112022-83-0) in THF (67 mL) at 0° C. was added over 10 min a solution of (S)-benzyl 2-benzyl-3-oxoazetidine-1-carboxylate (6.71 g, 22.7 mmol) in THF (33.6 mL). The reaction mixture was stirred at 0° C. for 2 hours before being quenched by careful (gas evolution and exothermic!) addition of aqueous HCl (6.0 M, 9.0 mL, 54.0 mmol). The mixture was stirred at room temperature for 10 min, then poured into water and extracted with EtOAc. The combined organic extracts were washed with brine, dried (MgSO$_4$) and concentrated in vacuo. The residue was purified by flash chromatography (silica gel, gradient: 5% to 50% EtOAc in heptane) to afford the title compound (5.11 g, 76%, 96:4 dr) as a light yellow solid. MS (ISP): 298.1 ([M+H]$^+$).

b) (2S,3S)-benzyl 2-benzyl-3-fluoroazetidine-1-carboxylate

To a stirred solution of triethylamine (1.78 g, 2.44 mL, 17.6 mmol) and Et$_3$N.(HF)$_3$ (5.67 g, 35.1 mmol) in CH$_2$Cl$_2$ (50 mL) were added XtalFluor-E® (6.04 g, 26.4 mmol) followed by (2S,3S)-benzyl 2-benzyl-3-hydroxyazetidine-1-carboxylate (5.23 g, 17.6 mmol). The reaction mixture was stirred at room temperature for 1 hour before being quenched by addition of water and saturated aqueous NaHCO$_3$. The mixture was extracted with CH$_2$Cl$_2$ and the combined organic extracts were washed with brine, dried (MgSO$_4$) and concentrated in vacuo. The residue was purified by flash chromatography (silica gel, gradient 5% to 40% EtOAc in heptane) to afford the title compound (3.33 g, 63%) as a white solid. MS (ISP): 300.1 ([M+H]$^+$).

c) (2S,3S)-2-benzyl-3-fluoro-azetidine hydrochloride

To a stirred solution of (2S,3S)-benzyl 2-benzyl-3-fluoroazetidine-1-carboxylate (3.33 g, 11.1 mmol) in methanol (214 mL) under nitrogen were added HCl in EtOH (9.0 M, 1.85 mL, 16.7 mmol) and 10 wt. % Pd/C (237 mg, 222 µmol). The resulting black suspension was purged by evacuation and then back filled with a stream of hydrogen (balloon) for three times. The mixture was stirred for 16 hours at room temperature under hydrogen atmosphere. The resulting suspension was filtered directly through a plug of dicalite. The filter cake was rinsed with methanol and the filtrate was concentrated in vacuo to afford the title compound (2.23 g, 99%) as a grey solid. MS (ISP): 166.1 ([M+H]$^+$).

d) (2S,3S) 3-fluoro-2-(4-nitrobenzyl)azetidine

To a stirred suspension of (2S,3S)-2-benzyl-3-fluoroazetidine hydrochloride (2.23 g, 11.1 mmol) in CH$_2$Cl$_2$ (20 mL) at −20° C. were added dropwise sulfuric acid (8.84 mL, 166 mmol) and nitric acid (0.836 mL, 12.2 mmol, 65 wt. %). The reaction mixture was allowed to warm to room temperature. After 30 min, the reaction mixture was poured into ice and water and the pH was adjusted to 10-11 by addition of 2.0 M aqueous NaOH. The mixture was extracted with CH$_2$Cl$_2$ and the combined organic extracts were dried (MgSO$_4$) and concentrated in vacuo to afford the title compound (2.29 g, 99%, orange oil) together with low amount of ortho and meta-isomers. MS (ISP): 211.1 ([M+H]$^+$).

e) (2S,3S)-tert-butyl 3-fluoro-2-(4-nitrobenzyl)azetidine-1-carboxylate

To a stirred solution of (2S,3S) 3-fluoro-2-(4-nitrobenzyl)azetidine (2.29 g, 10.9 mmol) in methanol (60 mL) were added di-tert-butyl dicarbonate (4.83 g, 22.1 mmol) and N,N-diisopropylethylamine (3.86 mL, 22.1 mmol) and the reaction was stirred at room temperature for 1 hour. The reaction was poured into water and extracted with EtOAc. The combined organic extracts were washed with brine, dried (MgSO$_4$) and concentrated in vacuo. The crude residue was purified by flash chromatography (silica gel, gradient: 5% to 50% EtOAc in heptane) to afford the title compound (2.97 g, 87%, light yellow oil) together with low amount of ortho and meta-isomers. MS (ISP): 255.1 ([M-C$_4$H$_8$+H]).

f) (2S,3S)-tert-butyl 3-fluoro-2-(4-aminobenzyl)azetidine-1-carboxylate

To a stirred solution of (2S,3S)-tert-butyl 3-fluoro-2-(4-nitrobenzyl)azetidine-1-carboxylate (2.97 g, 9.57 mmol) in MeOH (130 mL) under nitrogen was added 10 wt. % Pd/C (204 mg, 191 µmol). The resulting black suspension was purged by evacuation and then back filled with a stream of hydrogen (balloon) for three times. The mixture was stirred for 16 hours at room temperature under hydrogen atmosphere. The resulting suspension was filtered directly through a plug of dicalite. The filter cake was rinsed with MeOH and the filtrate was concentrated in vacuo. The crude residue was purified by flash chromatography (silica gel, gradient: 5% to 50% EtOAc in heptane) to yield the title compound together with meta-isomer. The minor isomer (meta) was removed by preparative HPLC (column: Reprosil Chiral-NR, 35 mL/min, EtOH/heptane: 15/85, 205 nm, 240 psi) to afford the title compound (1.5 g, 56%) as an orange solid. MS (ISP): 225.1 ([M-C$_4$H$_8$+H]$^+$).

g) (2S,3S)-tert-butyl 2-(4-(3-ethyl-4-methyl-1H-pyrazole-5-carboxamido)benzyl)-3-fluoroazetidine-1-carboxylate To a stirred solution of 3-ethyl-4-methyl-1H-pyrazole-5-carboxylic acid (52.8 mg, 342 μmol) in MeOH (1.91 mL) was added (2S,3S)-tert-butyl 2-(4-aminobenzyl)-3-fluoroazetidine-1-carboxylate (80 mg, 285 μmol). The mixture was cooled to 0° C., before the dropwise addition of a solution of 4-(4,6-dimethoxy-1,3,5-triazin-2-yl)-4-methylmorpholin-4-ium chloride (103 mg, 371 μmol) in MeOH (1.6 mL). The reaction mixture was stirred at 0° C. for 1 hour then allowed to warm to room temperature. After 2 hours, the reaction was heated to 50° C. for 1 hour. The solvent was removed by rotatory evaporation and the resulting residue was purified by flash chromatography (silica gel, gradient: 10% to 60% EtOAc in heptane) to afford the title compound (87 mg, 66%) as a light yellow oil. MS (ISN): 415.3 ([M–H]$^-$).

h) 3-ethyl-N-(4-(((2S,3S)-3-fluoroazetidin-2-yl)methyl)phenyl)-4-methyl-1H-pyrazole-5-carboxamide hydrochloride To a stirred solution of (2S,3S)-tert-butyl 2-(4-(3-ethyl-4-methyl-1H-pyrazole-5-carboxamido)benzyl)-3-fluoroazetidine-1-carboxylate (87 mg, 209 μmol) in 1,4-dioxane (0.5 mL) was added a 4.0 M solution of HCl in 1,4-dioxane (0.780 mL, 3.13 mmol). The reaction mixture was stirred at room temperature overnight before all volatiles were removed under high vacuum. The residue was triturated in EtOH/heptane, filtered and dried under high vacuum to afford the title compound (47 mg, 64%) as an off-white solid. MS (ISP): 317.2 ([M+H]$^+$).

Example 103

3-ethyl-N-(4-(((2R,3R)-3-fluoroazetidin-2-yl)methyl)phenyl)-4-methyl-1H-pyrazole-5-carboxamide

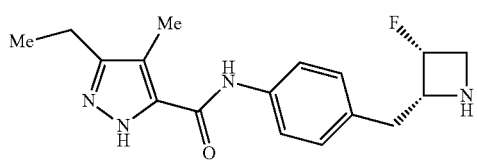 [SMILES: CCc1n[nH]c(C(=O)Nc2ccc(C[C@H]3NC[C@H]3F)cc2)c1C]

The title compound was obtained in analogy to example 90 using (R)-2-(benzyloxycarbonylamino)-3-phenylpropanoic acid (CAS 2448-45-5) in place of (S)-2-(benzyloxycarbonylamino)-3-phenylpropanoic acid in step (a) and to example 102 using (S)-(–)-2-methyl-CBS-oxazaborolidine (CAS 112022-81-8) in place of (R)-(+)-2-methyl-CBS-oxazaborolidine in step (a). Off-white solid. MS (ISP): 317.2 ([M+H]$^+$).

Example 104

N-(4-(((2S,3S)-3-fluoroazetidin-2-yl)methyl)phenyl)-2-(trifluoromethyl)isonicotinamide

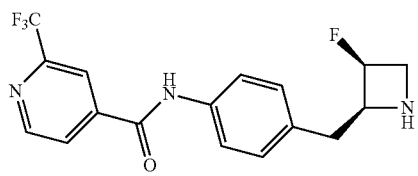 [SMILES: O=C(Nc1ccc(C[C@@H]2NC[C@@H]2F)cc1)c1ccnc(C(F)(F)F)c1]

a) (2S,3S)-tert-butyl 3-fluoro-2-(4-(2-(trifluoromethyl)isonicotinamide)benzyl)azetidine-1-carboxylate To a stirred suspension of 2-(trifluoromethyl)isonicotinic acid (75 mg, 393 μmol) in CH$_2$Cl$_2$ (0.5 mL) at room temperature was added 1-chloro-N,N,2-trimethylpropenylamine (54.3 μL, 411 μmol). After 30 minutes, a solution of (2S,3S)-tert-butyl 3-fluoro-2-(4-aminobenzyl)azetidine-1-carboxylate (100 mg, 357 μmol) and N,N-diisopropylethylamine (88.7 μL, 536 μmol) in DMF (500 μL) was added and the mixture was stirred at room temperature for 1 hour. The reaction was then poured into water and extracted with CH$_2$Cl$_2$. The combined organic extracts were washed with brine, dried (MgSO$_4$) and concentrated in vacuo. The residue was purified by flash chromatography (silica gel, gradient: 10% to 50% EtOAc in heptane) to afford the title compound (118 mg, 73%) as a white foam. MS (ISN): 452.3 ([M–H]$^-$).

b) N-(4-(((2S,3S)-3-fluoroazetidin-2-yl)methyl)phenyl)-2-(trifluoromethyl)isonicotinamide 2,2,2-trifluoroacetic acid To a stirred solution of (2S,3S)-tert-butyl 3-fluoro-2-(4-(2-(trifluoromethyl)isonicotinamide)benzyl)azetidine-1-carboxylate (118 mg, 260 μmol) in CH$_2$Cl$_2$ (1.0 mL) was added 2,2,2-trifluoroacetic acid (0.5 mL). The reaction mixture was stirred for 2 hours at room temperature before all volatiles were removed under high vacuum. The residue was triturated in EtOH/heptane, filtered and dried under high vacuum to afford the title compound (77 mg, 63%) as a light yellow solid. MS (ISP): 354.2 ([M+H]$^+$).

Example 105

1-[4-[(3-fluoroazetidin-3-yl)methyl]phenyl]-3-[4-(trifluoromethyl)phenyl]urea

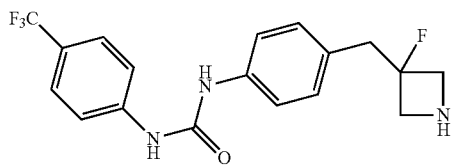 [SMILES: O=C(Nc1ccc(CC2(F)CNC2)cc1)Nc1ccc(C(F)(F)F)cc1]

a) tert-butyl 3-fluoro-3-[[4-[[4-(trifluoromethyl)phenyl]carbamoylamino]phenyl]methyl]azetidine-1-carboxylate To a stirred solution of tert-butyl 3-(4-aminobenzyl)-3-fluoroazetidine-1-carboxylate (30 mg, 107 µmol) in THF (2.0 mL) was added 4-(trifluoromethyl)phenyl isocyanate (24 mg, 128 µmol, CAS 1548-13-6). The reaction mixture was stirred at room temperature for 2 hours before all volatiles were evaporated. The crude residue was purified by flash column chromatography (silica gel; gradient: 0% to 60% EtOAc in heptane) to afford the title compound (35.4 mg, 71%) as a white solid. MS (ISP): 466.2 ([M−H]$^-$).

b) 1-[4-[(3-fluoroazetidin-3-yl)methyl]phenyl]-3-[4-(trifluoromethyl)phenyl]urea hydrochloride To a stirred solution of tert-butyl 3-fluoro-3-[[4-[[4-(trifluoromethyl)phenyl]carbamoylamino]phenyl]methyl]azetidine-1-carboxylate (35.4 mg, 76 µmol) in 1,4-dioxane (0.5 mL) was added a 4.0 M solution of HCl in 1,4-dioxane (0.25 mL). The reaction mixture was stirred at room temperature overnight. The resulting suspension was filtered through a sintered funnel. The collected hydrochloride salt was washed with further anhydrous diethyl ether then dried under high vacuum to afford the title compound (25.8 mg, 84%) as a white solid. MS (ISP): 368.2 ([M+H]$^+$).

Example 106

1-[4-[(3-fluoroazetidin-3-yl)methyl]phenyl]-3-(4-methoxyphenyl)urea

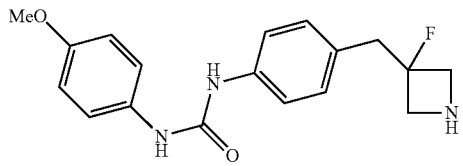 [SMILES: COc1ccc(NC(=O)Nc2ccc(CC3(F)CNC3)cc2)cc1]

The title compound was obtained in analogy to example 105 using 4-(methoxy)phenyl isocyanate (CAS 5416-93-3) in place of 4-(trifluoromethyl)phenyl isocyanate in step (a). White solid. MS (ISP): 330.1 ([M+H]$^+$).

Example 107

1-(3-chlorophenyl)-3-[4-[(3-fluoroazetidin-3-yl)methyl]phenyl]urea

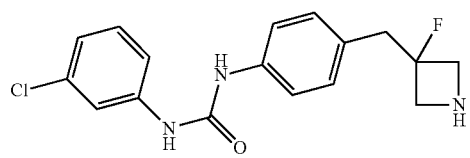 [SMILES: O=C(Nc1ccc(CC2(F)CNC2)cc1)Nc1cccc(Cl)c1]

The title compound was obtained in analogy to example 105 using 3-chlorophenyl isocyanate (CAS 2909-38-8) in place of 4-(trifluoromethyl)phenyl isocyanate in step (a). White solid. MS (ISP): 336.2 ([{$^{37}$Cl}M+H]$^+$), 334.2 ([{$^{35}$Cl}M+H]$^+$).

Example 108

1-[4-(azetidin-3-yloxy)phenyl]-3-(4-methoxyphenyl)urea

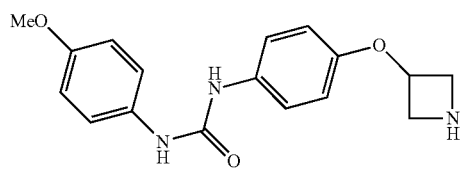 [SMILES: COc1ccc(NC(=O)Nc2ccc(OC3CNC3)cc2)cc1]

The title compound was obtained in analogy to example 105 using 4-(methoxy)phenyl isocyanate (CAS 5416-93-3) in place of 4-(trifluoromethyl)phenyl isocyanate and tert-butyl 3-(4-aminophenoxy)azetidine-1-carboxylate in place of tert-butyl 3-(4-aminobenzyl)-3-fluoroazetidine-1-carboxylate in step (a). White solid. MS (ISP): 314.2 ([M+H]$^+$).

Example 109

1-[4-(azetidin-3-yloxy)phenyl]-3-(3-chlorophenyl)urea

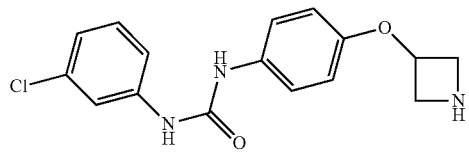 [SMILES: O=C(Nc1ccc(OC2CNC2)cc1)Nc1cccc(Cl)c1]

The title compound was obtained in analogy to example 105 using 3-chlorophenyl isocyanate (CAS 2909-38-8) in place of 4-(trifluoromethyl)phenyl isocyanate and tert-butyl 3-(4-aminophenoxy)azetidine-1-carboxylate in place of tert-butyl 3-(4-aminobenzyl)-3-fluoroazetidine-1-carboxylate in step (a). White solid. MS (ISP): 320.2 ([{$^{37}$Cl}M+H]$^+$), 318.2 ([{$^{35}$Cl}M+H]$^+$).

Example 110

1-[4-(azetidin-3-ylsulfanyl)phenyl]-3-[4-(trifluoromethyl)phenyl]urea

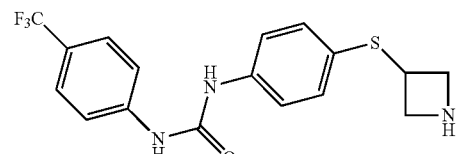

The title compound was obtained in analogy to example 105 using tert-butyl 3-(4-aminophenyl)sulfanylazetidine-1-carboxylate in place of tert-butyl 3-(4-aminobenzyl)-3-fluoroazetidine-1-carboxylate in step (a). White solid. MS (ISP): 368.0 ([M+H]$^+$).

Example 111

1-[4-(azetidin-3-ylsulfanyl)phenyl]-3-(4-methoxyphenyl)urea

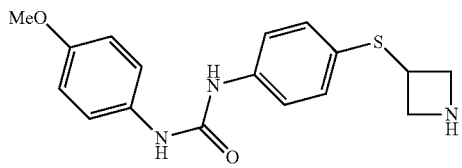 [SMILES: COc1ccc(NC(=O)Nc2ccc(SC3CNC3)cc2)cc1]

The title compound was obtained in analogy to example 105 using 4-(methoxy)phenyl isocyanate (CAS 5416-93-3) in place of 4-(trifluoromethyl)phenyl isocyanate and tert-butyl 3-(4-aminophenyl)sulfanylazetidine-1-carboxylate in place of tert-butyl 3-(4-aminobenzyl)-3-fluoroazetidine-1-carboxylate in step (a). White solid. MS (ISP): 330.2 ([M+H]$^+$).

Example 112

1-[4-(azetidin-3-ylsulfanyl)phenyl]-3-(3-chlorophenyl)urea

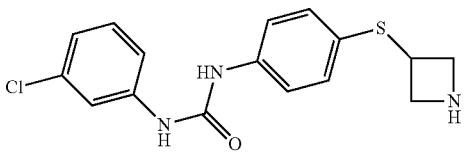 [SMILES: O=C(Nc1ccc(SC2CNC2)cc1)Nc1cccc(Cl)c1]

The title compound was obtained in analogy to example 105 using 3-chlorophenyl isocyanate (CAS 2909-38-8) in place of 4-(trifluoromethyl)phenyl isocyanate and tert-butyl 3-(4-aminophenyl)sulfanylazetidine-1-carboxylate in place of tert-butyl 3-(4-aminobenzyl)-3-fluoroazetidine-1-carboxylate in step (a). White solid. MS (ISP): 336.2 ([{$^{37}$Cl}M+H]$^+$), 334.1 ([{$^{35}$Cl}M+H]$^+$).

Example 113

1-[4-(azetidin-3-ylmethyl)phenyl]-3-[4-(trifluoromethyl)phenyl]urea

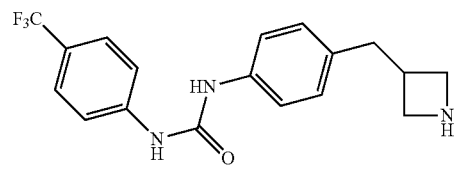 [SMILES: O=C(Nc1ccc(CC2CNC2)cc1)Nc1ccc(C(F)(F)F)cc1]

a) tert-butyl 3-[[4-[[4-(trifluoromethyl)phenyl]carbamoylamino]phenyl]methyl]azetidine-1-carboxylate To a stirred solution of tert-butyl 3-[(4-aminophenyl)methyl]azetidine-1-carboxylate (30 mg, 114 µmol) in THF (2.0 mL) was added 4-(trifluoromethyl)phenyl isocyanate (25.6 mg, 137 µmol, CAS 1548-13-6). The reaction mixture was stirred at room temperature for 2 hours before all volatiles were evaporated. The crude residue was purified by flash column chromatography (silica gel; gradient: 0% to 40% EtOAc in heptane) to afford the title compound (38.8 mg, 76%) as a white solid. MS (ISP): 448.1 ([M−H]$^−$).

b) 1-[4-(azetidin-3-ylmethyl)phenyl]-3-[4-(trifluoromethyl)phenyl]urea 2,2,2-trifluoroacetic acid To a stirred solution of tert-butyl 3-[[4-[[4-(trifluoromethyl)phenyl]carbamoylamino]phenyl]methyl]azetidine-1-carboxylate (35 mg, 78 µmol) in CH$_2$Cl$_2$ (1.0 mL) was added 2,2,2-trifluoroacetic acid (0.5 mL). The reaction mixture was stirred for 2 hours at room temperature before all volatiles were removed under high vacuum. The residue was triturated in EtOH/diethyl ether, filtered and dried under high vacuum to afford the title compound (27 mg, 75%) as a white solid. MS (ISP): 350.2 ([M+H]$^+$).

Example 114

1-[4-(azetidin-3-ylmethyl)phenyl]-3-(4-methoxyphenyl)urea

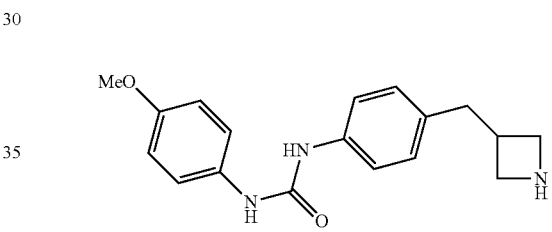

The title compound was obtained in analogy to example 113 using 4-(methoxy)phenyl isocyanate (CAS 5416-93-3) in place of 4-(trifluoromethyl)phenyl isocyanate in step (a). White solid. MS (ISP): 312.3 ([M+H]$^+$).

Example 115

1-[4-(azetidin-3-ylmethyl)phenyl]-3-(4-methoxyphenyl)urea

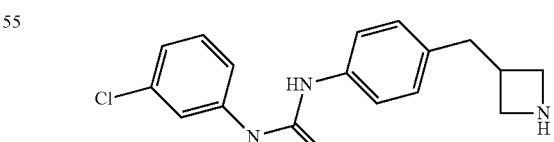

The title compound was obtained in analogy to example 113 using 3-chlorophenyl isocyanate (CAS 2909-38-8) in place of 4-(trifluoromethyl)phenyl isocyanate in step (a). White solid. MS (ISP): 318.2 ([{$^{37}$Cl}M+H]$^+$), 316.1 ([{$^{35}$Cl}M+H]$^+$).

Example 116

1-[4-(azetidin-3-ylidenemethyl)phenyl]-3-[4-(trifluoromethyl)phenyl]urea

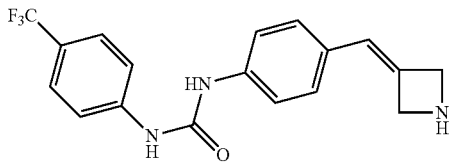 [SMILES: O=C(Nc1ccc(C=C2CNC2)cc1)Nc1ccc(C(F)(F)F)cc1]

The title compound was obtained in analogy to example 113 using tert-butyl 3-[(4-aminophenyl)methylene]azetidine-1-carboxylate in place of tert-butyl 3-[(4-aminophenyl)methyl]azetidine-1-carboxylate in step (a). White solid. MS (ISP): 348.2 ([M+H]$^+$).

Example 117

1-[4-(azetidin-3-ylidenemethyl)phenyl]-3-(4-methoxyphenyl)urea

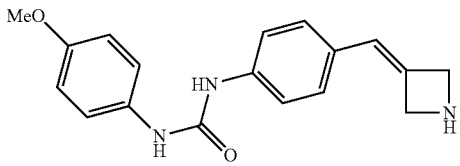 [SMILES: COc1ccc(NC(=O)Nc2ccc(C=C3CNC3)cc2)cc1]

The title compound was obtained in analogy to example 113 using 4-(methoxy)phenyl isocyanate (CAS 5416-93-3) in place of 4-(trifluoromethyl)phenyl isocyanate and tert-butyl 3-[(4-aminophenyl)methylene]azetidine-1-carboxylate in place of tert-butyl 3-[(4-aminophenyl)methyl]azetidine-1-carboxylate in step (a). White solid. MS (ISP): 310.3 ([M+H]$^+$).

Example 118

1-[4-(azetidin-3-ylidenemethyl)phenyl]-3-(3-chlorophenyl)urea

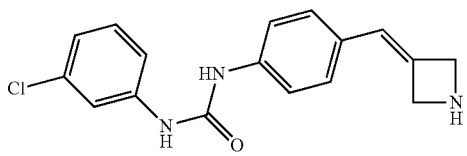 [SMILES: O=C(Nc1ccc(C=C2CNC2)cc1)Nc1cccc(Cl)c1]

The title compound was obtained in analogy to example 113 using 3-chlorophenyl isocyanate (CAS 2909-38-8) in place of 4-(trifluoromethyl)phenyl isocyanate and tert-butyl 3-[(4-aminophenyl)methylene]azetidine-1-carboxylate in place of tert-butyl 3-[(4-aminophenyl)methyl]azetidine-1-carboxylate in step (a). White solid. MS (ISP): 316.2 ([$^{37}$Cl]M+H]$^+$), 314.1 ([$^{35}$Cl]M+H]$^+$).

Example 119

N-(4-(((2R,3R)-3-fluoroazetidin-2-yl)methyl)phenyl)-6-methyl-2-(trifluoromethyl)pyrimidine-4-carboxamide

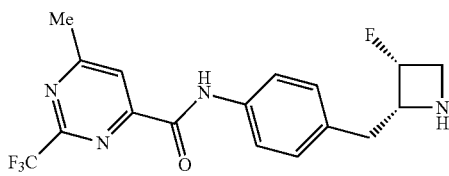 [SMILES: Cc1cc(C(=O)Nc2ccc(C[C@H]3NC[C@H]3F)cc2)nc(C(F)(F)F)n1]

a) (2R,3R)-3-Fluoro-2-{4-[(6-methyl-2-trifluoromethyl-pyrimidine-4-carbonyl)-amino]-benzyl}-azetidine-1-carboxylic acid tert-butyl ester To a stirred suspension of 6-methyl-2-trifluoromethyl-pyrimidine-4-carboxylic acid (81 mg, 393 µmol) in CH$_2$Cl$_2$ (0.5 mL) at room temperature was added 1-chloro-N,N,2-trimethypropenylamine (54.3 µL, 411 µmol). After 30 minutes, a solution of (2R,3R)-tert-butyl 3-fluoro-2-(4-aminobenzyl)azetidine-1-carboxylate (100 mg, 357 µmol) and N,N-diisopropylethylamine (88.7 µL, 536 µmol) in DMF (500 µL) was added and the mixture was stirred at room temperature for 1 hour. The reaction was then poured into water and extracted with CH$_2$Cl$_2$. The combined organic extracts were washed with brine, dried (MgSO$_4$) and concentrated in vacuo. The residue was purified by flash chromatography (silica gel, gradient: 10% to 50% EtOAc in heptane) to afford the title compound (167 mg, 100%) as a light yellow foam. MS (ISN): 467.3 ([M−H]$^-$).

b) N-(4-(((2R,3R)-3-fluoroazetidin-2-yl)methyl)phenyl)-6-methyl-2-(trifluoromethyl)pyrimidine-4-carboxamide To a stirred solution of (2R,3R)-3-Fluoro-2-{4-[(6-methyl-2-trifluoromethyl-pyrimidine-4-carbonyl)-amino]-benzyl}-azetidine-1-carboxylic acid tert-butyl ester (167 mg, 357 µmol) in 1,4-dioxane (0.5 mL) was added a 4.0 M solution of HCl in 1,4-dioxane (0.25 mL). The reaction mixture was stirred at room temperature overnight before all volatiles were evaporated. The residue was purified by preparative HPLC (mobile phase A: H$_2$O, B: CH$_3$CN with 0.05% Et$_3$N, C18 column) to afford the title compound (41 mg, 31%) as a light yellow solid. MS (ISP): 369.2 ([M+H]$^+$).

Example 120

N-(4-(((2R,3R)-3-fluoroazetidin-2-yl)methyl)phenyl)-2-methoxyisonicotinamide

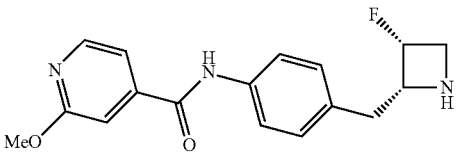 [SMILES: COc1cc(C(=O)Nc2ccc(C[C@H]3NC[C@H]3F)cc2)ccn1]

The title compound was obtained in analogy to example 119 using 2-methoxy-isonicotinic acid (CAS 105596-63-2) in place of 6-methyl-2-trifluoromethyl-pyrimidine-4-carboxylic acid in step (a). White solid. MS (ISP): 316.2 ([M+H]⁺).

Example 121

N-(4-(((2R,3R)-3-fluoroazetidin-2-yl)methyl)phenyl)-2-(trifluoromethyl)isonicotinamide

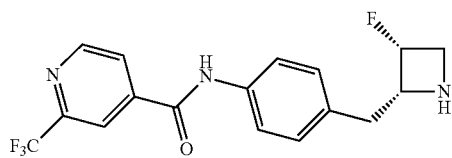 [SMILES: O=C(Nc1ccc(C[C@H]2NC[C@H]2F)cc1)c1ccnc(C(F)(F)F)c1]

The title compound was obtained in analogy to example 119 using 2-(trifluoromethyl) isonicotinic acid (CAS 131747-41-6) in place of 6-methyl-2-trifluoromethyl-pyrimidine-4-carboxylic acid in step (a). White foam. MS (ISP): 354.2 ([M+H]⁺).

Example 122

6-ethoxy-N-(4-(((2R,3R)-3-fluoroazetidin-2-yl)methyl)phenyl)nicotinamide

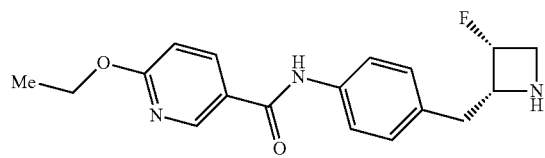 [SMILES: CCOc1ccc(C(=O)Nc2ccc(C[C@H]3NC[C@H]3F)cc2)cn1]

The title compound was obtained in analogy to example 119 using 6-ethoxypyridine-3-carboxylic acid (CAS 97455-65-7) in place of 6-methyl-2-trifluoromethyl-pyrimidine-4-carboxylic acid in step (a). White solid. MS (ISP): 330.2 ([M+H]⁺).

Example 123

N-(4-(((2R,3R)-3-fluoroazetidin-2-yl)methyl)phenyl)-2-(trifluoromethyl)pyrimidine-5-carboxamide

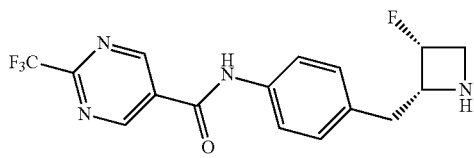 [SMILES: O=C(Nc1ccc(C[C@H]2NC[C@H]2F)cc1)c1cnc(C(F)(F)F)nc1]

The title compound was obtained in analogy to example 119 using 2-trifluoromethyl)pyrimidine-5-carboxylic acid (CAS 306960-77-0) in place of 6-methyl-2-trifluoromethyl-pyrimidine-4-carboxylic acid in step (a). White solid. MS (ISP): 355.2 ([M+H]⁺).

Example 124

2-cyclopropyl-N-(4-(((2R,3R)-3-fluoroazetidin-2-yl)methyl)phenyl)pyrimidine-5-carboxamide

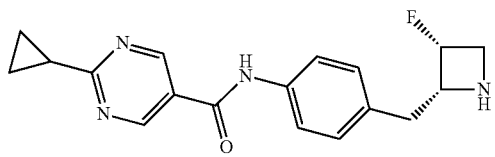 [SMILES: O=C(Nc1ccc(C[C@H]2NC[C@H]2F)cc1)c1cnc(C2CC2)nc1]

The title compound was obtained in analogy to example 119 using 2-cyclopropylpyrimidine-5-carboxylic acid (CAS 648423-79-4) in place of 6-methyl-2-trifluoromethyl-pyrimidine-4-carboxylic acid in step (a). White solid. MS (ISP): 327.2 ([M+H]⁺).

Example 125

N-(4-(((2R,3R)-3-fluoroazetidin-2-yl)methyl)phenyl)-3-isopropyl-1H-pyrazole-5-carboxamide

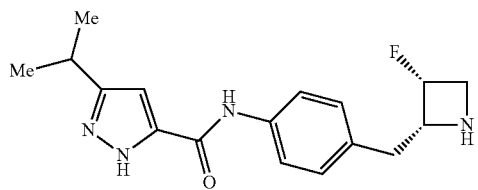 [SMILES: CC(C)c1cc(C(=O)Nc2ccc(C[C@H]3NC[C@H]3F)cc2)[nH]n1]

a) (2R,3R)-tert-butyl 3-fluoro-2-(4-(3-isopropyl-1H-pyrazole-5-carboxamido)benzyl)azetidine-1-carboxylate To a stirred solution of 3-isopropyl-1H-pyrazole-5-carboxylic acid (60.5 mg, 392 μmol) in MeOH (1.85 mL) was added (2R,3R)-tert-butyl 2-(4-aminobenzyl)-3-fluoroazetidine-1-carboxylate (0.100 g, 357 μmol). The mixture was cooled to 0° C., before the dropwise addition of a solution of 4-(4,6-dimethoxy-1,3,5-triazin-2-yl)-4-methylmorpholin-4-ium chloride (118 mg, 428 μmol) in MeOH (1.85 mL). The reaction mixture was stirred at 0° C. for 1 hour then allowed to warm to room temperature. After 2 hours, the reaction was heated to 50° C. for 1 hour. The solvent was removed by rotatory evaporation and the resulting residue was purified by preparative HPLC (mobile phase A: H₂O, B: CH₃CN with 0.05% Et₃N, C18 column) to afford the title compound (119 mg, 80%) as a white solid. MS (ISN): 415.3 ([M−H]⁻).

b) N-(4-(((2R,3R)-3-fluoroazetidin-2-yl)methyl)phenyl)-3-isopropyl-1H-pyrazole-5-carboxamide To a stirred solution of (2R,3R)-tert-butyl 3-fluoro-2-(4-(3-isopropyl-1H-pyrazole-5-carboxamido)benzyl)azetidine-1-carboxylate (119 mg, 286 μmol) in 1,4-dioxane (0.5 mL) was added a 4.0 M solution of HCl in 1,4-dioxane (0.25 mL). The reaction mixture was stirred at room temperature overnight before all volatiles were evaporated. The residue was purified by preparative HPLC (mobile phase A: H₂O, B:

CH₃CN with 0.05% Et₃N, C18 column) to afford the title compound (35 mg, 39%) as a white solid. MS (ISP): 317.2 ([M+H]⁺).

Example 126

N-(4-(((2S,3S)-3-fluoroazetidin-2-yl)methyl)phenyl)-6-methyl-2-(trifluoromethyl)pyrimidine-4-carboxamide

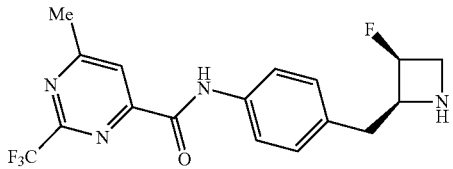 [SMILES: Cc1cc(C(=O)Nc2ccc(C[C@@H]3NC[C@@H]3F)cc2)nc(C(F)(F)F)n1]

a) tert-butyl (2S,3S)-3-fluoro-2-(4-(6-methyl-2-(trifluoromethyl)pyrimidine-4-carbonyl)amino)phenyl)methyl)azetidine-1-carboxylate To a stirred suspension of 6-methyl-2-trifluoromethyl-pyrimidine-4-carboxylic acid (81 mg, 393 mol) in CH₂Cl₂ (0.5 mL) at room temperature was added 1-chloro-N,N,2-trimethypropenylamine (54.3 µL, 411 µmol). After 30 minutes, a solution of (2S,3S)-tert-butyl 3-fluoro-2-(4-aminobenzyl)azetidine-1-carboxylate (100 mg, 357 µmol) and N,N-diisopropylethylamine (88.7 µL, 536 µmol) in DMF (500 µL) was added and the mixture was stirred at room temperature for 1 hour. The reaction was then poured into water and extracted with CH₂Cl₂. The combined organic extracts were washed with brine, dried (MgSO₄) and concentrated in vacuo. The residue was purified by flash chromatography (silica gel, gradient: 10% to 50% EtOAc in heptane to afford the title compound (164 mg, 98%) as a white foam. MS (ISN): 467.3 ([M–H]⁻).

b) N-(4-(((2S,3S)-3-fluoroazetidin-2-yl)methyl)phenyl)-6-methyl-2-(trifluoromethyl)pyrimidine-4-carboxamide 2,2,2-trifluoroacetic acid To a stirred solution of tert-butyl (2S,3S)-3-fluoro-2-(4-(6-methyl-2-(trifluoromethyl)pyrimidine-4-carbonyl)amino)phenyl)methyl)azetidine-1-carboxylate (164 mg, 350 µmol) in CH₂Cl₂ (1.0 mL) was added 2,2,2-trifluoroacetic acid (0.5 mL). The reaction mixture was stirred for 2 hours at room temperature before all volatiles were removed under high vacuum. The residue was triturated in EtOH/heptane, filtered and dried under high vacuum to afford the title compound (135 mg, 80%) as a white solid. MS (ISP): 369.2 ([M+H]⁺).

Example 127

N-(4-(((2S,3S)-3-fluoroazetidin-2-yl)methyl)phenyl)-2-methoxyisonicotinamide

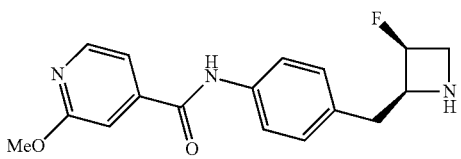 [SMILES: COc1cc(C(=O)Nc2ccc(C[C@@H]3NC[C@@H]3F)cc2)ccn1]

The title compound was obtained in analogy to example 126 using 2-methoxy-isonicotinic acid in place of 6-methyl-2-trifluoromethyl-pyrimidine-4-carboxylic acid in step (a). White solid. MS (ISP): 316.2 ([M+H]⁺).

Example 128

6-ethoxy-N-(4-(((2S,3S)-3-fluoroazetidin-2-yl)methyl)phenyl)nicotinamide

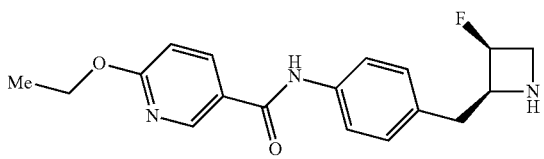 [SMILES: CCOc1ccc(C(=O)Nc2ccc(C[C@@H]3NC[C@@H]3F)cc2)cn1]

The title compound was obtained in analogy to example 126 using 6-ethoxypyridine-3-carboxylic acid in place of 6-methyl-2-trifluoromethyl-pyrimidine-4-carboxylic acid in step (a). White solid. MS (ISP): 330.2 ([M+H]⁺).

Example 129

2-cyclopropyl-N-(4-(((2S,3S)-3-fluoroazetidin-2-yl)methyl)phenyl)pyrimidine-5-carboxamide

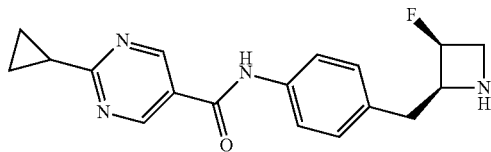 [SMILES: O=C(Nc1ccc(C[C@@H]2NC[C@@H]2F)cc1)c1cnc(C2CC2)nc1]

The title compound was obtained in analogy to example 126 using 2-cyclopropylpyrimidine-5-carboxylic acid in place of 6-methyl-2-trifluoromethyl-pyrimidine-4-carboxylic acid in step (a). White solid. MS (ISP): 327.2 ([M+H]⁺).

Example 130

N-(4-(((2S,3S)-3-fluoroazetidin-2-yl)methyl)phenyl)-2-(trifluoromethyl)pyrimidine-5-carboxamide

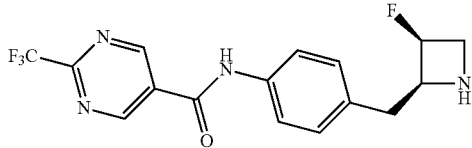 [SMILES: O=C(Nc1ccc(C[C@@H]2NC[C@@H]2F)cc1)c1cnc(C(F)(F)F)nc1]

The title compound was obtained in analogy to example 126 using 2-trifluoromethyl)pyrimidine-5-carboxylic acid in place of 6-methyl-2-trifluoromethyl-pyrimidine-4-carboxylic acid in step (a).

White solid. MS (ISP): 355.2 ([M+H]⁺).

Example 131

N-(4-(((2S,3S)-3-fluoroazetidin-2-yl)methyl)phenyl)-3-isopropyl-1-methyl-1H-pyrazole-5-carboxamide

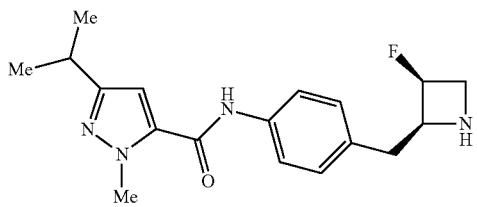 [SMILES: CC(C)c1cc(C(=O)Nc2ccc(C[C@@H]3NC[C@@H]3F)cc2)n(C)n1]

The title compound was obtained in analogy to example 126 using 3-isopropyl-1-methyl-1H-pyrazole-5-carboxylic acid in place of 6-methyl-2-trifluoromethyl-pyrimidine-4-carboxylic acid in step (a). White foam. MS (ISP): 331.2 ([M+H]$^+$).

Example 132

1-[4-[[(2S,3S)-3-fluoroazetidin-2-yl]methyl]phenyl]-3-[6-(trifluoromethyl)-3-pyridyl]urea

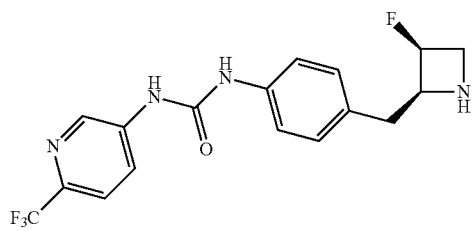 [SMILES: O=C(Nc1ccc(C[C@@H]2NC[C@@H]2F)cc1)Nc1ccc(C(F)(F)F)nc1]

a) (2S,3S)-tert-butyl 3-fluoro-2-(4-(3-(6-(trifluoromethyl)pyridin-3-yl)ureido)benzyl)azetidine-1-carboxylate To a stirred solution of (2S,3S)-tert-butyl 2-(4-aminobenzyl)-3-fluoroazetidine-1-carboxylate (100 mg, 357 μmol) in acetonitrile (3.0 mL) were added at room temperature 6-(trifluoromethyl)pyridin-3-amine (57.8 mg, 357 μmol), triethylamine (98.9 μL, 713 μmol) and finally 4 Å molecular sieves (~0.2 g). After 10 min, N,N'-disuccinimidyl carbonate (101 mg, 392 mol, CAS 74124-79-1) was added and the reaction mixture was stirred at room temperature overnight. The reaction mixture was poured into water and 10 wt. % aqueous citric acid and extracted with CH$_2$Cl$_2$. The combined organic extracts were washed with brine, dried (MgSO$_4$) and concentrated in vacuo. The crude residue was purified by preparative HPLC (mobile phase A: H$_2$O, B: CH$_3$CN with 0.05% Et$_3$N, C18 column) to afford the title compound (41 mg, 25%) as an off-white foam. MS (ISP): 469.3 ([M+H]$^+$).

b) 1-[4-[[(2S,3S)-3-fluoroazetidin-2-yl]methyl]phenyl]-3-[6-(trifluoromethyl)-3-pyridyl]urea 2,2,2-trifluoroacetic acid To a stirred solution of (2S,3S)-tert-butyl 3-fluoro-2-(4-(3-(6-(trifluoromethyl)pyridin-3-yl)ureido)benzyl)azetidine-1-carboxylate (41 mg, 87.5 μmol) in CH$_2$Cl$_2$ (1.0 mL) was added 2,2,2-trifluoroacetic acid (0.5 mL). The reaction mixture was stirred for 2 hours at room temperature before all volatiles were removed under high vacuum. The residue was triturated in EtOH/heptane, filtered and dried under high vacuum to afford the title compound (32 mg, 76%) as a white solid. MS (ISP): 369.3 ([M+H]$^+$).

Example 133

N-[4-[[(2S,3S)-3-fluoroazetidin-2-yl]methyl]phenyl]-3-isopropyl-1H-pyrazole-5-carboxamide

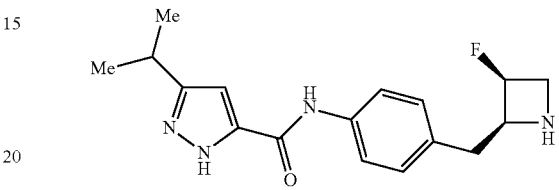

The title compound was obtained in analogy to example 126 using 3-isopropyl-1H-pyrazole-5-carboxylic acid (CAS 92933-47-6) in place of 6-methyl-2-trifluoromethyl-pyrimidine-4-carboxylic acid in step (a). White solid. MS (ISP): 317.2 ([M+H]$^+$).

Example 134

1-[4-[[(2R,3R)-3-fluoroazetidin-2-yl]methyl]phenyl]-3-[6-(trifluoromethyl)-3-pyridyl]urea

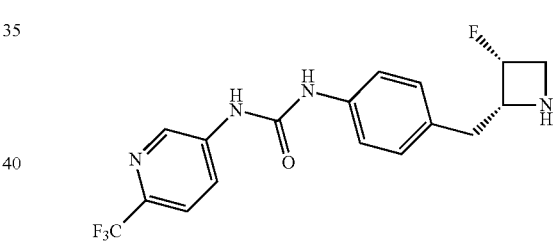

The title compound was obtained in analogy to example 132 using (2R,3R)-tert-butyl 2-(4-aminobenzyl)-3-fluoroazetidine-1-carboxylate in place of (2S,3S)-tert-butyl 2-(4-aminobenzyl)-3-fluoroazetidine-1-carboxylate in step (a). White solid. MS (ISP): 369.1 ([M+H]$^+$).

Example 135

1-(5-cyano-2-methoxy-phenyl)-3-[4-[[(2R,3R)-3-fluoroazetidin-2-yl]methyl]phenyl]urea

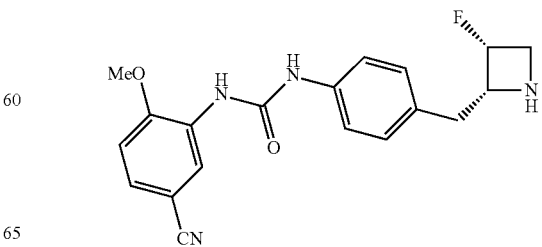

The title compound was obtained in analogy to example 132 using 3-amino-4-methoxybenzonitrile (CAS 60979-25-1) in place of 6-(trifluoromethyl)pyridin-3-amine and (2R,3R)-tert-butyl 2-(4-aminobenzyl)-3-fluoroazetidine-1-carboxylate in place of (2S,3S)-tert-butyl 2-(4-aminobenzyl)-3-fluoroazetidine-1-carboxylate in step (a). White foam. MS (ISP): 355.2 ([M+H]$^+$).

Example 136

1-(5-cyano-2-methoxy-phenyl)-3-[4-[[(2S,3S)-3-fluoroazetidin-2-yl]methyl]phenyl]urea

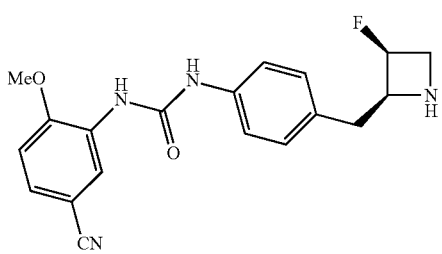 [SMILES: COc1ccc(C#N)cc1NC(=O)Nc1ccc(C[C@@H]2NC[C@@H]2F)cc1]

The title compound was obtained in analogy to example 132 using 3-amino-4-methoxybenzonitrile (CAS 60979-25-1) in place of 6-(trifluoromethyl)pyridin-3-amine in step (a). White solid. MS (ISP): 355.2 ([M+H]$^+$).

Example 137

4-{[(2S,3S)-3-fluoroazetidin-2-yl]methyl]}-N-(3-pyridyl)benzamide

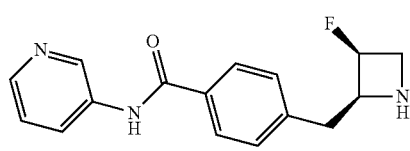 [SMILES: O=C(Nc1cccnc1)c1ccc(C[C@@H]2NC[C@@H]2F)cc1]

a) (S)-benzyl 1-(4-bromophenyl)-4-diazo-3-oxobutan-2-ylcarbamate

To a stirred solution of (S)-2-(benzyloxycarbonylamino)-3-(4-bromophenyl)propanoic acid (5.05 g, 13.4 mmol, CAS 158069-49-9) in CH$_2$Cl$_2$ (25 mL) at 0° C. were added 4 Å molecular sieves (~1.0 g) and 1-chloro-N,N,2-trimethypropenylamine (2.03 mL, 15.4 mmol). After 15 min, the reaction mixture was cooled to −20° C. and slowly added (caution: exothermic!) to a solution of (trimethylsilyl)diazomethane (2.0 M in hexane, 20.0 mL, 40.1 mmol) in CH$_2$Cl$_2$ (25 mL) containing (~1.0 g) of 4 Å molecular sieves at −20° C. The reaction mixture was allowed to warm to room temperature and stirred for 30 min until a red-brown solution was obtained. The reaction mixture was filtered on a sintered funnel and the filtrate was quenched by the addition of saturated aqueous NH$_4$Cl (50 mL). The mixture was extracted with CH$_2$Cl$_2$ and the organic layers were separated, washed with brine, dried (MgSO$_4$), and upon addition of heptane (5 mL), concentrated by rotatory evaporation to 5 mL. The residue was purified by flash chromatography (silica gel, gradient: 5% to 50% EtOAc in heptane) to afford the title compound (6.04 g, 89%) as a yellow oil. MS (ISP): 376.1 ([{$^{81}$Br}M-N$_2$+H]$^+$), 374.1 ([{$^{79}$Br}M-N$_2$+H]$^+$).

b) (S)-benzyl 2-(4-bromobenzyl)-3-oxoazetidine-1-carboxylate

To a stirred solution of (S)-benzyl 1-(4-bromophenyl)-4-diazo-3-oxobutan-2-ylcarbamate (6.06 g, 13.4 mmol) in CH$_2$Cl$_2$ (442 mL) was added Et$_3$N (396 μL, 2.86 mmol) followed by 4 Å molecular sieves (~1.0 g). The reaction mixture was cooled to −40° C. and Rh$_2$(OAc)$_4$ (119 mg, 268 μmol) was added in one portion. The resulting green solution was stirred at −40° C. for 1 hour then allowed to warm to room temperature and stirred for further 3 hours. Triphenylphosphine (251 mg, 0.959 mmol) was added and the reaction mixture was stirred at room temperature for further 15 min till a red solution was obtained. The solvent was evaporated by rotatory evaporation and the resulting residue was purified by flash chromatography (silica gel, gradient: 5% to 40% EtOAc in heptane) to afford the title compound (1.52 g, 30%) as a yellow solid. MS (ISP): 376.1 ([{$^{81}$Br}M+H]$^+$), 374.1 ([{$^{79}$Br}M+H]$^+$).

c) (2S,3S)-benzyl 2-(4-bromobenzyl)-3-hydroxyazetidine-1-carboxylate

To a stirred solution of borane dimethyl sulfide complex (1.87 mL, 3.74 mmol) and (R)-(+)-2-methyl-CBS-oxazaborolidine in THF (1.0 M, 748 μL, 748 μmol, CAS: 112022-83-0) in THF (14 mL) at 0° C. was added a solution of (S)-benzyl 2-(4-bromobenzyl)-3-oxoazetidine-1-carboxylate (1.4 g, 3.74 mmol) in THF (7 mL). The reaction mixture was stirred at 0° C. for 2 hours before being quenched by careful (gas evolution and exothermic!) addition of aqueous HCl (6.0 M, 1.28 mL, 8.75 mmol). The mixture was stirred at room temperature for 10 min, then poured into water and extracted with EtOAc. The combined organic extracts were washed with brine, dried (MgSO$_4$) and concentrated in vacuo. The residue was purified by flash chromatography (silica gel, gradient: 10% to 60% EtOAc in heptane) to afford the title compound (1.15 g, 82%, 96:4 dr) as a light yellow oil. MS (ISP): 378.1 ([{$^{81}$Br}M+H]$^+$), 376.1 ([{$^{79}$Br}M+H]$^+$).

d) (2S,3S)-benzyl 2-(4-bromobenzyl)-3-fluoroazetidine-1-carboxylate

To a stirred solution of triethylamine (310 mg, 424 μL, 3.06 mmol) and Et$_3$N.(HF)$_3$ (986 mg, 6.12 mmol) in CH$_2$Cl$_2$ (7.0 mL) were added XtalFluor-E® (1.05 g, 4.59 mmol) followed by (2S,3S)-benzyl 2-(4-bromobenzyl)-3-hydroxyazetidine-1-carboxylate (1.15 g, 3.06 mmol). The reaction mixture was stirred at room temperature for 1 hour before being quenched by addition of water and saturated aqueous NaHCO$_3$. The mixture was extracted with CH$_2$Cl$_2$ and the combined organic extracts were washed with brine, dried (MgSO$_4$) and concentrated in vacuo. The residue was purified by flash chromatography (silica gel, gradient: 5% to 40% EtOAc in heptane) to afford the title compound (864 mg, 75%) as colorless oil. MS (ISP): 380.1 ([{$^{81}$Br}M+H]$^+$), 378.1 ([{$^{79}$Br}M+H]$^+$).

e) (2S,3S)-benzyl 3-fluoro-2-(4-(methoxycarbonyl)benzyl)azetidine-1-carboxylate

To a stirred solution of (2S,3S)-benzyl 2-(4-bromobenzyl)-3-fluoroazetidine-1-carboxylate (460 mg, 1.22 mmol)

in methanol (2.5 mL) and EtOAc (2.5 mL) were added triethylamine (220 μL, 1.58 mmol) and 1,1'-Bis(diphenylphosphino)ferrocene-palladium(II)dichloride.CH$_2$Cl$_2$ (46.0 mg, 55.8 μmol, CAS 95464-05-4). The reaction mixture was degassed by bubbling nitrogen through the reaction medium for 5 min, then heated to 110° C. under 50 bar CO$_{(g)}$ atmosphere for 16 hours. The solvent was evaporated in vacuo and the residue was purified by flash chromatography (silica gel, gradient: 5% to 50% EtOAc in heptane) to afford the title compound (267 mg, 61%) as a colorless oil. MS (ISP): 358.1 ([M+H]$^+$).

f) 4-(((2S,3S)-1-(benzyloxycarbonyl)-3-fluoroazetidin-2-yl)methyl)benzoic acid To a stirred solution of (2S,3S)-benzyl 3-fluoro-2-(4-(methoxycarbonyl)benzyl)azetidine-1-carboxylate (0.267 g, 747 μmol) in a mixture of methanol (1.0 mL) and THF (8.0 mL) at 0° C. was added an aqueous solution of LiOH (1.0 M, 934 μL, 934 μmol). The reaction mixture was stirred at room temperature overnight before being quenched by addition of 3.0 M aqueous HCl to pH 2-3. The mixture was diluted with water and extracted with EtOAc. The combined organic extracts were dried (MgSO$_4$) and concentrated in vacuo to afford the title compound (203 mg, 79%) as a colorless oil which was used in the following step without further purification. MS (ISP): 344.1 ([M+H]$^+$).

g) (2S,3S)-benzyl 2-(4-(6-chloropyridin-3-ylcarbamoyl)benzyl)-3-fluoroazetidine-1-carboxylate To a stirred suspension of 4-(((2S,3S)-1-(benzyloxycarbonyl)-3-fluoroazetidin-2-yl)methyl)benzoic acid (49.8 mg, 145 μmol) in CH$_2$Cl$_2$ (0.5 mL) at room temperature was added 1-chloro-N,N,2-trimethypropenylamine (22.1 μL, 167 μmol). After 30 min, the resulting solution was added to a solution of 6-chloropyridin-3-amine (20.6 mg, 160 μmol) and N,N-diisopropylethylamine (36 μL, 218 μmol) in DMF (0.5 mL). The reaction mixture was stirred at room temperature for 1 hour then poured into water and extracted with EtOAc. The combined organic extracts were washed with brine, dried (MgSO$_4$) and concentrated in vacuo. The residue was purified by flash chromatography (silica gel, gradient: 10% to 50% EtOAc in heptane) to afford the title compound (29 mg, 44%) as an off-white solid. MS (ISP): 354.2 ([M+H]$^+$).

h) 4-(((2S,3S)-3-fluoroazetidin-2-yl)methyl)-N-(pyridin-3-yl)benzamide dihydrochloride To a stirred solution of (2S,3S)-benzyl 2-(4-(6-chloropyridin-3-ylcarbamoyl)benzyl)-3-fluoroazetidine-1-carboxylate (29 mg, 64 μmol) in MeOH (1.2 mL) under nitrogen were added aqueous HCl (2.0 M, 64 μL, 128 μmol) and 10 wt. % Pd/C (1.4 mg, 1.3 μmol). The resulting black suspension was purged by evacuation and then back filled with a stream of hydrogen (balloon) for three times. The mixture was stirred for 2 hours at room temperature under hydrogen atmosphere. The resulting suspension was filtered directly through a plug of dicalite. The filter cake was rinsed with MeOH and the filtrate was concentrated in vacuo to afford the title compound (8.6 mg, 38%) as a light grey solid. MS (ISP): 286.2 ([M+H]$^+$).

Materials and Methods

Construction of TAAR Expression Plasmids and Stably Transfected Cell Lines

For the construction of expression plasmids the coding sequences of human, rat and mouse TAAR 1 were amplified from genomic DNA essentially as described by Lindemann et al. [14]. The Expand High Fidelity PCR System (Roche Diagnostics) was used with 1.5 mM Mg$^{2+}$ and purified PCR products were cloned into pCR2.1-TOPO cloning vector (Invitrogen) following the instructions of the manufacturer. PCR products were subcloned into the pIRESneo2 vector (BD Clontech, Palo Alto, Calif.), and expression vectors were sequence verified before introduction in cell lines.

HEK293 cells (ATCC # CRL-1573) were cultured essentially as described by Lindemann et al. (2005). For the generation of stably transfected cell lines HEK293 cells were transfected with the pIRESneo2 expression plasmids containing the TAAR coding sequences (described above) with Lipofectamine 2000 (Invitrogen) according to the instructions of the manufacturer, and 24 hrs post transfection the culture medium was supplemented with 1 mg/ml G418 (Sigma, Buchs, Switzerland). After a culture period of about 10 d clones were isolated, expanded and tested for responsiveness to trace amines (all compounds purchased from Sigma) with the cAMP Biotrak Enzyme immunoassay (EIA) System (Amersham) following the non-acetylation EIA procedure provided by the manufacturer. Monoclonal cell lines which displayed a stable EC$_{50}$ for a culture period of 15 passages were used for all subsequent studies.

Radioligand Binding Assay on Rat TAAR1

Membrane Preparation and Radioligand Binding.

HEK-293 cells stably expressing rat TAAR1 were maintained at 37° C. and 5% CO$_2$ in DMEM high glucose medium, containing fetal calf serum (10%, heat inactivated for 30 min at 56° C.), penicillin/streptomycin (1%), and 375 μg/ml geneticin (Gibco). Cells were released from culture flasks using trypsin/EDTA, harvested, washed twice with ice-cold PBS (without Ca$^{2+}$ and Mg$^{2+}$), pelleted at 1,000 rpm for 5 min at 4° C., frozen and stored at −80° C. Frozen pellets were suspended in 20 ml HEPES-NaOH (20 mM, pH 7.4) containing 10 mM EDTA and homogenized with a Polytron (PT 6000, Kinematica) at 14,000 rpm for 20 s. The homogenate was centrifuged at 48,000×g for 30 min at 4° C. Subsequently, the supernatant was removed and discarded, and the pellet resuspended in 20 ml HEPES-NaOH (20 mM, pH 7.4) containing 0.1 mM EDTA using the Polytron (20 s at 14,000 rpm). This procedure was repeated and the final pellet resuspended in HEPES-NaOH containing 0.1 mM EDTA and homogenized using the Polytron. Typically, aliquots of 2 ml membrane portions were stored at −80° C. With each new membrane batch the dissociation constant (K$_d$) was determined via a saturation curve. The TAAR1 radioligand $^3$[H]—(S)-4-[(ethyl-phenyl-amino)-methyl]-4,5-dihydro-oxazol-2-ylamine (described in WO 2008/098857) was used at a concentration equal to the calculated K$_d$ value, that was usually around 2.3 nM, resulting in the binding of approximately 0.2% of the radioligand and a specific binding representing approximately 85% of the total binding. Nonspecific binding was defined as the amount of [H]—(S)-4-[(ethyl-phenyl-amino)-methyl]-4,5-dihydro-oxazol-2-ylamine bound in the presence of 10 M unlabeled ligand. All compounds were tested at a broad range of concentrations (10 pM to 10 μM) in duplicates. The test compounds (20 μl/well) were transferred into a 96 deep well plate (TreffLab), and 180 μl of HEPES-NaOH (20 mM, pH 7.4) containing MgCl$_2$ (10 mM) and CaCl$_2$ (2 mM)

(binding buffer), 300 µl of the radioligand $^3$[H]—(S)-4-[(ethyl-phenyl-amino)-methyl]-4,5-dihydro-oxazol-2-ylamine at a concentration of 3.3×$K_d$ in nM and 500 µl of the membranes (resuspended at 50 g protein per ml) added. The 96 deep well plates were incubated for 1 hr at 4° C. Incubations were terminated by rapid filtration through Unifilter-96 plates (Packard Instrument Company) and glass filters GF/C (Perkin Elmer) presoaked for 1 hr in polyethylenimine (0.3%) and washed 3 times with 1 ml of cold binding buffer. After addition of 45 µl of Microscint 40 (PerkinElmer) the Unifilter-96 plate was sealed and after 1 hr the radioactivity counted using a TopCount Microplate Scintillation Counter (Packard Instrument Company).

Radioligand Binding Assay on Mouse TAAR1
Membrane Preparation and Radioligand Binding.

HEK-293 cells stably expressing mouse TAAR1 were maintained at 37° C. and 5% $CO_2$ in DMEM high glucose medium, containing fetal calf serum (10%, heat inactivated for 30 min at 56° C.), penicillin/streptomycin (1%), and 375 µg/ml geneticin (Gibco). Cells were released from culture flasks using trypsin/EDTA, harvested, washed twice with ice-cold PBS (without $Ca^{2+}$ and $Mg^{2+}$), pelleted at 1,000 rpm for 5 min at 4° C., frozen and stored at −80° C. Frozen pellets were suspended in 20 ml HEPES-NaOH (20 mM, pH 7.4) containing 10 mM EDTA and homogenized with a Polytron (PT 6000, Kinematica) at 14,000 rpm for 20 s. The homogenate was centrifuged at 48,000×g for 30 min at 4° C. Subsequently, the supernatant was removed and discarded, and the pellet resuspended in 20 ml HEPES-NaOH (20 mM, pH 7.4) containing 0.1 mM EDTA using the Polytron (20 s at 14,000 rpm). This procedure was repeated and the final pellet resuspended in HEPES-NaOH containing 0.1 mM EDTA and homogenized using the Polytron. Typically, aliquots of 2 ml membrane portions were stored at −80° C. With each new membrane batch the dissociation constant ($K_d$) was determined via a saturation curve. The TAAR1 radioligand $^3$[H]—(S)-4-[(ethyl-phenyl-amino)-methyl]-4,5-dihydro-oxazol-2-ylamine (described in WO 2008/098857) was used at a concentration equal to the calculated $K_d$ value, that was usually around 0.7 nM, resulting in the binding of approximately 0.5% of the radioligand and a specific binding representing approximately 70% of the total binding. Nonspecific binding was defined as the amount of $^3$[H]—(S)-4-[(ethyl-phenyl-amino)-methyl]-4,5-dihydro-oxazol-2-ylamine bound in the presence of 10 M unlabeled ligand. All compounds were tested at a broad range of concentrations (10 pM to 10 µM) in duplicates. The test compounds (20 µl/well) were transferred into a 96 deep well plate (TreffLab), and 180 µl of HEPES-NaOH (20 mM, pH 7.4) containing $MgCl_2$ (10 mM) and $CaCl_2$ (2 mM) (binding buffer), 300 µl of the radioligand $^3$[H]—(S)-4-[(ethyl-phenyl-amino)-methyl]-4,5-dihydro-oxazol-2-ylamine at a concentration of 3.3×$K_d$ in nM and 500 µl of the membranes (resuspended at 60 g protein per ml) added. The 96 deep well plates were incubated for 1 hr at 4° C. Incubations were terminated by rapid filtration through Unifilter-96 plates (Packard Instrument Company) and glass filters GF/C (Perkin Elmer) presoaked for 1 hr in polyethylenimine (0.3%) and washed 3 times with 1 ml of cold binding buffer. After addition of 45 µl of Microscint 40 (PerkinElmer) the Unifilter-96 plate was sealed and after 1 hr the radioactivity counted using a TopCount Microplate Scintillation Counter (Packard Instrument Company).

The compounds show a $K_i$ value in mouse or rat on TAAR1 (in M) as shown in the table below.

| Example | $K_i$(µM) mouse/rat |
|---|---|
| 1 | 1.5672/0.7009 |
| 2 | 0.0272/0.2115 |
| 3 | 0.0777/0.66 |
| 4 | 0.0011/0.0087 |
| 5 | 0.0123/0.0362 |
| 6 | 0.0195/0.0234 |
| 7 | 0.0056/0.0058 |
| 8 | 0.055/0.1648 |
| 9 | 0.0477/0.1053 |
| 10 | 0.4137/0.0887 |
| 11 | 0.0645/0.0808 |
| 12 | 0.1373/0.0927 |
| 13 | 0.0033/0.0178 |
| 14 | 0.0149/0.1002 |
| 15 | 0.0571/0.2607 |
| 16 | 0.0746/0.6325 |
| 17 | 0.0729/0.0969 |
| 18 | 0.109/1.6334 |
| 19 | 0.0128/0.0208 |
| 20 | 0.4777/1.0318 |
| 21 | 0.6527/0.0207 |
| 22 | 2.0254/0.0672 |
| 23 | 0.0099/0.038 |
| 24 | 0.0328/0.0701 |
| 25 | 0.003/0.0113 |
| 26 | 0.0161/0.0238 |
| 27 | 0.0155/0.0628 |
| 28 | 0.0096/0.0284 |
| 29 | 0.029/0.0503 |
| 30 | 0.0191/0.5272 |
| 31 | 0.0036/0.0151 |
| 32 | 0.0134/0.0145 |
| 33 | 0.0075/0.0115 |
| 34 | 0.0009/0.0021 |
| 35 | 0.0031/0.0466 |
| 36 | 0.0139/0.029 |
| 37 | 0.0007/0.0026 |
| 38 | 0.0351/0.8528 |
| 39 | 0.0628/0.476 |

| Example | Ki(μM) mouse/rat |
|---|---|
| 40 | 0.0028/0.0142 |
| 41 | 0.0035/0.0392 |
| 42 | 0.015/0.1132 |
| 43 | 0.0068/0.0435 |
| 44 | 0.0085/0.1649 |
| 45 | 0.0355/0.1292 |
| 46 | 1.9935/0.5516 |
| 47 | 0.0039/0.0468 |
| 48 | 0.0143/0.0943 |
| 49 | 1.3927/0.2911 |
| 50 | 0.7933/0.0998 |
| 51 | 0.0011/0.0515 |
| 52 | 0.0009/0.0035 |
| 53 | 0.0552/2.4277 |
| 54 | 0.003/0.0182 |
| 55 | 0.0161/0.0059 |
| 56 | 0.0034/0.0151 |
| 57 | 0.0147/0.0369 |
| 58 | 0.0014/0.0188 |
| 59 | 0.0089/0.0079 |
| 60 | 0.0084/0.0099 |
| 61 | 0.1206/0.2465 |
| 62 | 0.0081/0.0181 |
| 63 | 0.0614/0.0385 |
| 64 | 0.015/0.0615 |
| 65 | 0.0026/0.023 |
| 66 | 0.323/0.0824 |
| 67 | 0.0294/0.0968 |
| 68 | 0.0064/0.0071 |
| 69 | 0.0421/0.0361 |
| 70 | 0.0069/0.0099 |
| 71 | 0.001/0.0065 |
| 72 | 0.0039/0.0686 |
| 73 | 0.0136/0.0543 |
| 74 | 0.0529/0.0417 |
| 75 | 0.0052/0.0106 |
| 76 | 0.054/0.167 |
| 77 | 0.004/0.0187 |
| 78 | 0.0293/0.2694 |
| 79 | 0.01/0.3481 |
| 80 | 0.0272/0.026 |
| 81 | 0.0041/0.0202 |
| 82 | 0.0278/0.0055 |
| 83 | 0.0167/0.0009 |
| 84 | 0.0033/0.0014 |
| 85 | 0.0509/0.0134 |
| 86 | 0.0018/0.0038 |
| 87 | 0.0122/0.0024 |
| 88 | 0.0174/0.005 |
| 89 | 1.5228/0.0822 |
| 90 | 4.3802/0.2744 |
| 91 | 1.0725/0.1486 |
| 92 | 0.244/0.6065 |
| 93 | 1.2791/2.0861 |
| 94 | 4.0486/0.7674 |
| 95 | 2.7706/0.6482 |
| 96 | 2.7638/0.7047 |
| 97 | 1.6304/0.3241 |
| 98 | 0.2005/13.447 |
| 99 | 0.2005/13.447 |
| 100 | 0.3172/0.1506 |
| 101 | 2.6062/2.0365 |
| 102 | 0.0148/0.0875 |
| 103 | 0.0456/1.2691 |
| 104 | 0.0108/0.0231 |
| 105 | 0.0019/0.0016 |
| 106 | 0.0019/0.0239 |
| 107 | 0.0025/0.0026 |
| 108 | 0.108/0.0269 |
| 109 | 0.0046/0.003 |
| 110 | 0.0131/0.0081 |
| 111 | 0.161/0.1393 |
| 112 | 0.0111/0.0111 |
| 113 | 0.0087/0.0042 |
| 114 | 0.1597/0.1559 |
| 115 | 0.0272/0.0138 |

-continued

| Example | Ki(μM) mouse/rat |
|---|---|
| 116 | 0.0037/0.0016 |
| 117 | 0.0277/0.0154 |
| 118 | 0.0038/0.0021 |
| 119 | 0.3363/1.1779 |
| 120 | 0.0103/>1.5 |
| 121 | 0.007/0.8095 |
| 122 | 0.0097/1.164 |
| 123 | 0.0232/0.6101 |
| 124 | 0.0554/>1.5 |
| 125 | 0.016/0.4656 |
| 126 | 0.0229/0.0224 |
| 127 | 0.0038/0.1326 |
| 128 | 0.0023/0.0204 |
| 129 | 0.0089/0.055 |
| 130 | 0.0282/0.0156 |
| 131 | 0.1192/0.126 |
| 132 | −/− |
| 133 | −/− |
| 134 | −/− |
| 135 | −/− |
| 136 | −/− |
| 137 | −/− |

The compounds of formula I and the pharmaceutically acceptable salts of the compounds of formula I can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. The administration can, however, also be effected rectally, e.g. in the form of suppositories, or parenterally, e.g. in the form of injection solutions.

The compounds of formula I can be processed with pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are however usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of formula I or a pharmaceutically acceptable salt thereof and a therapeutically inert carrier are also an object of the present invention, as is a process for their production, which comprises bringing one or more compounds of formula I and/or pharmaceutically acceptable acid addition salts and, if desired, one or more other therapeutically valuable substances into a galenical administration form together with one or more therapeutically inert carriers.

The most preferred indications in accordance with the present invention are those which include disorders of the central nervous system, for example the treatment or prevention of depression, psychosis, Parkinson's disease, anxiety, attention deficit hyperactivity disorder (ADHD) and diabetes.

The dosage can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage may be administered as single dose or in divided doses and, in addition, the upper limit can also be exceeded when this is found to be indicated.

| Tablet Formulation (Wet Granulation) | | | | |
|---|---|---|---|---|
| | | mg/tablet | | |
| Item Ingredients | 5 mg | 25 mg | 100 mg | 500 mg |
| 1. Compound of formula I | 5 | 25 | 100 | 500 |
| 2. Lactose Anhydrous DTG | 125 | 105 | 30 | 150 |
| 3. Sta-Rx 1500 | 6 | 6 | 6 | 30 |
| 4. Microcrystalline Cellulose | 30 | 30 | 30 | 150 |
| 5. Magnesium Stearate | 1 | 1 | 1 | 1 |
| Total | 167 | 167 | 167 | 831 |

Manufacturing Procedure

1. Mix items 1, 2, 3 and 4 and granulate with purified water.
2. Dry the granules at 50° C..
3. Pass the granules through suitable milling equipment.
4. Add item 5 and mix for three minutes; compress on a suitable press.

| Capsule Formulation | | | | |
|---|---|---|---|---|
| | | mg/capsule | | |
| Item Ingredients | 5 mg | 25 mg | 100 mg | 500 mg |
| 1. Compound of formula I | 5 | 25 | 100 | 500 |
| 2. Hydrous Lactose | 159 | 123 | 148 | — |
| 3. Corn Starch | 25 | 35 | 40 | 70 |
| 4. Talc | 10 | 15 | 10 | 25 |
| 5. Magnesium Stearate | 1 | 2 | 2 | 5 |
| Total | 200 | 200 | 300 | 600 |

Manufacturing Procedure

1. Mix items 1, 2 and 3 in a suitable mixer for 30 minutes.
2. Add items 4 and 5 and mix for 3 minutes.
3. Fill into a suitable capsule.

We claim:
1. A compound of formula I

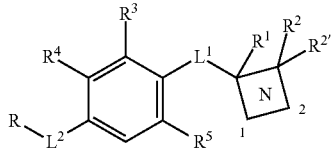

wherein:
R¹ is hydrogen, methoxy or fluoro;
R² and R²' are independently selected from hydrogen, methoxy or fluoro;
R³ and R⁴ are independently selected from hydrogen or halogen;
R⁵ is hydrogen or fluoro;
L¹ is —O—;
R' is hydrogen or lower alkyl;
L² is a bond —C(O)NH—, —NH—, —CH₂NHC(O)—, —NHC(O)— or —NHC(O)NH—;
R is phenyl or heteroaryl wherein said heteroaryl is selected from the group consisting of pyridinyl, pyrimidinyl, pyrazinyl, pyridazinyl and pyrazolyl and said phenyl is optionally substituted by one or more substituents selected from halogen, lower alkyl substituted by halogen or lower alkoxy, and said heteroaryl is optionally substituted by one or more substituents selected from the group consisting of halogen, lower alkyl, lower alkoxy, cyano, cycloalkyl, lower alkyl substituted by halogen, lower alkoxy substituted by halogen and phenyl substituted by halogen,
or, if L² is a bond, R is halogen, lower alkoxy or cyano;
N is a ring nitrogen atom in position 1 or 2;
or a pharmaceutically suitable acid addition salt thereof, an enantiomer, a racemic mixture, or a mixture of enantiomers.

2. The compound according to claim 1 which compound is IB-3

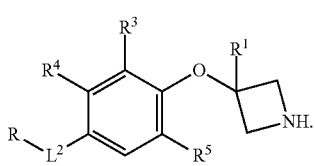

3. The compound of according to claim 2, which compound is selected from the group consisting of:
N-(4-(azetidin-3-yloxy)phenyl)-4-chlorobenzamide;
N-(4-(azetidin-3-yloxy)phenyl)-2-(trifluoromethyl)isonicotinamide;
N-(4-(azetidin-3-yloxy)phenyl)-2-(trifluoromethyl)pyrimidine-5-carboxamide;
N-(4-(azetidin-3-yloxy)phenyl)-2-cyano-6-methoxy-isonicotinamide;
N-[4-(azetidin-3-yloxy)phenyl]-2-(trifluoromethyl)pyrimidin-4-amine;
N-(4-(azetidin-3-yloxy)phenyl)-5-(trifluoromethyl)pyrimidin-2-amine;
N-(4-(azetidin-3-yloxy)phenyl)-3-cyclopropyl-1H-pyrazole-5-carboxamide;
N-(4-(azetidin-3-yloxy)phenyl)-3-ethyl-4-methyl-1H-pyrazole-5-carboxamide;
N-(4-(azetidin-3-yloxy)phenyl)-3-isopropyl-1H-pyrazole-5-carboxamide;
N-(4-(azetidin-3-yloxy)phenyl)-4-chloro-3-cyclopropyl-1H-pyrazole-5-carboxamide;
N-(4-(azetidin-3-yloxy)phenyl)-2-cyclopropylpyrimidine-5-carboxamide;
N-[4-(azetidin-3-yloxy)phenyl]-2-ethyl-pyrimidine-5-carboxamide;
N-[4-(azetidin-3-yloxy)phenyl]-2-methyl-pyrimidine-5-carboxamide;
N-[4-(azetidin-3-yloxy)phenyl]-2-methyl-5-(trifluoromethyl)pyrazole-3-carboxamide;
4-(azetidin-3-yloxy)-N-[(4-fluorophenyl)methyl]benzamide;
N-(4-(azetidin-3-yloxy)phenyl)-2-(2,2,2-trifluoroethoxy)pyrimidine-5-carboxamide;
4-(azetidin-3-yloxy)-N-phenyl-benzamide;
N-[4-(azetidin-3-yloxy)phenyl]-4-chloro-1-(2,2,2-trifluoroethyl)pyrazole-3-carboxamide;
N-[4-(azetidin-3-yloxy)phenyl]-4-chloro-1-ethyl-pyrazole-3-carboxamide;
4-(azetidin-3-yloxy)-N-(4-chlorophenyl)benzamide;
N-(4-(azetidin-3-yloxy)phenyl)-3-(trifluoromethyl)-1H-pyrazole-5-carboxamide;
N-[4-(azetidin-3-yloxy)-3-fluoro-phenyl]-4-chloro-3-cyclopropyl-1H-pyrazole-5-carboxamide;
N-[4-(azetidin-3-yloxy)-3-fluoro-phenyl]-2-(trifluoromethyl)pyrimidine-5-carboxamide;
N-[4-(azetidin-3-yloxy)-3-fluoro-phenyl]-2-cyclopropyl-pyrimidine-5-carboxamide;
N-[4-(azetidin-3-yloxy)-3-fluoro-phenyl]-6-ethoxy-pyridine-3-carboxamide;
N-[4-(azetidin-3-yloxy)phenyl]-4-chloro-2-methyl-5-(trifluoromethyl)pyrazole-3-carboxamide;
4-(azetidin-3-yloxy)-N-(6-chloropyridin-3-yl)benzamide;
N-[4-(azetidin-3-yloxy)phenyl]-4-bromo-3-cyclopropyl-1H-pyrazole-5-carboxamide;
N-[4-(azetidin-3-yloxy)phenyl]-3-tert-butyl-4-chloro-1H-pyrazole-5-carboxamide;
N-[4-(azetidin-3-yloxy)phenyl]-4-chloro-3-isopropyl-1H-pyrazole-5-carboxamide;
N-[4-(azetidin-3-yloxy)phenyl]-4-chloro-3-(4-chlorophenyl)-1H-pyrazole-5-carboxamide;
N-[4-(azetidin-3-yloxy)-2-fluoro-phenyl]-4-chloro-3-cyclopropyl-1H-pyrazole-5-carboxamide;
4-(azetidin-3-yloxy)-N-(4-chloro-3-(trifluoromethyl)phenyl)benzamide;
N-[4-(azetidin-3-yloxy)-2-fluoro-phenyl]-2-cyclopropyl-pyrimidine-5-carboxamide;
N-[4-(azetidin-3-yloxy)-2-fluoro-phenyl]-2-(trifluoromethyl)pyrimidine-5-carboxamide;
N-[4-(azetidin-3-yloxy)phenyl]-4-chloro-3-(trifluoromethyl)-1H-pyrazole-5-carboxamide;
N-[4-(azetidin-3-yloxy)phenyl]-4-chloro-3-ethyl-1H-pyrazole-5-carboxamide;
N-[4-(azetidin-3-yloxy)phenyl]-3-cyclopropyl-4-fluoro-1H-pyrazole-5-carboxamide;
N-[4-(azetidin-3-yloxy)phenyl]-4-chloro-1-methyl-5-(trifluoromethyl)pyrazole-3-carboxamide;
N-[4-(azetidin-3-yloxy)phenyl]-4-bromo-3-ethyl-1H-pyrazole-5-carboxamide;
N-[4-(azetidin-3-yloxy)phenyl]-4-bromo-3-methyl-1H-pyrazole-5-carboxamide;
4-(azetidin-3-yloxy)-2-chloro-N-(6-chloro-3-pyridyl)benzamide;

N-[4-(azetidin-3-yloxy)phenyl]-5-(trifluoromethyl)pyrazine-2-carboxamide;

N-[4-(azetidin-3-yloxy)phenyl]-6-ethoxy-pyridazine-3-carboxamide;

N-[4-(azetidin-3-yloxy)phenyl]-5-(2,2,2-trifluoroethoxy)pyrazine-2-carboxamide;

1-[4-(azetidin-3-yloxy)phenyl]-3-(4-methoxyphenyl)urea; and,

1-[4-(azetidin-3-yloxy)phenyl]-3-(3-chlorophenyl)urea.

4. A pharmaceutical composition comprising a compound according to claim 1 and at least one pharmaceutically acceptable carrier, excipient or adjuvant.

* * * * *